(12) United States Patent
Lee et al.

(10) Patent No.: US 10,991,888 B2
(45) Date of Patent: *Apr. 27, 2021

(54) COMPOUND FOR ORGANIC ELECTRONIC ELEMENT, ORGANIC ELECTRONIC ELEMENT USING THE SAME, AND AN ELECTRONIC DEVICE

(71) Applicant: DUK SAN NEOLUX CO., LTD., Cheonan-si (KR)

(72) Inventors: Bum Sung Lee, Cheonan-si (KR); Sun Hee Lee, Cheonan-si (KR); Soung Yun Mun, Cheonan-si (KR); Jung Cheol Park, Suwon-si (KR); Hak Young Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 374 days.

This patent is subject to a terminal disclaimer.

(21) Appl. No.: 15/999,002

(22) Filed: Aug. 20, 2018

(65) Prior Publication Data

US 2019/0006597 A1    Jan. 3, 2019

Related U.S. Application Data

(63) Continuation of application No. 15/507,046, filed as application No. PCT/KR2015/007998 on Jul. 30, 2015, now Pat. No. 10,056,560.

(30) Foreign Application Priority Data

Aug. 29, 2014 (KR) .......................... 10-2014-0113885

(51) Int. Cl.

| | |
|---|---|
| *H01L 51/50* | (2006.01) |
| *H01L 51/00* | (2006.01) |
| *C09K 11/06* | (2006.01) |
| *H05B 33/20* | (2006.01) |
| *C07C 211/54* | (2006.01) |
| *C07C 211/58* | (2006.01) |
| *C07C 211/61* | (2006.01) |
| *C07D 209/86* | (2006.01) |
| *C07D 333/76* | (2006.01) |
| *C07D 209/82* | (2006.01) |

(52) U.S. Cl.
CPC ........ *H01L 51/0061* (2013.01); *C07C 211/54* (2013.01); *C07C 211/58* (2013.01); *C07C 211/61* (2013.01); *C07D 209/82* (2013.01); *C07D 209/86* (2013.01); *C07D 333/76* (2013.01); *C09K 11/06* (2013.01); *H01L 51/006* (2013.01); *H01L 51/0058* (2013.01); *H01L 51/0059* (2013.01); *H01L 51/0072* (2013.01); *H01L 51/0074* (2013.01); *H01L 51/50* (2013.01); *H05B 33/20* (2013.01); *C07C 2603/97* (2017.05); *C09K 2211/1007* (2013.01); *C09K 2211/1014* (2013.01); *C09K 2211/1022* (2013.01); *C09K 2211/1092* (2013.01); *H01L 51/0052* (2013.01); *H01L 51/0056* (2013.01); *H01L 51/5012* (2013.01); *H01L 51/5056* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 6,242,115 B1 | 6/2001 | Thomson et al. | |
| 2008/0164809 A1 | 7/2008 | Matsunami et al. | |
| 2012/0018717 A1 | 1/2012 | Kim et al. | |
| 2013/0277656 A1 | 10/2013 | Seo et al. | |
| 2014/0374722 A1* | 12/2014 | Kim | .................. H01L 51/0061 257/40 |
| 2016/0351825 A1* | 12/2016 | Kim | ..................... C07D 495/04 |

FOREIGN PATENT DOCUMENTS

| | | |
|---|---|---|
| KR | 10-2011-0041934 A | 4/2011 |
| KR | 10-2011-0118542 A | 10/2011 |
| KR | 10-2012-0034648 A | 4/2012 |
| KR | 10-1389527 B1 | 4/2014 |
| KR | 10-2014-0087987 A | 7/2014 |

* cited by examiner

*Primary Examiner* — Gregory D Clark
(74) *Attorney, Agent, or Firm* — Vorys, Sater, Seymour & Pease LLP; Mih Suhn Koh

(57) ABSTRACT

Provided is an organic electronic element comprising a hole transport layer containing a compound of Formula (1) and an emitting auxiliary layer containing a compound of Formula (2), capable of improving the light emitting efficiency, stability, and life span of an electronic device using the same.

14 Claims, No Drawings

COMPOUND FOR ORGANIC ELECTRONIC ELEMENT, ORGANIC ELECTRONIC ELEMENT USING THE SAME, AND AN ELECTRONIC DEVICE

TECHNICAL FIELD

The present invention relates to compound for organic electronic element, organic electronic element using the same, and an electronic device thereof.

BACKGROUND ART

Recently, organic electroluminescence display devices using an emitting material as an emitting element of a display has been actively developed. Unlike a liquid crystal display device or the like, an organic EL display device is a so-called self-luminous type in which realize a display by emitting an emitting material containing an organic compound in an emitting layer by recombining a hole and an electron injected into an anode and a cathode in the emitting layer.

It has been recently proposed that an organic electroluminescence element (hereinafter will be abbreviated as an organic EL element) is composed of a plurality of different layers, such as an emitting layer and a layer for transporting carriers (holes, electrons) in the emitting layer and the like.

In order to improve the luminescent characteristics of the organic EL element and to achieve longevity, it is required that the hole transport layer has excellent hole transporting ability and carrier resistance. From this point of view, various hole transport materials have been proposed.

As a material usable for each layer of the organic EL element, various compounds such as an aromatic amine compound are known. For example, Patent Document 1 using a carbazole derivative as a hole transport layer, and Patent Document 2 using an amine compound having deuterium as a hole transport material and a host material of an emitting layer, and Patent Document 3 using a tertiary amine structure substituted with a simple aryl group as a hole transport material, and Patent Document 4 using an amine compound having a fluorenyl group as a hole transport material or an injection material, and the like have been reported.

However, it is difficult to say that organic EL element using these materials have a sufficient emitting life span, therefore, there is currently a demand for an organic EL element capable of driving at a lower voltage with higher efficiency and also having a longer emitting life span.

DISCLOSURE OF THE INVENTION

Technical Problem

The present invention is to provide an organic electroluminescence device with improved element and efficiency, an organic light emitting material for realizing the same, and an electronic device using the same, by preventing interface deterioration of an emitting layer, and by increasing the charge balance in the emitting layer.

Technical Solution

Recently, the most problematic issues in an organic electroluminescence device are high stability of life span and high efficiency. This is the most demanded part as the organic electroluminescence device becomes increasingly large-sized. Also, in recent years, in order to solve the emitting problem and the driving voltage problem in the hole transport layer in organic electroluminescence devices, an emitting-auxiliary layer (multilayered hole transport layer) must be present between the hole transport layer and the emitting layer, and it is necessary to develop different emitting-auxiliary layers according to each emitting layer.

Generally, electrons are transferred from the electron transport layer to the emitting layer, and a hole is transferred from the hole transport layer to the emitting layer, and recombination occurs in the emitting layer to form an exciton. But, in case materials with high hole mobility are used in order to make low driving voltage, Positive Polaron is accumulated at the interface between the emitting layer and the hole transport layer, as a result, interface deterioration occurs to reduce the life span and efficiency, and additionally the charge balance in the emitting layer does not match, surplus polaron in the emitting layer attacks weak bonding of the emitting material, and the emitting material is deformed, thereby exhibiting a phenomenon such as a decrease in life span, efficiency, and color purity.

Accordingly, the emitting auxiliary layer is present between the hole transport layer and the emitting layer and, must be a material having a proper HOMO value between the emitting layer and the hole transport layer in order to prevent the positive polaron from accumulating on the emitting layer interface, it should be a material having a hole mobility within a suitable driving voltage range (within a ble device driving voltage range of full device) in order to increase the charge balance in the emitting layer.

However, this cannot be achieved simply by the structural characteristics of the core of the emitting auxiliary layer material, when the characteristics of the core of the emitting auxiliary layer material and of the sub-substituent, and the proper combination between the emitting auxiliary layer and the hole transport layer, and between the emitting auxiliary layer and the emitting layer are made, a device with high efficiency and long life span can be realized.

The present invention has been made in view of the above problems, and it is an object of the present invention to provide an organic electroluminescence device with improved device and efficiency and an organic luminescent material for realizing the same by preventing interface deterioration of the luminescent layer and increasing the charge balance in the luminescent layer.

The present invention also provides an organic electronic element and an electronic device using a carbazole derivative as a hole transport layer material, and using a tertiary amine substituted with an aryl or a heterocyclic group as an emitting auxiliary layer material.

The present invention also provides an organic electronic element characterized by comprising a first electrode, a second electrode, and an organic material layer formed between the first electrode and the second electrode, wherein the organic material layer comprises an emitting auxiliary layer formed between the first electrode and the emitting layer, and a hole transport layer formed between the first electrode and the emitting auxiliary layer, wherein the hole transport layer contains a compound represented by the following formula (1), and the emitting auxiliary layer contains a compound represented by the following Formula (2).

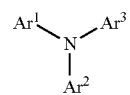

<Formula (1)>

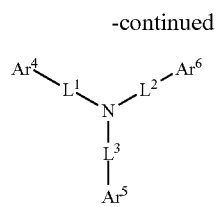

<Formula (2)>

Advantageous Effects

By using the laminate including the emitting auxiliary layer and the hole transport layer according to the present invention, the deterioration of the interface of the emitting layer is prevented, and by increasing the charge balance in the emitting layer, thereby the high luminous efficiency, low driving voltage, high color purity, and life span can be greatly improved.

MODE FOR CARRYING OUT THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected ",", coupled" or "connected" between each component.

As used in the specification and the accompanying claims, unless otherwise stated, the following is the meaning of the term as follows.

Unless otherwise stated, the term "halo" or "halogen" as used herein includes F, Br, Cl, or I.

Unless otherwise stated, the term "alkyl" or "alkyl group" as used herein has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl" as used herein means an alkyl group substituted with a halogen.

Unless otherwise stated, the term "heteroalkyl" as used herein means alkyl substituted one or more carbon atoms with heteroatom.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an oxygen radical attached to an alkyl group, but not limited to, and has 1 to 60 carbon atoms.

Unless otherwise stated, the term "alkenoxyl group", "alkenoxy group", "alkenyloxyl group" or "alkenyloxy group" as used herein means an oxygen radical attached to an alkenyl group, but not limited to, and has 2 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or the arylene group means a monocyclic or polycyclic aromatic group, and may include the aromatic ring formed in conjunction or reaction with an adjacent substituent. For examples, the aryl group may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_2$ to $C_{60}$ aryl or arylene group containing one or more heteroatoms, and includes at least one of monocyclic or polycyclic rings, and may also be formed in conjunction with an adjacent group.

Unless otherwise stated, the term "heterocyclic group" as used herein contains one or more heteroatoms, but not limited to, has 2 to 60 carbon atoms, includes both monocyclic and polycyclic rings, and may include heteroaliphadic ring and/or heteroaromatic ring. Also, the heterocyclic group may also be formed in conjunction with an adjacent group.

Unless otherwise stated, the term "heteroatom" as used herein represents at least one of N, O, S, P, or Si.

Also, the term "heterocyclic group" may include $SO_2$ instead of carbon consisting of cycle. For example, "heterocyclic group" includes compound below.

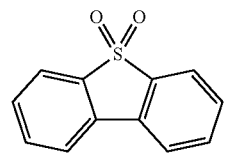 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds contain, but are not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynl having 2 to 20 carbon atoms, or the combination of these.

Unless otherwise expressly stated, the term "substituted or unsubstituted" as used herein means that "substitution" is substituted with at least one substituent selected from the group consisting of, but not limited to, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the formula used in the present invention is applied in the same manner as the substituent definition according to the definition of the exponent of the following Formula.

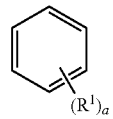

Wherein, when a is an integer of zero, the substituent $R^1$ is absent, when a is an integer of 1, the sole $R^1$ is linked to any one of the carbon atoms constituting the benzene ring, when a is an integer of 2 or 3, each substituent $R^1$s are linked to the benzene ring as follows and may be the same and different. When a is an integer of 4 to 6, the substituent $R^1$s are linked to carbon atoms of the benzene ring in a similar manner, and the indication of hydrogen bound to the carbon forming the benzene ring is omitted.

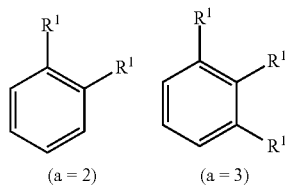

Further, the organic electronic element according to the present invention may be any one of an organic light emitting diode (OLED), an organic solar cell, an organic photo conductor (OPC), an organic transistor (organic TFT), and an element for monochromatic or white illumination.

Another embodiment of the present invention may include an electronic device including the display device which includes the described organic electronic element of the present invention, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electronic element according to an aspect of the present invention will be described.

According to an embodiment of the present invention, there is provided an organic electronic element comprising a first electrode, a second electrode, and an organic layer formed between the first electrode and the second electrode, wherein the organic material layer includes an emitting auxiliary layer formed between the first electrode and the emitting layer, and a hole transport layer formed between the first electrode and the emitting auxiliary layer, wherein the hole transport layer contains a compound represented by the following Formula (1), and the emitting auxiliary layer contains a compound represented by the following Formula (2).

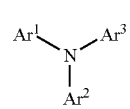

<Formula (1)>

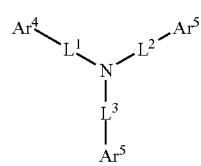

<Formula (2)>

In the Formulas (1) and (2), wherein $Ar^1$, $Ar^2$, $Ar^4$, $Ar^5$ and $Ar^6$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group; a $C_2$-$C_{20}$ alkynyl group; a $C_1$-$C_{20}$ alkoxyl group, a $C_6$-$C_{30}$ aryloxy group; and -L'-N ($R_a$)($R_b$)(where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring; and a $C_2$-$C_{60}$ heterocyclic group containing at least one heteroatom of O, N, S, Si, or P)

$Ar^3$ is at least one of the Formula (1-a) or Formula (1-b) below.

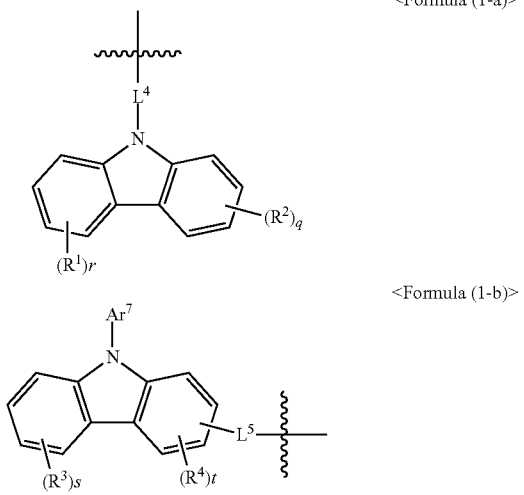

<Formula (1-a)>

<Formula (1-b)> q, r and s are integer of 0 to 4, t is an integer of 0 to 3, and $R^1$, $R^2$, $R^3$, $R^4$ may be the same or different, and are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$) (wherein, L', $R_a$ and $R_b$ are the same as indicated above), or in case q, r and s are 2 or more, R', $R^2$ and $R^3$ are each in plural and are the same or different, and a plurality of $R^1$ or a plurality of $R^2$ or a plurality of $R^3$ or a plurality of $R^4$ may combine to each other to form a ring.

$L^4$ may be selected from the group consisting of a $C_6$-$C_{60}$ arylene group, and a fluorenylene group; a fused ring group of a $C_3$-$C_{60}$ aliphatic ring and a $C_6$-$C_{60}$ aromatic ring; and a $C_2$-$C_{60}$ heterocyclic group including at least one heteroatom of O, N, S, Si or P.

$L^5$ may be selected from the group consisting of a single bond, a $C_6$-$C_{60}$ arylene group, and a fluorenylene group; a fused ring group of a $C_3$-$C_{60}$ aliphatic ring and a $C_6$-$C_{60}$ aromatic ring; and a $C_2$-$C_{60}$ heterocyclic group including at least one heteroatom of O, N, S, Si or P.

$Ar^7$ may be independently selected from the group consisting of a $C_6$-$C_{60}$ aryl group, and a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$) (wherein, L', $R_a$ and $R_b$ are as defined above).

$L^1$, $L^2$, $L^3$ may be selected from the group consisting of a single bond, a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P.

Aryl group, fluorenyl group, heterocyclic group, fused ring group, alkyl group, alkenyl group, alkynyl group, alkoxyl group, aryloxy group, arylene group and fluorenylene group may be substituted with one or more substituents selected from deuterium; halogen; a silane group; a siloxane group; boron group; a germanium group; a cyano group; a nitro group; -L'-N ($R_a$)($R_b$); a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{60}$ aryl group; a $C_6$-$C_{60}$ aryl group substituted with deuterium; a fluorenyl group; a $C_2$-$C_{20}$ heterocyclic group; a $C_3$-$C_{20}$ cycloalkyl group; the group consisting of a $C_7$-$C_{20}$ arylalkyl group and a $C_8$-$C_{20}$ arylalkenyl group, and also, these substituents may combine each other and form a ring, wherein the term 'ring' means a $C_3$-$C_{60}$ aliphatic ring or a $C_6$-$C_{60}$ aromatic ring or a $C_2$-$C_{60}$ heterocyclic ring or a fused ring formed by the combination of them, and includes a saturated or unsaturated ring.

In another example of the present invention, the compound represented by the Formula (1) may be one of compounds of the following Formulas (3) to (4).

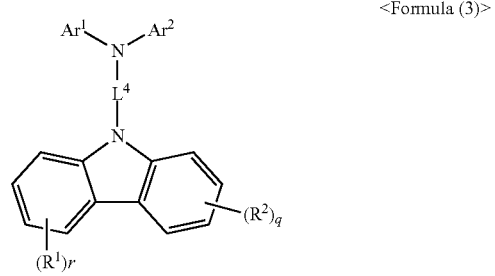

<Formula (3)>

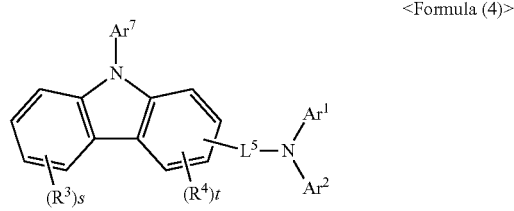

<Formula (4)>

Hereinafter, $R^1$, $R^2$, $R^3$, $R^4$, $L^4$, $L^5$, $Ar^1$, $Ar^2$, $Ar^7$, q, r, s, and t are the same as $R^1$, $R^2$, $R^3$, $R^4$, $L^4$, $L^5$, $Ar^1$, $Ar^2$, $Ar^7$, q, r, s, and t defined in the Formula (1).

In another example of the present invention, the compound represented by the Formula (1) is one of compounds of the following Formulas (5) to (7).

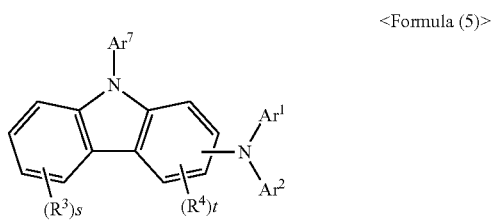

<Formula (5)>

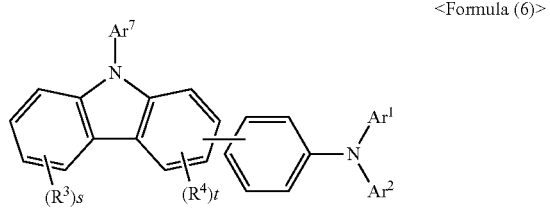

<Formula (6)>

-continued

<Formula (7)>

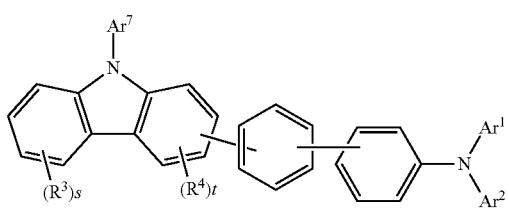

Hereinafter, $R^3$, $R^4$, $Ar^1$, $Ar^2$, $Ar^7$, s, and t are the same as $R^3$, $R^4$, $Ar^1$, $Ar^2$, $Ar^7$, s, and t defined in the Formula (1).

In another specific example of the present invention, the compound represented by the Formula (2) of the emission-auxiliary layer may be any one of compounds of Formula (8) to Formula (12) below.

<Formula (8)>

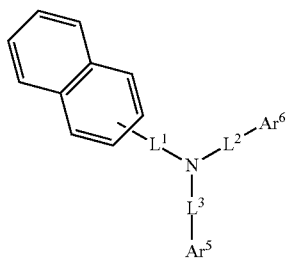

<Formula (9)>

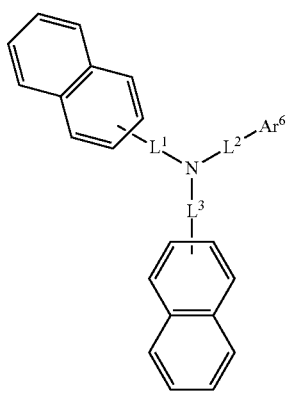

<Formula (10)>

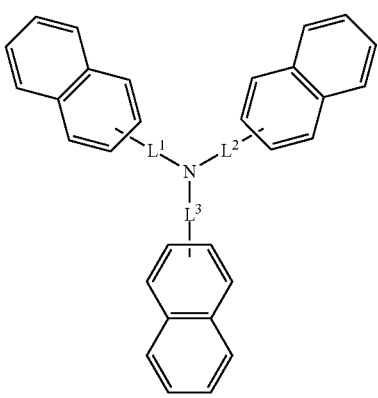

<Formula (11)>

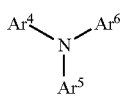

-continued

<Formula (12)>

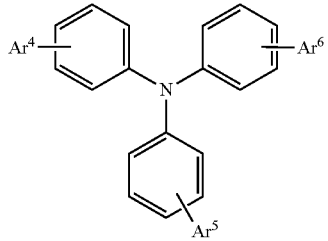

Hereinafter, $L^1$, $L^2$, $L^3$, $Ar^4$, $Ar^5$ as, and $Ar^6$ are the same $L^1$, $L^2$, $L^3$, $Ar^4$, $Ar^5$ and $Ar^6$ defined by the Formula (1).

In another specific example of the present invention, $L^1$, $L^2$, $L^3$, and $L^5$ in the compounds represented by the Formula (1) and the Formula (2) may be a single bond, or $L^1$, $L^2$, $L^3$, $L^4$ and $L^5$ may be represented by the following Formulas.

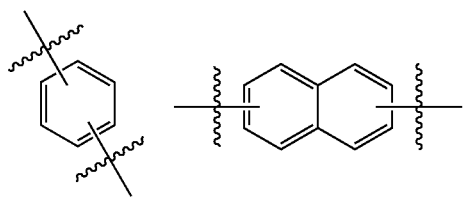

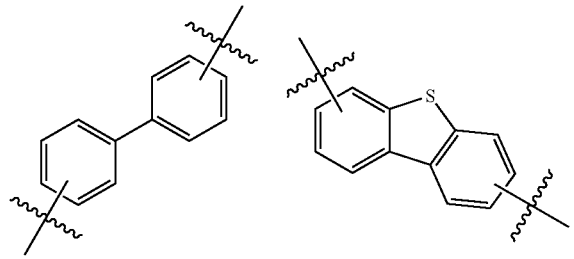

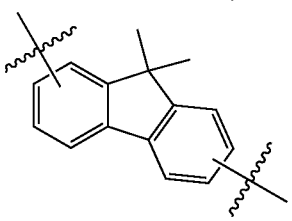

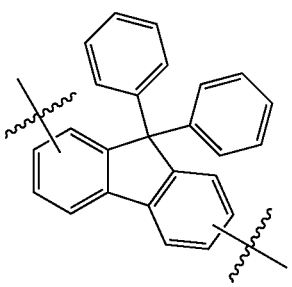

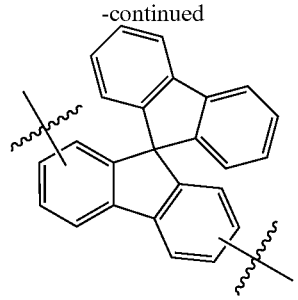
In another specific example of the present invention, the compounds represented by the formula (1) of the hole transport layer or by the Formulas (3) to (7) further specified the formula (1) may be one of the following compounds.
1-1
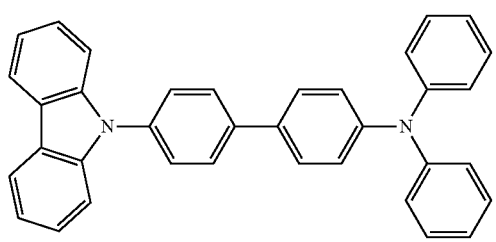
1-2
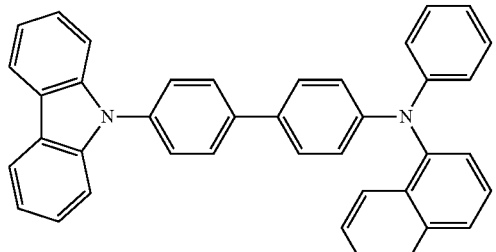
1-3
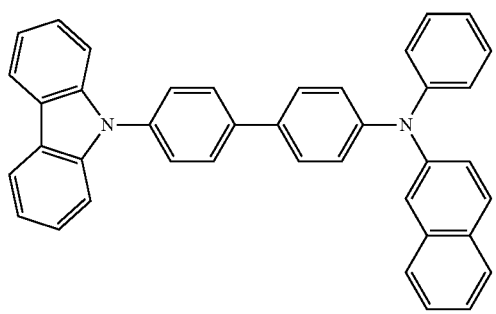
1-4
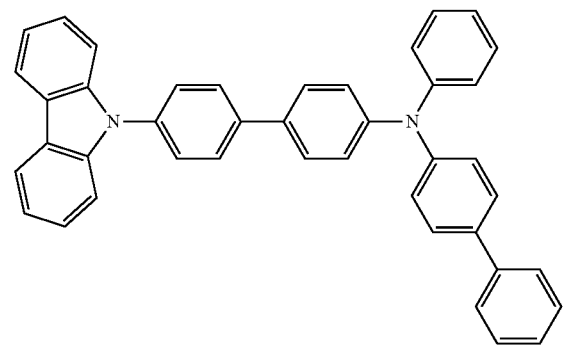
1-5
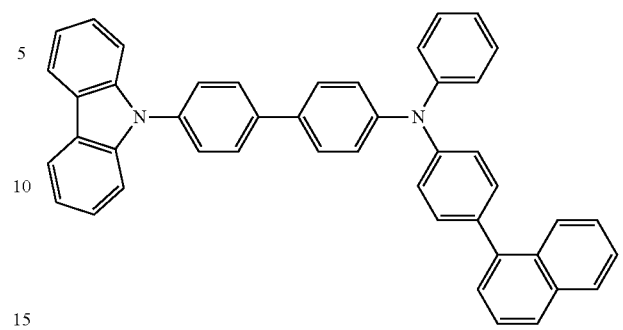
1-6
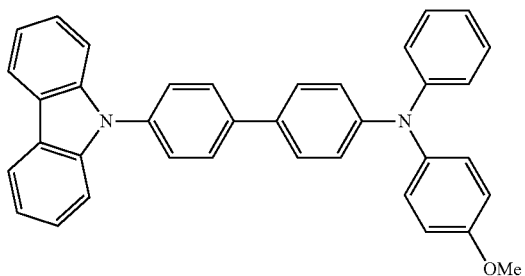
1-7
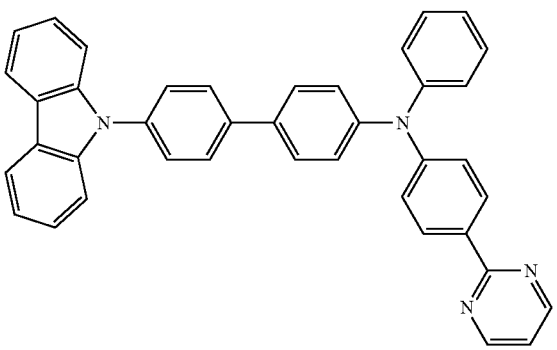
1-8
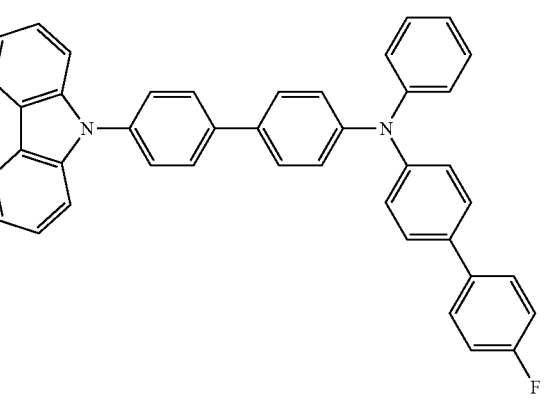

1-9
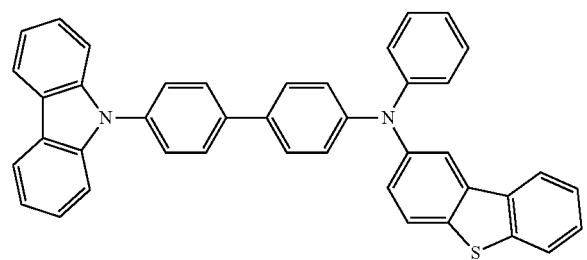
1-10
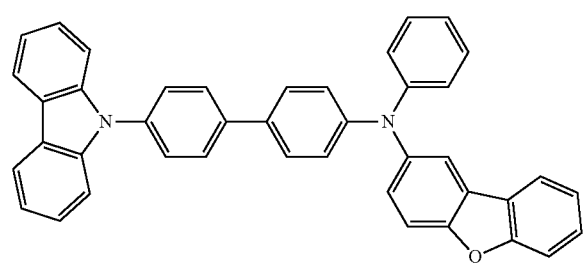
1-11
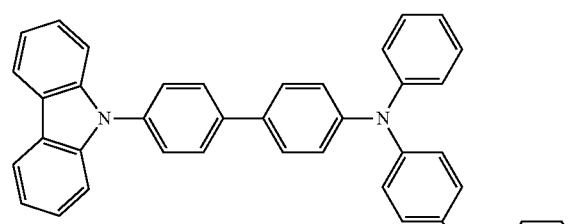
1-12
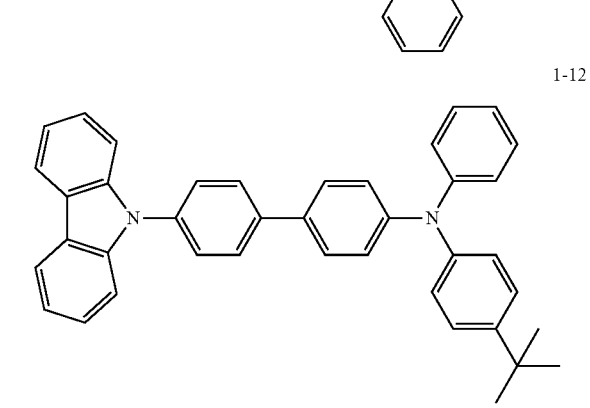
1-13
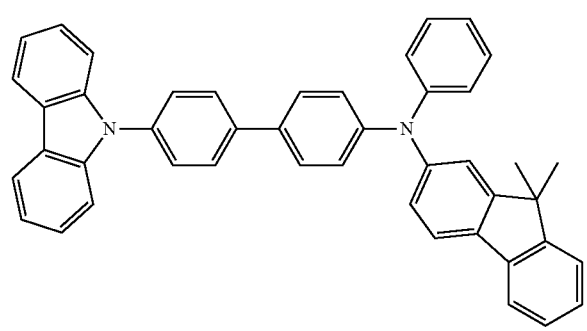
1-14
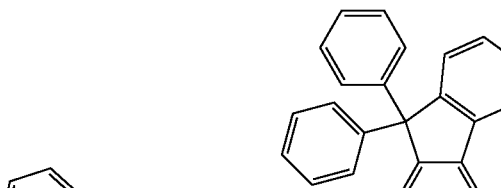
1-15
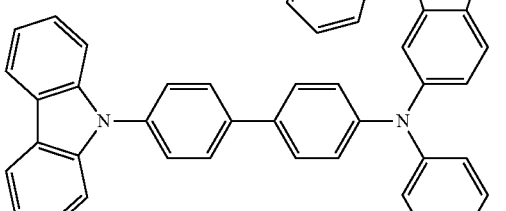
1-16
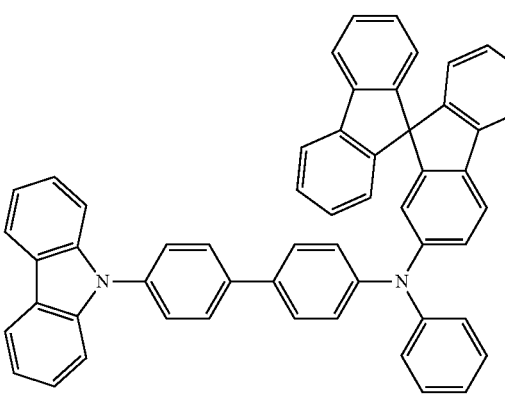
1-17
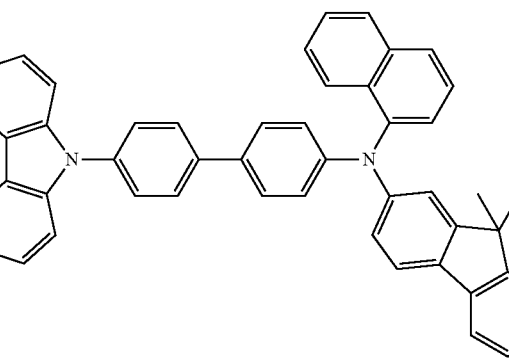
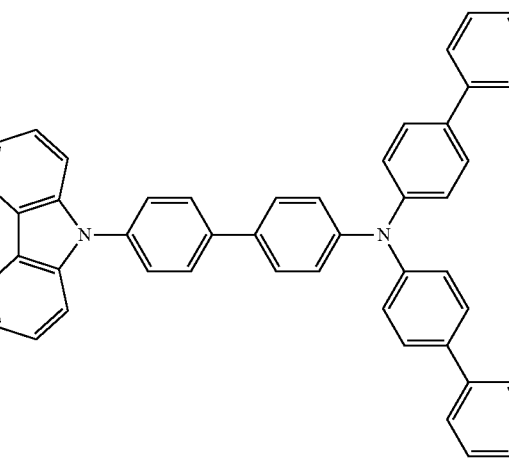

1-18
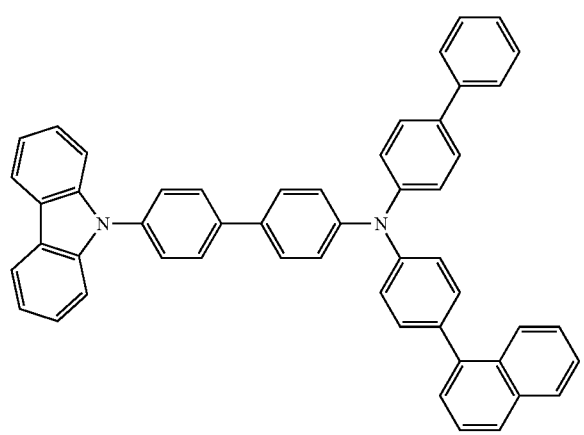
1-19
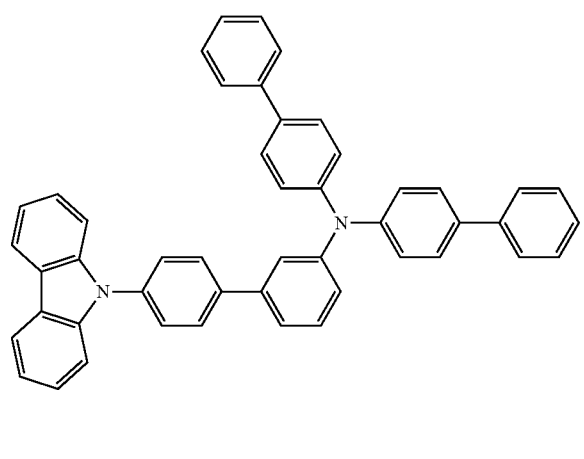
1-20
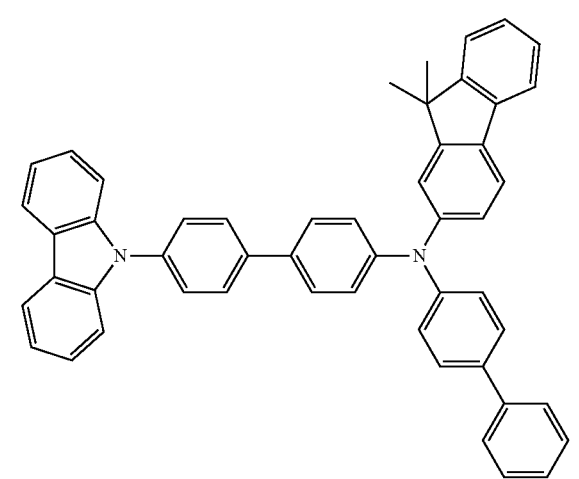
1-21
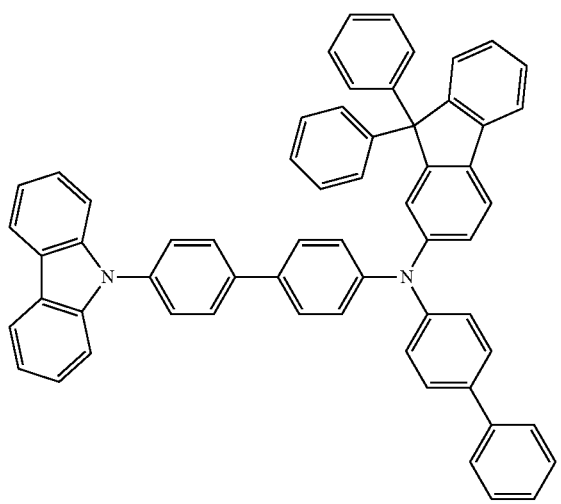
1-22
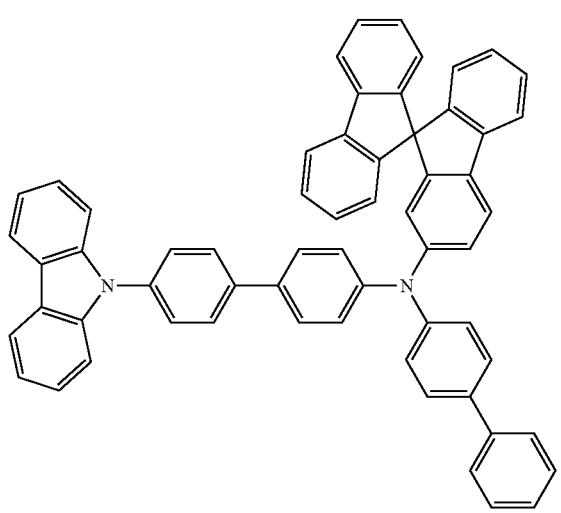
1-23
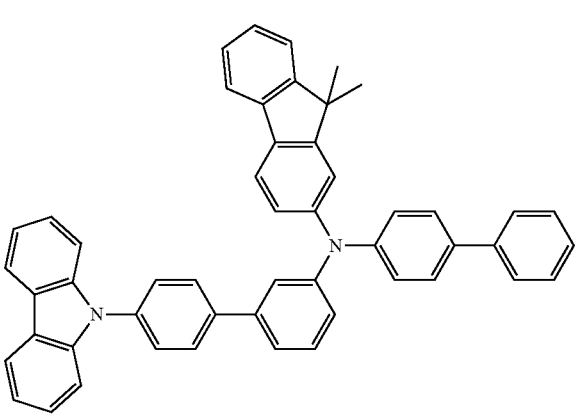

1-24
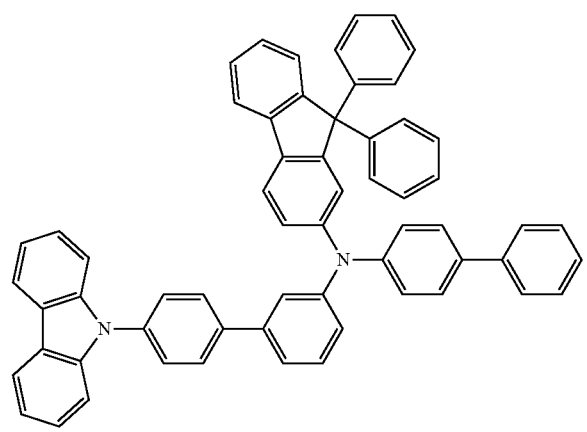
1-25
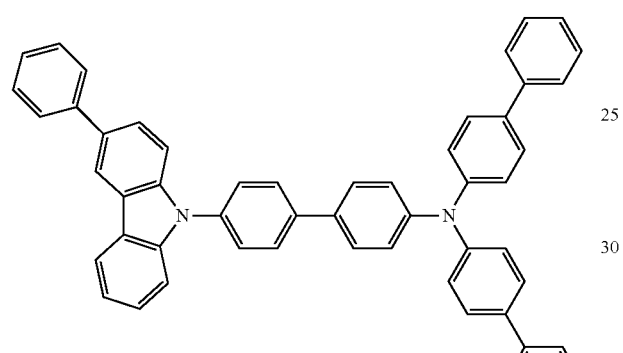
1-26
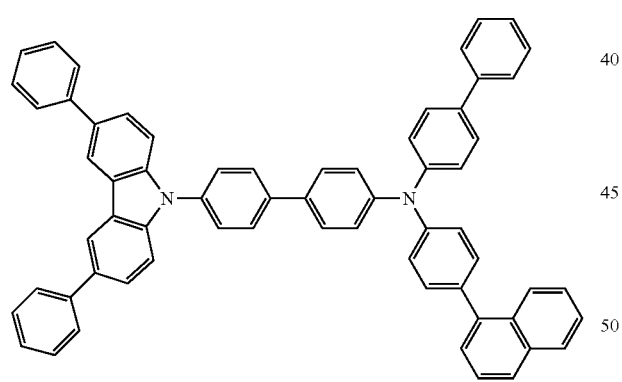
1-27
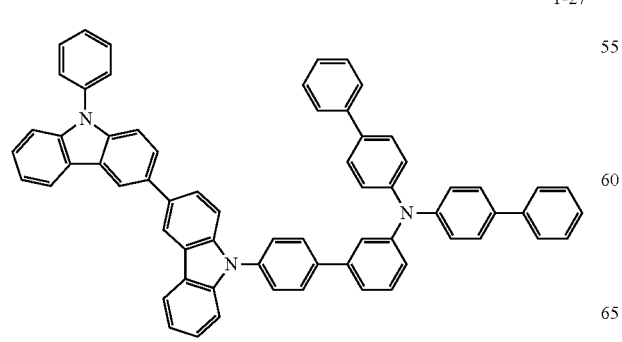
1-28
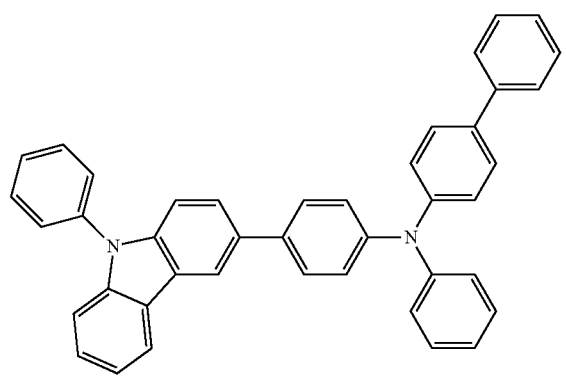
1-29
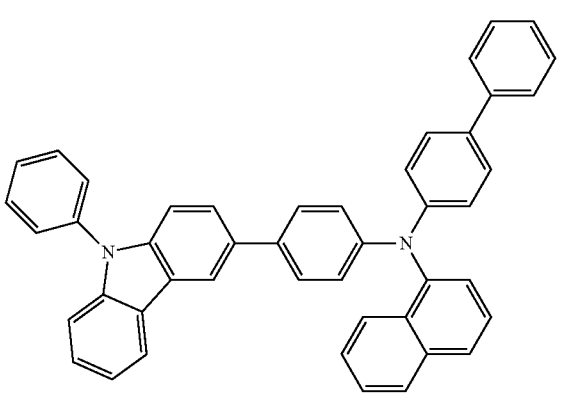
1-30
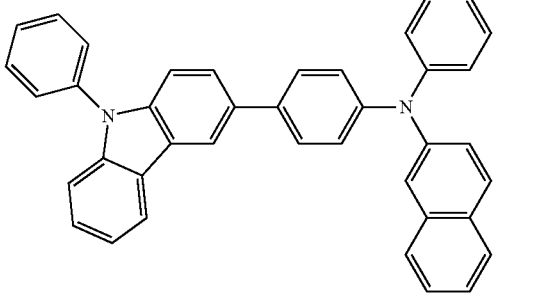

1-31
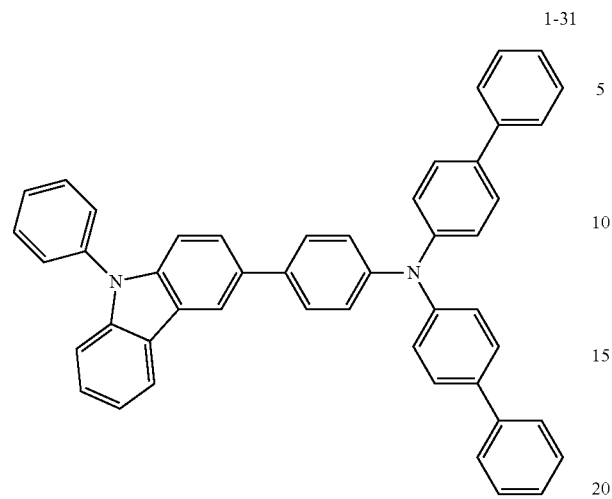
1-32
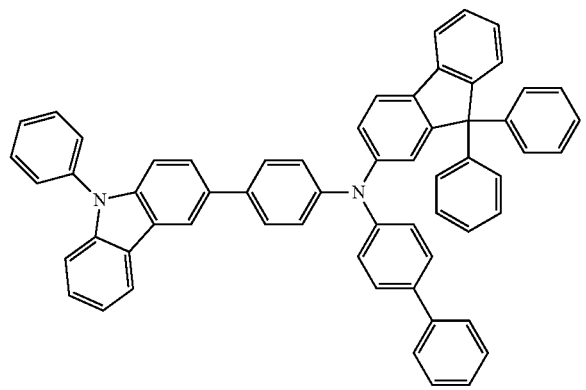
1-33
1-34
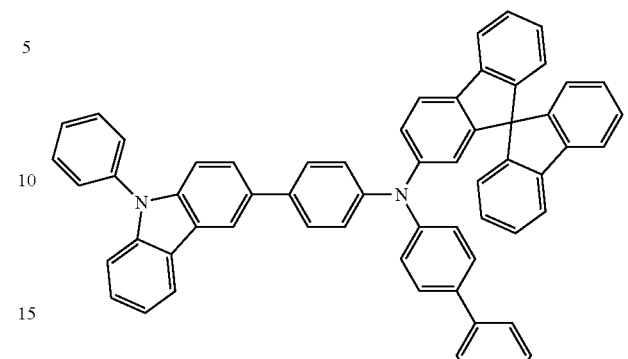
1-35
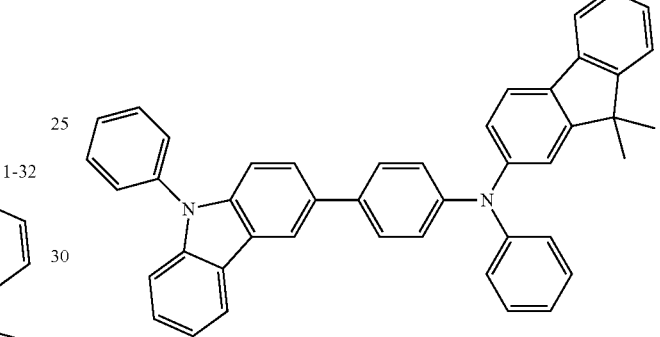
1-36
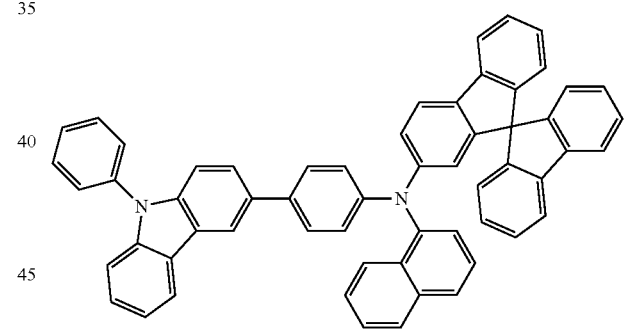
1-37
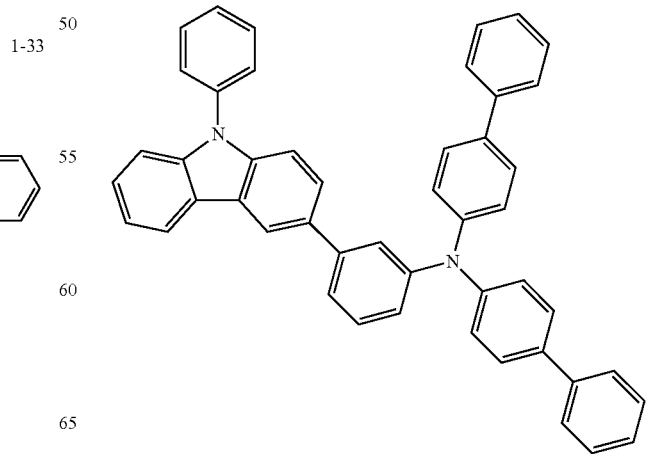

1-38
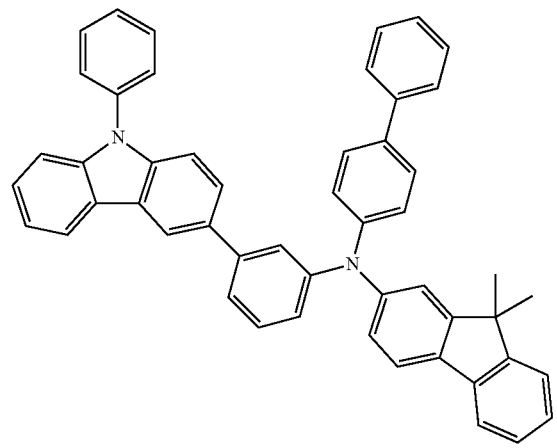
1-39
1-40
1-41
1-42
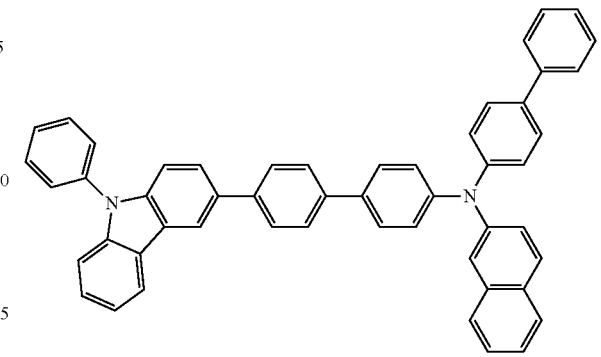
1-43
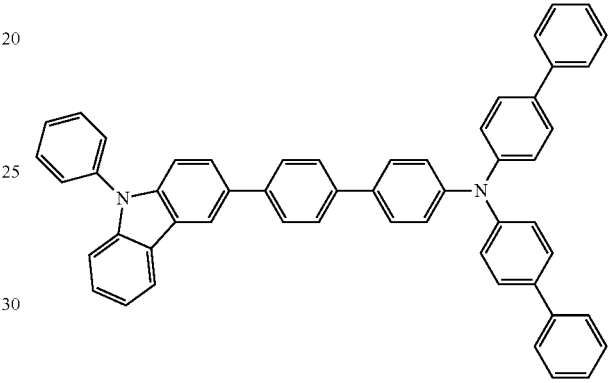
1-44
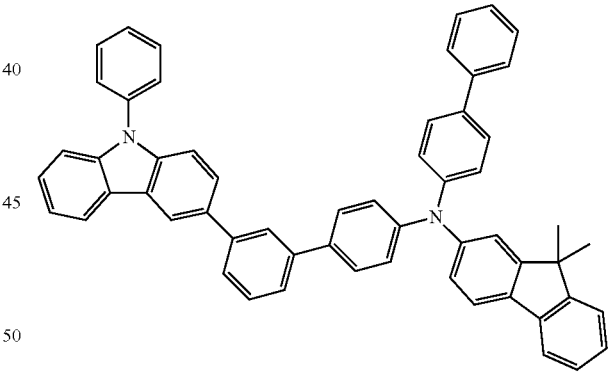
1-45
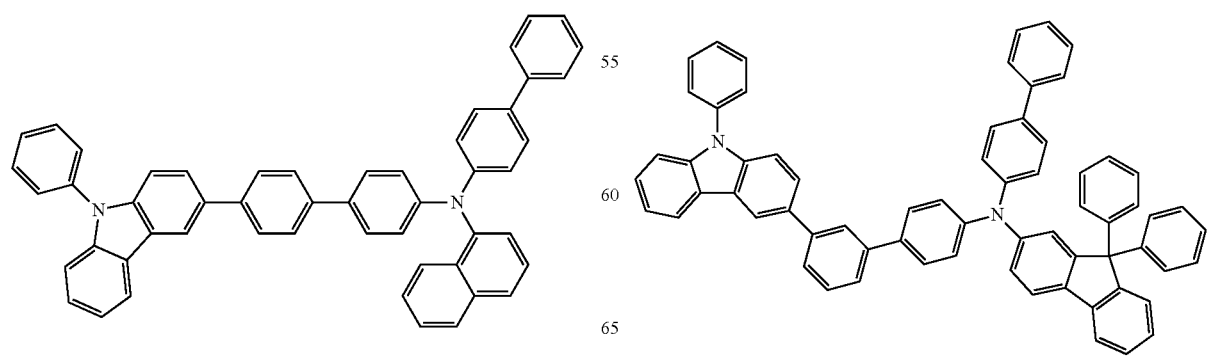

1-46
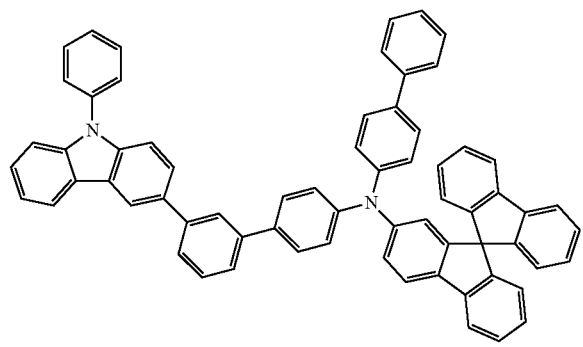
1-47
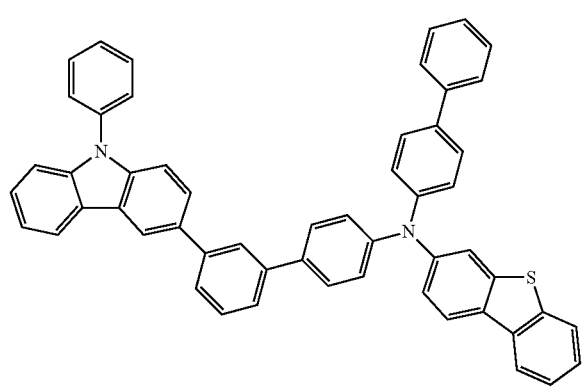
1-48
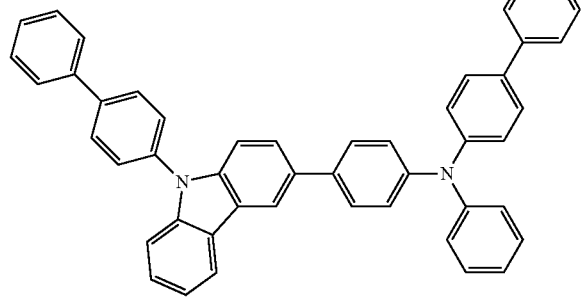
1-49
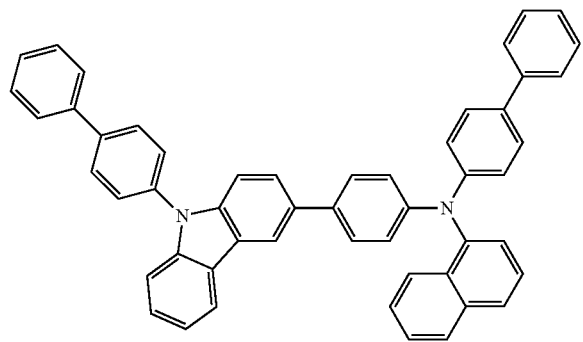
1-50
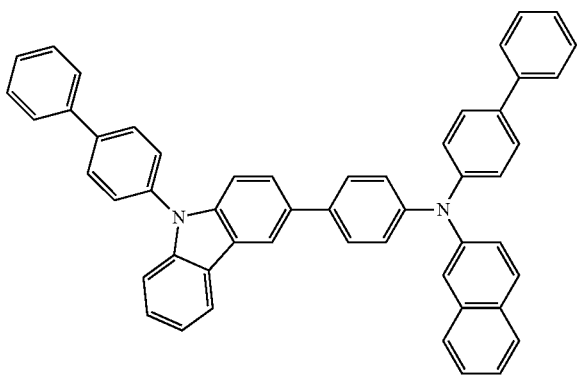
1-51
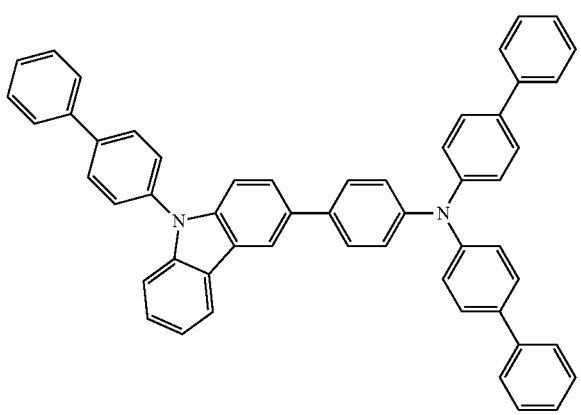
1-52
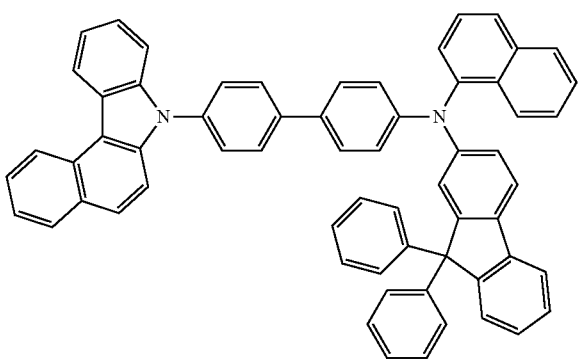
1-53
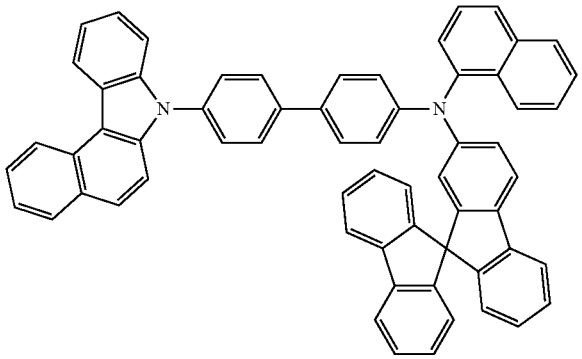

-continued
1-54
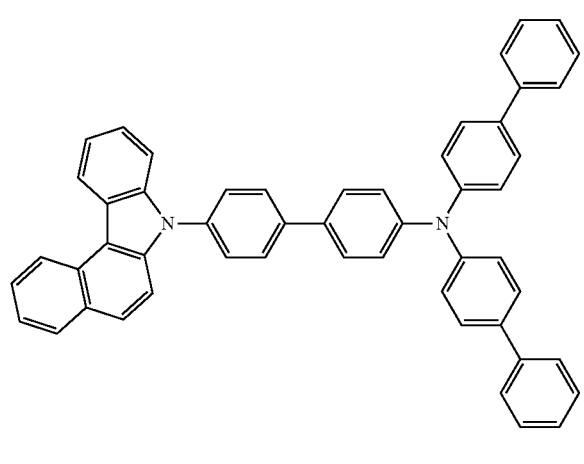
1-55
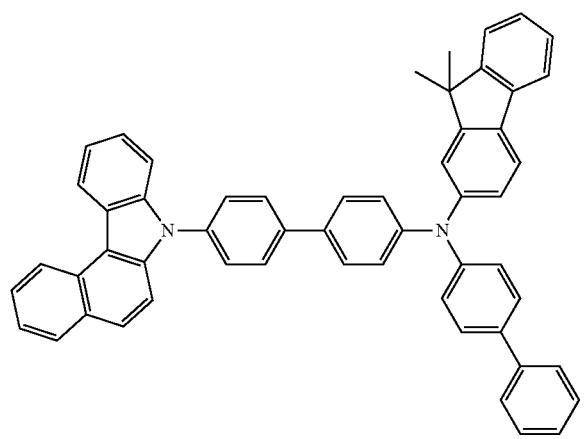
1-56
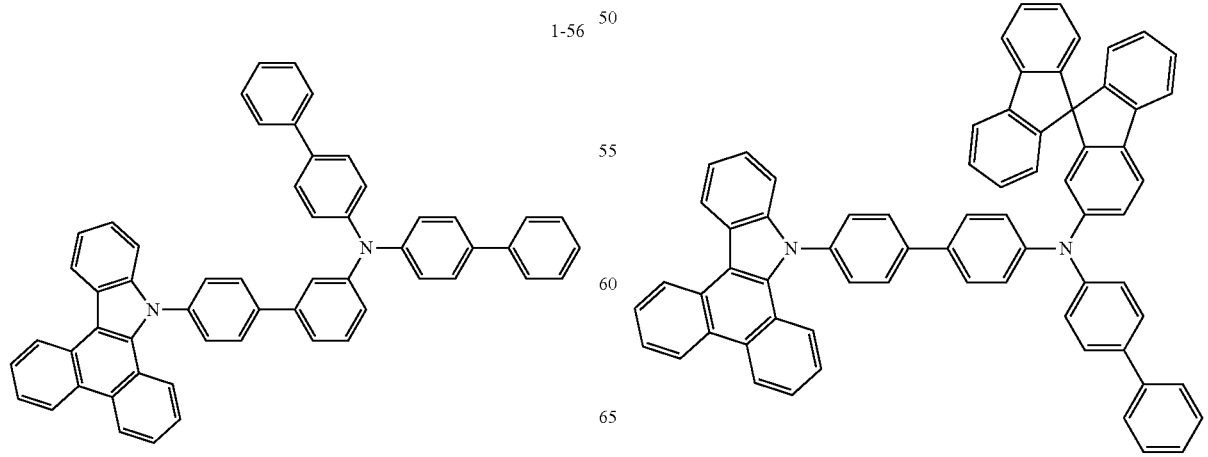
1-57
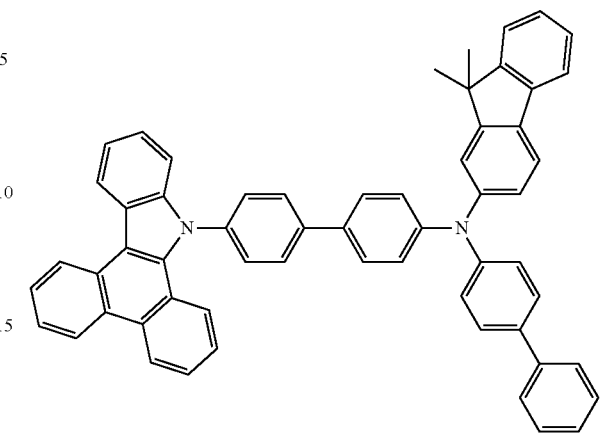
1-58
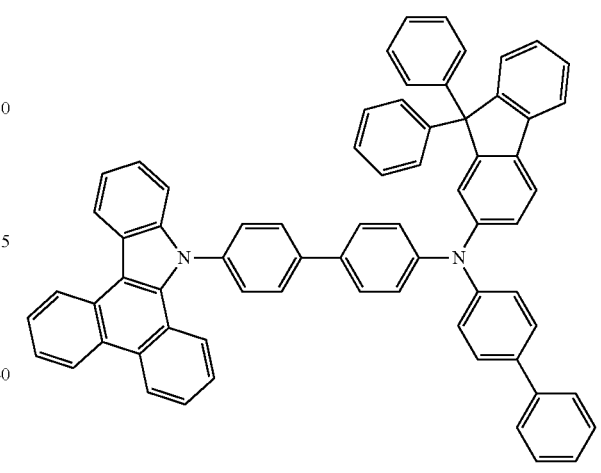

1-60
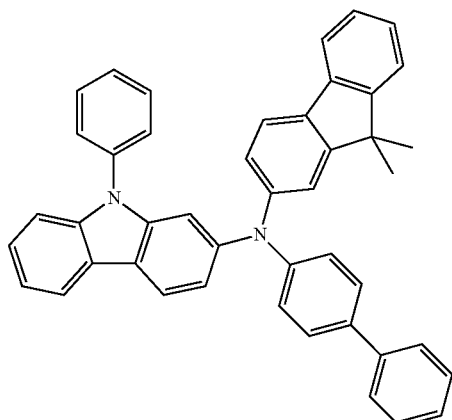
1-61
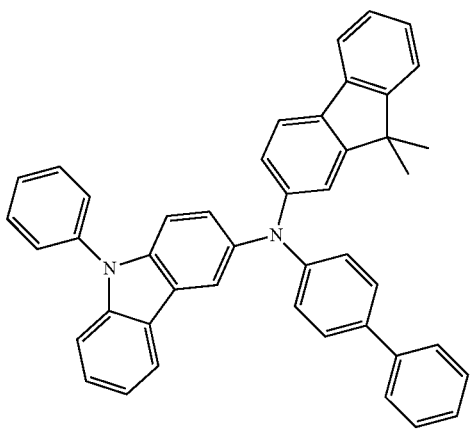
1-62
1-63
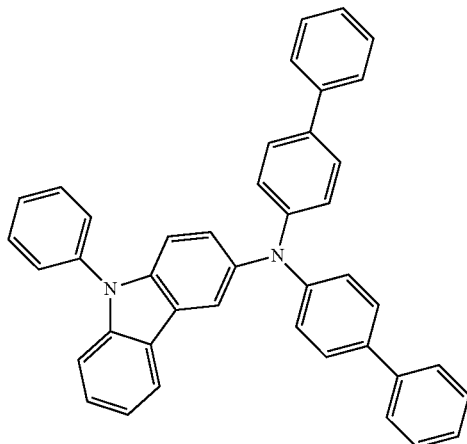
1-64
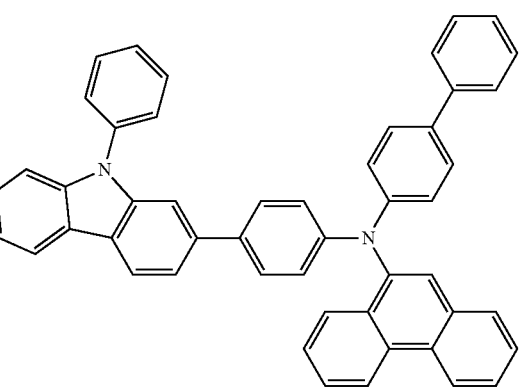
1-65
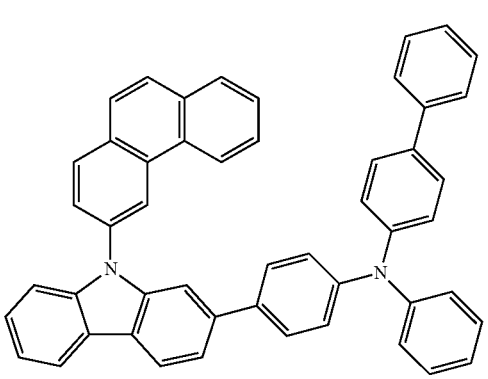

1-66
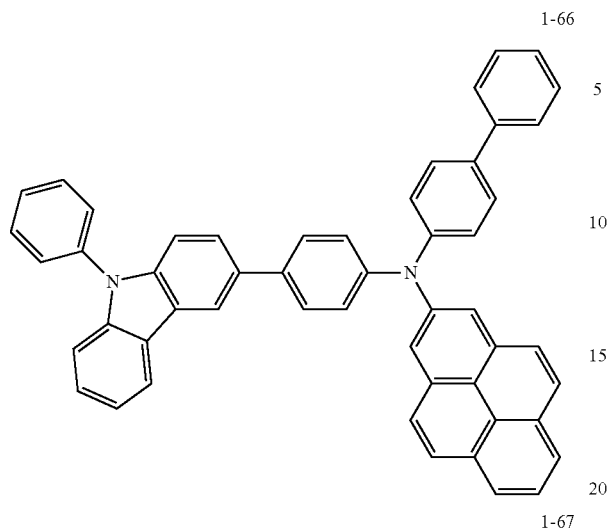
1-67
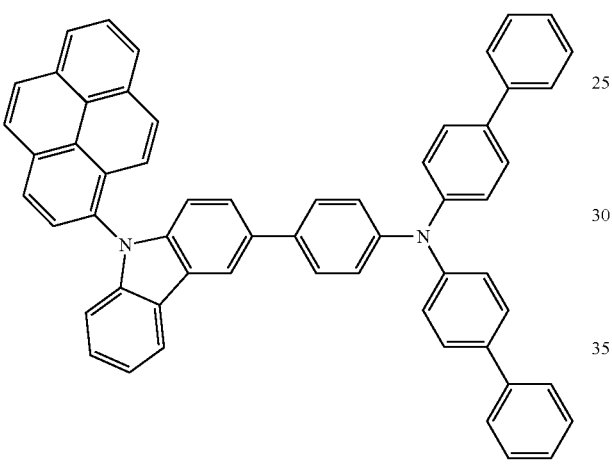
2-2
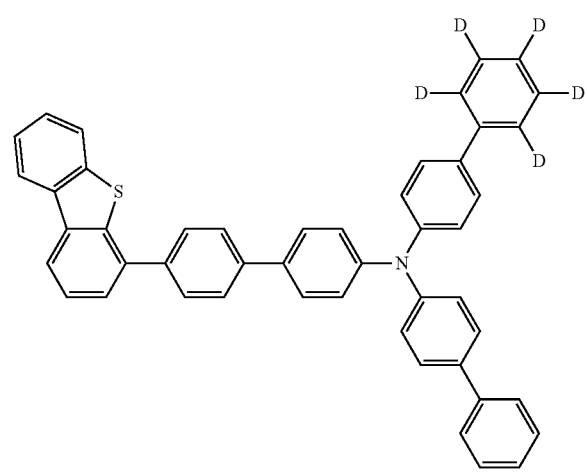
2-3
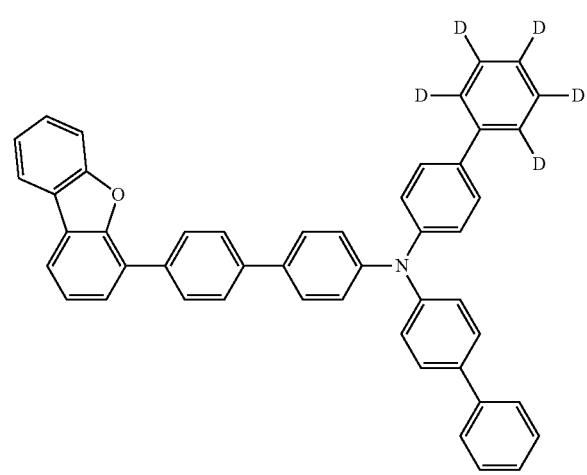
In another specific example of the present invention, the compounds represented by the formula (2) of the emitting-auxiliary layer or by the formulas (8) to (12) further specified the formula (2) may be one of the following compounds.
2-1
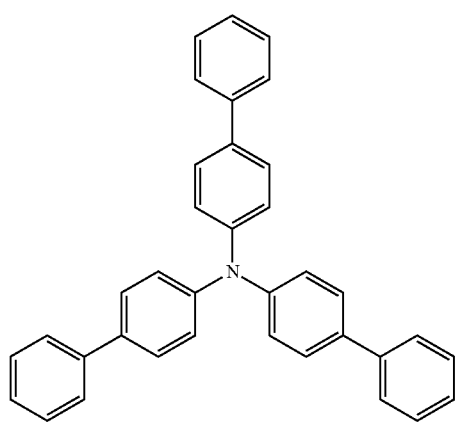
2-4
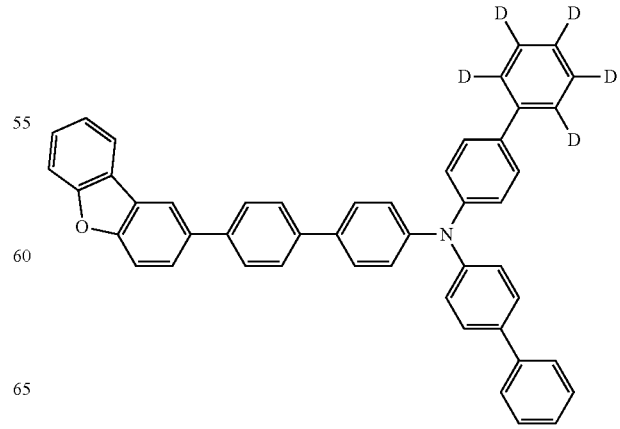

2-5
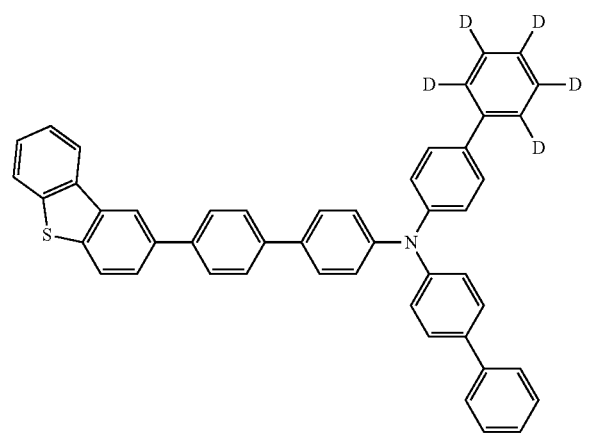
2-8
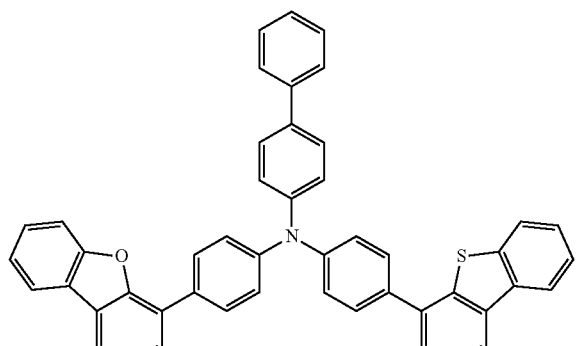
2-6
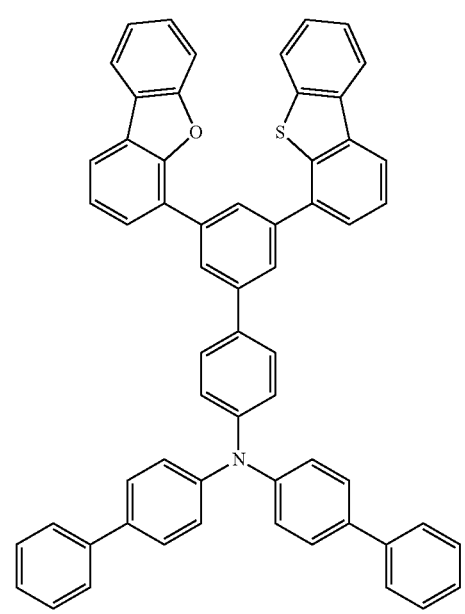
2-9
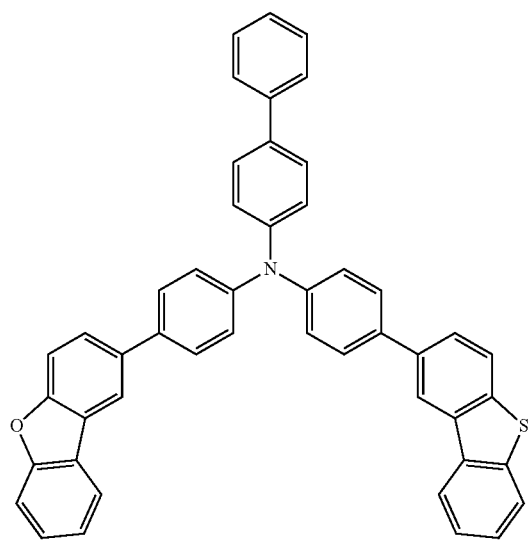
2-7
2-10
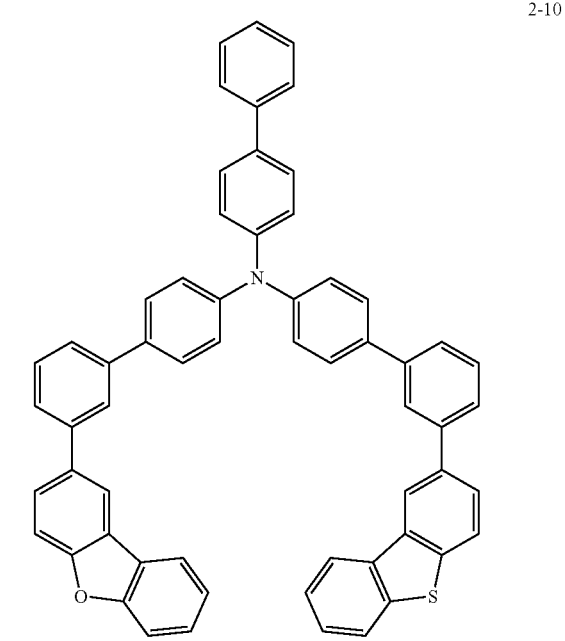

US 10,991,888 B2
2-11
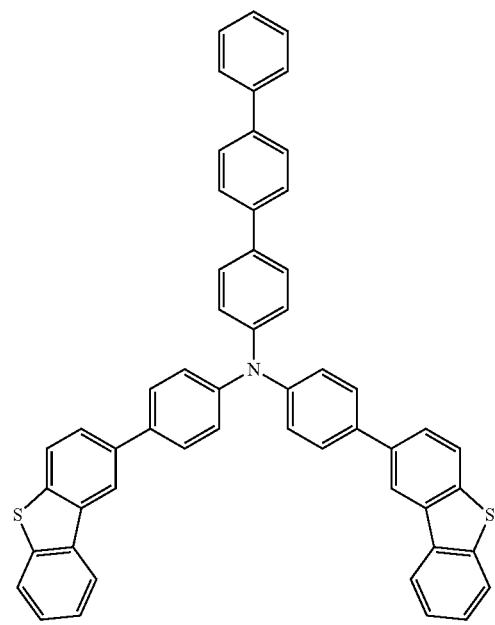
2-14
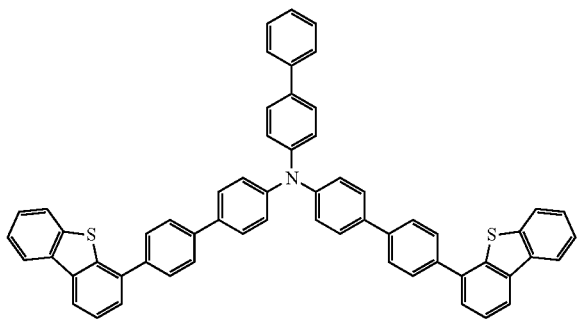
2-15
2-12
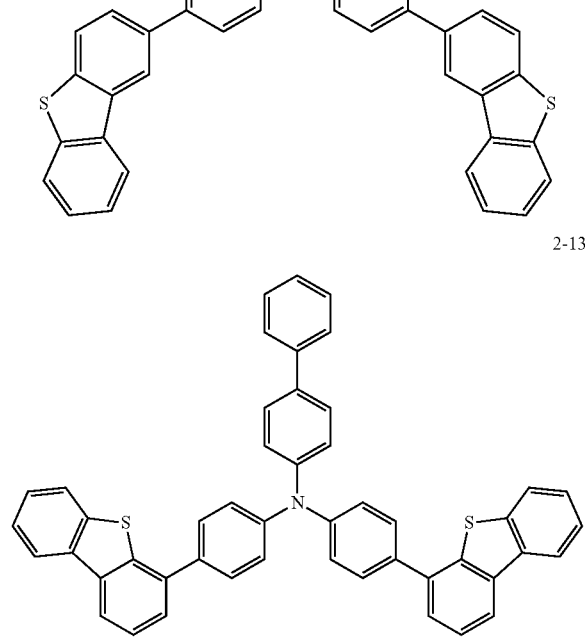
2-13
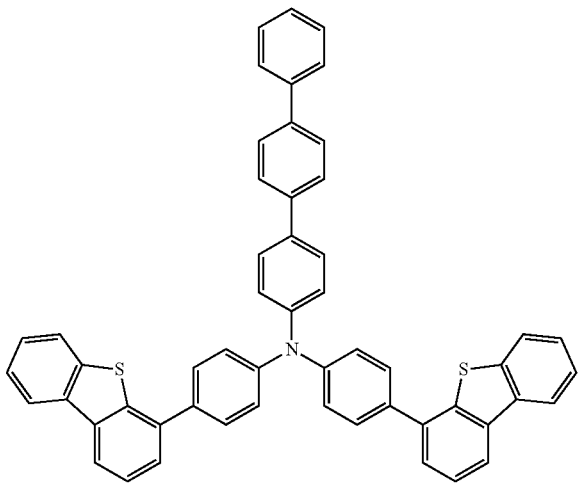
2-16

2-17
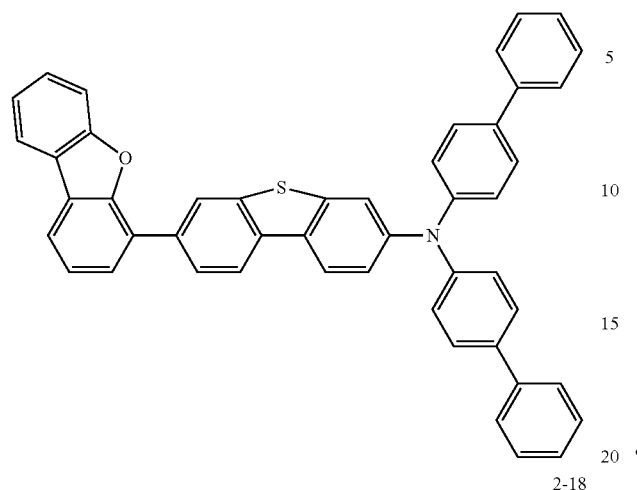
2-18
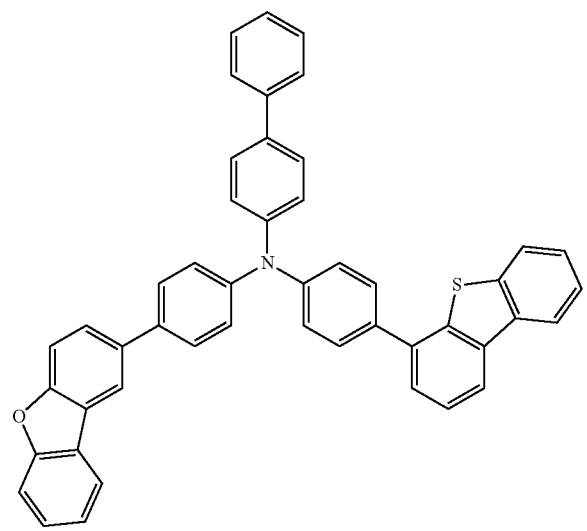
2-19
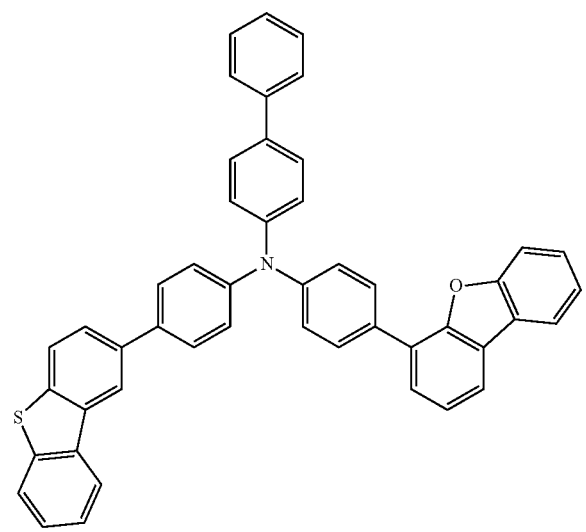
2-20
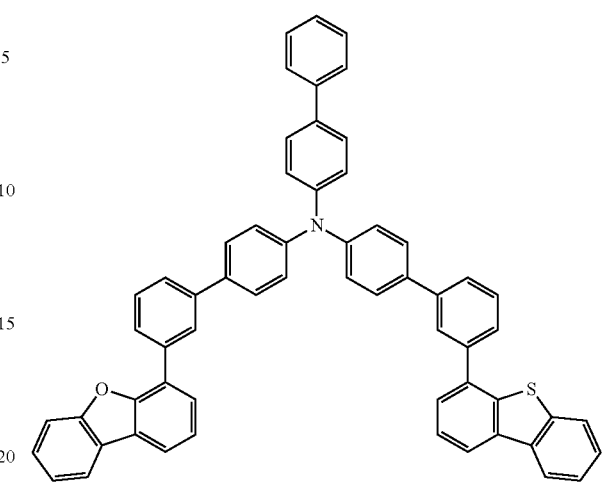
2-21
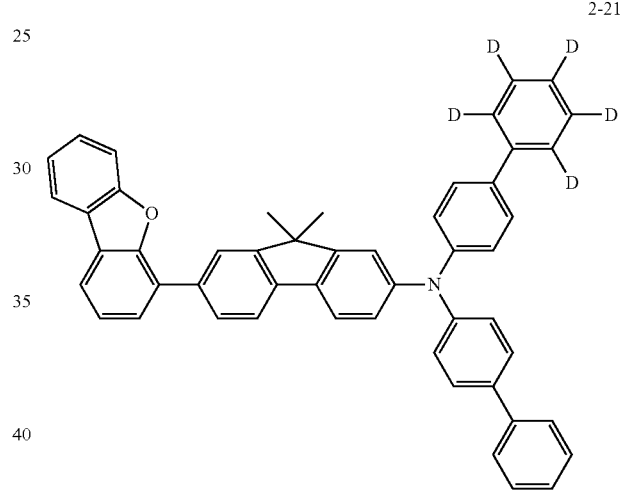
2-22
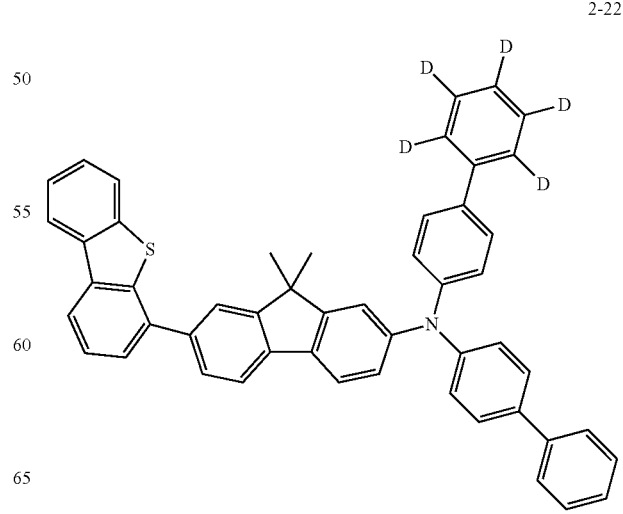

2-23
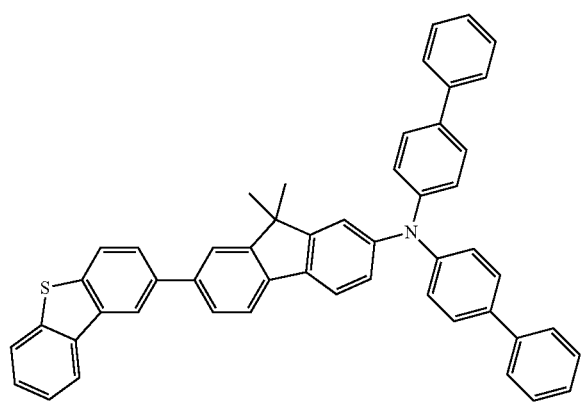
2-24
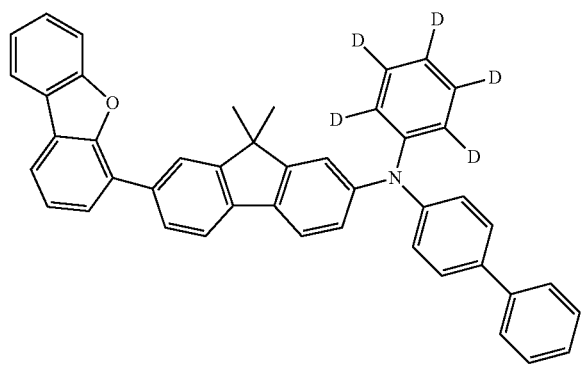
2-25
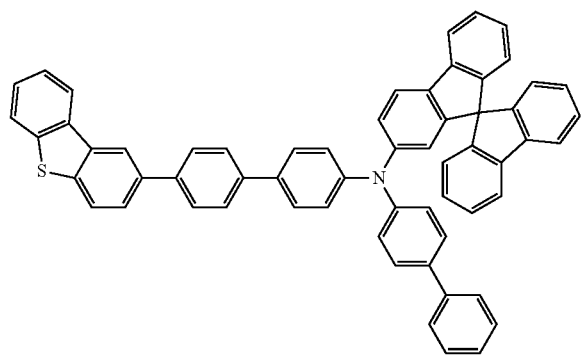
2-26
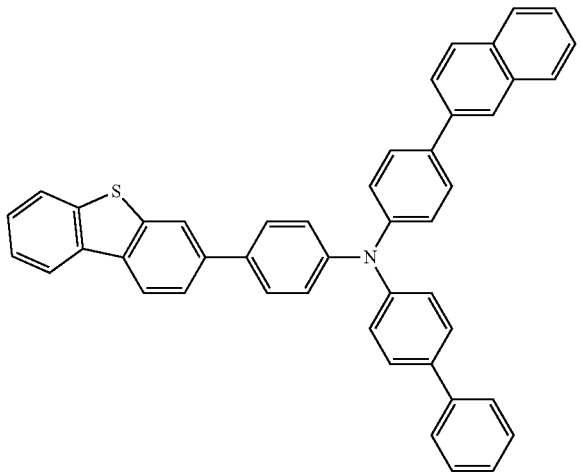
2-27
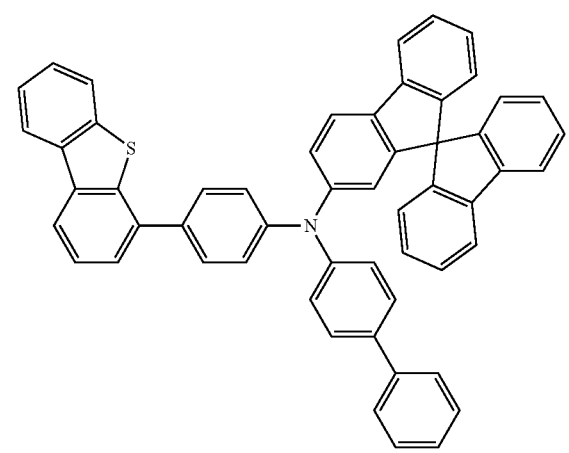
2-28
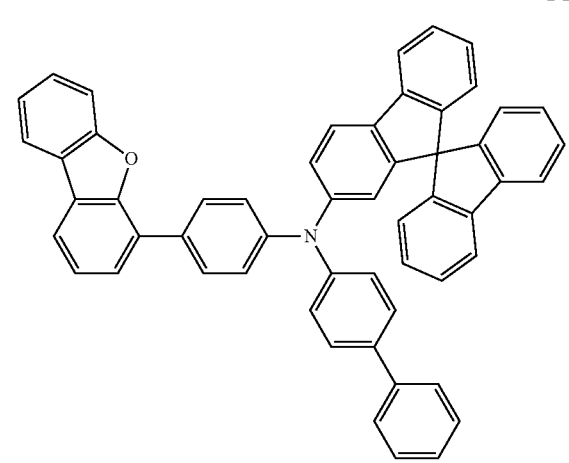

2-29
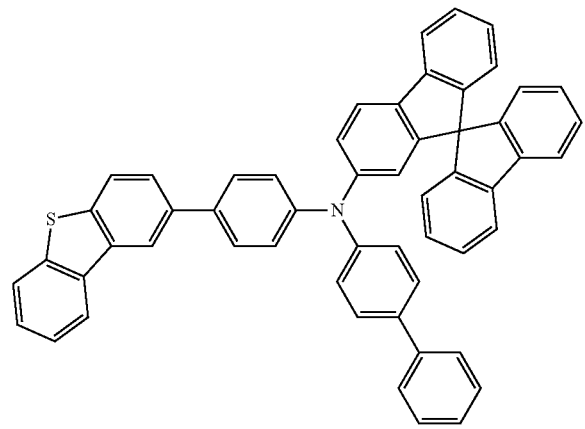
2-32
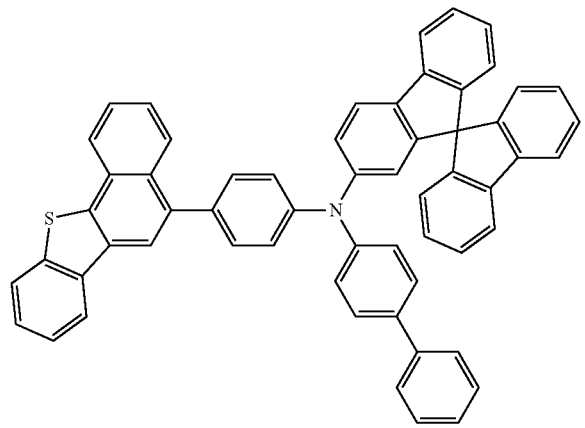
2-30
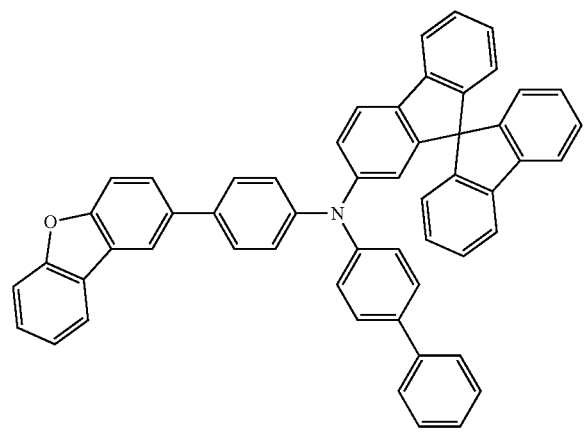
2-33
2-31
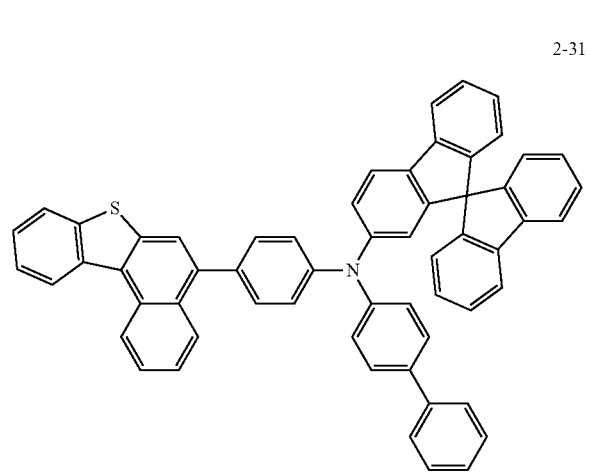
2-34
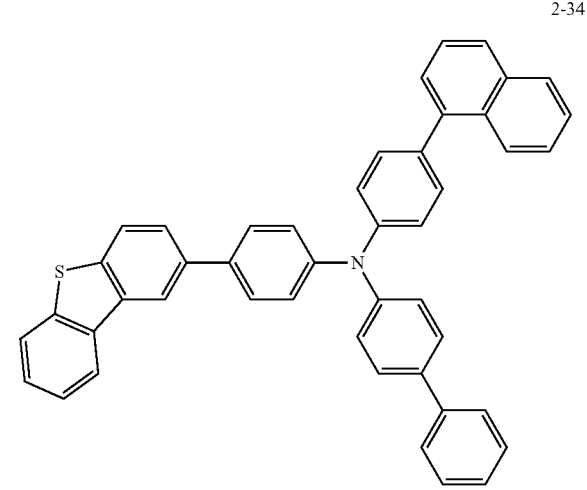

2-35
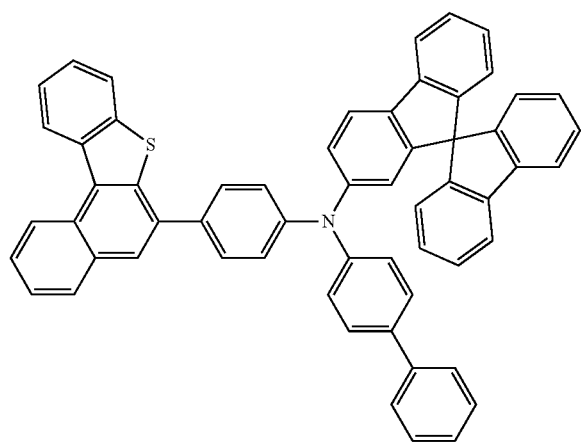
2-38
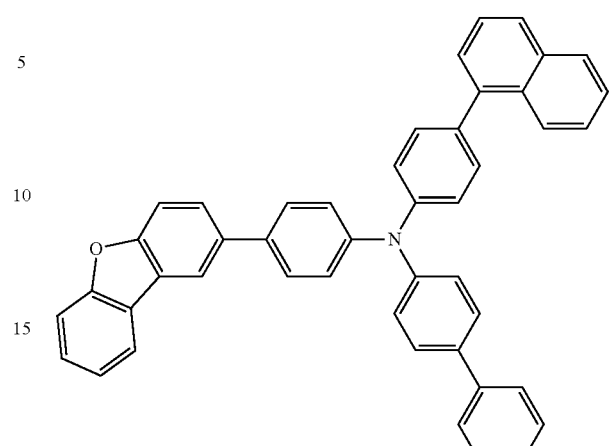
2-36
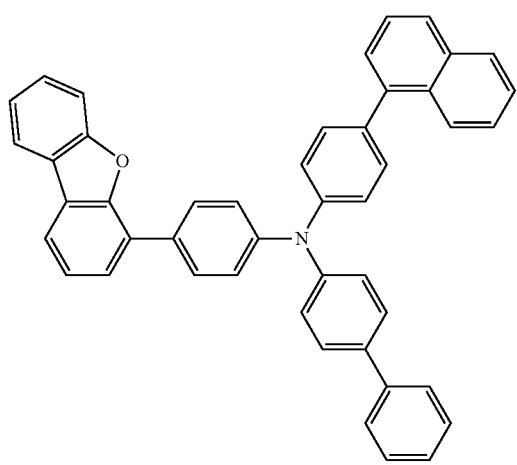
2-39
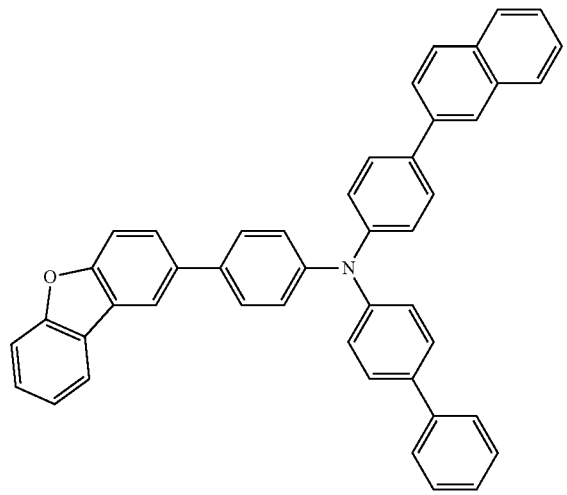
2-37
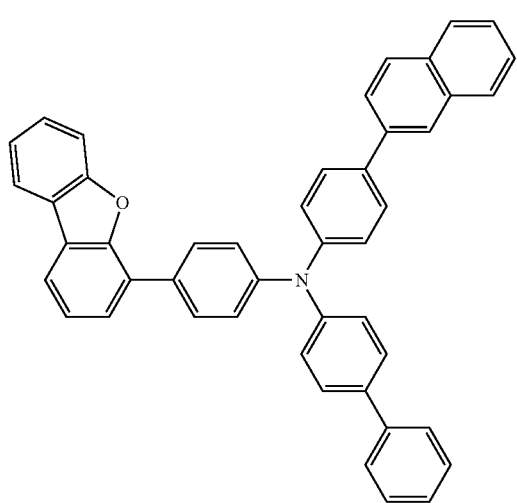
2-40
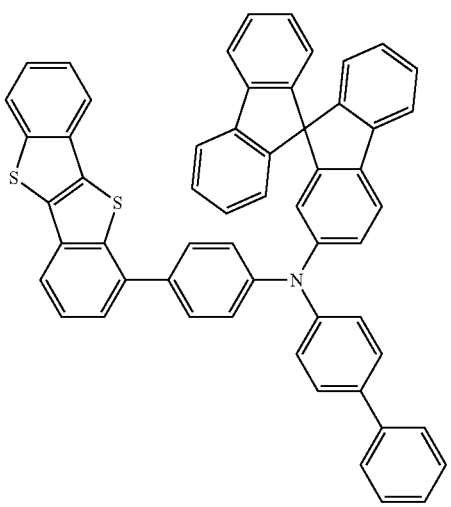

2-41
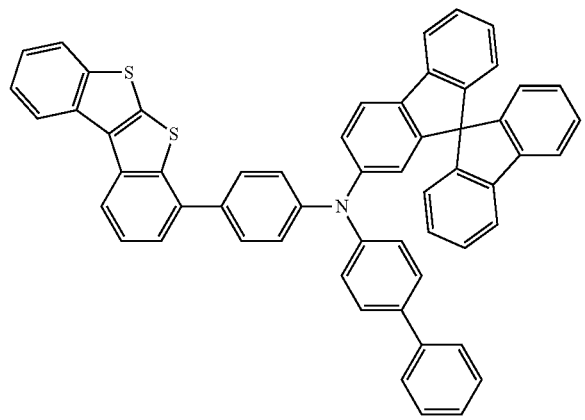
2-42
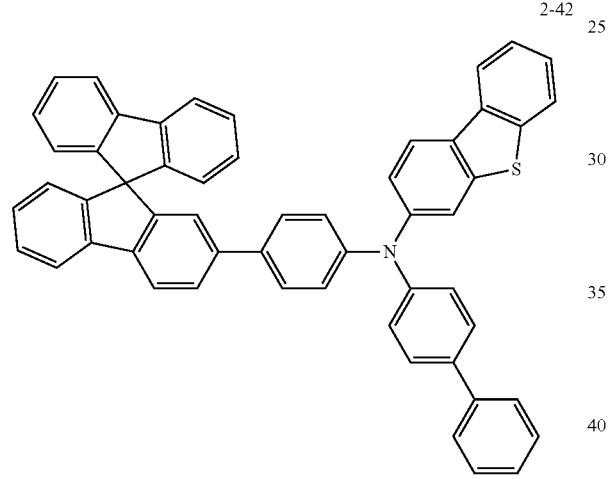
2-43
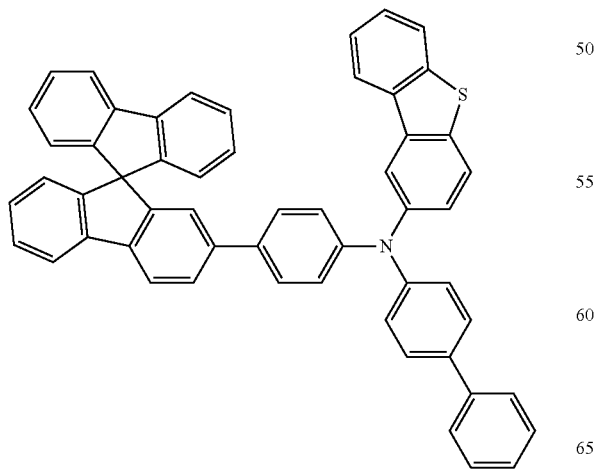
2-44
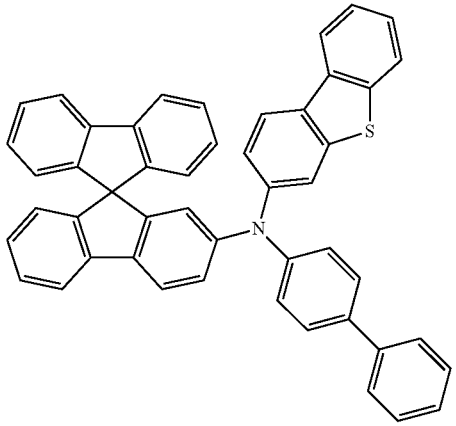
2-45
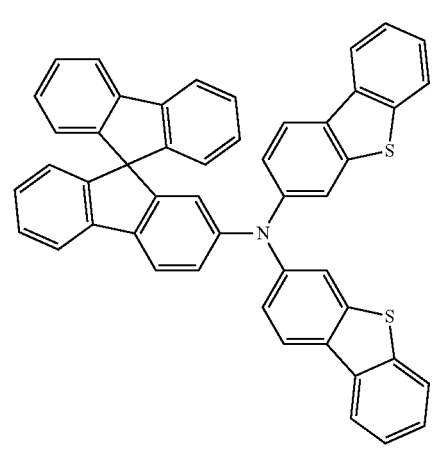
2-46
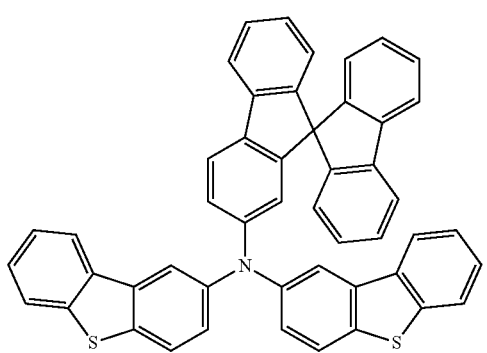
2-47

2-48
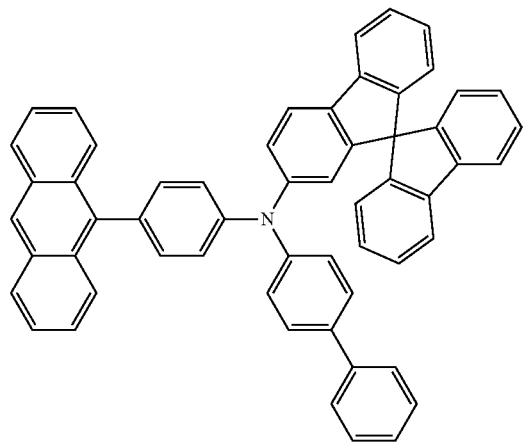
2-51
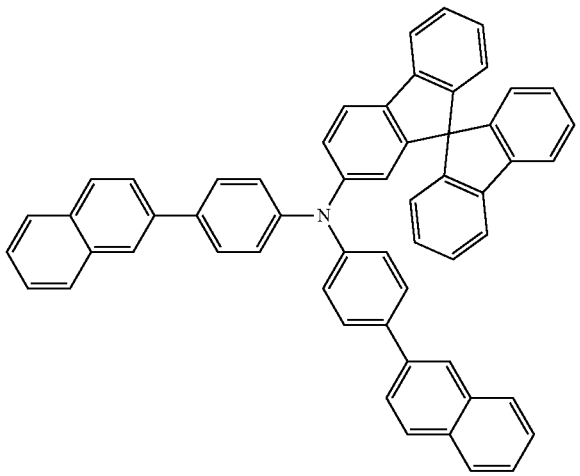
2-49
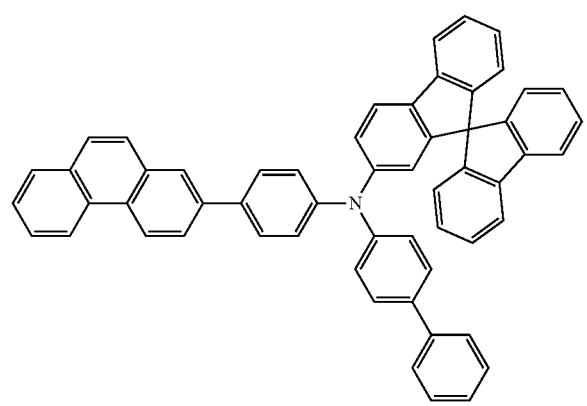
2-52
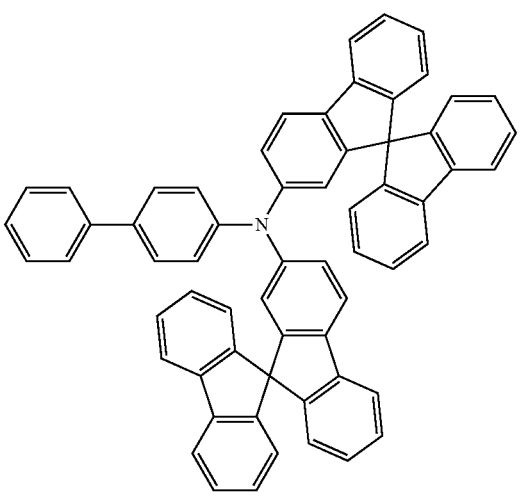
2-50
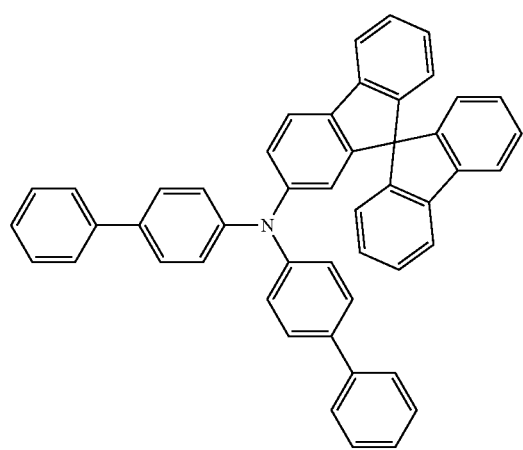
2-53
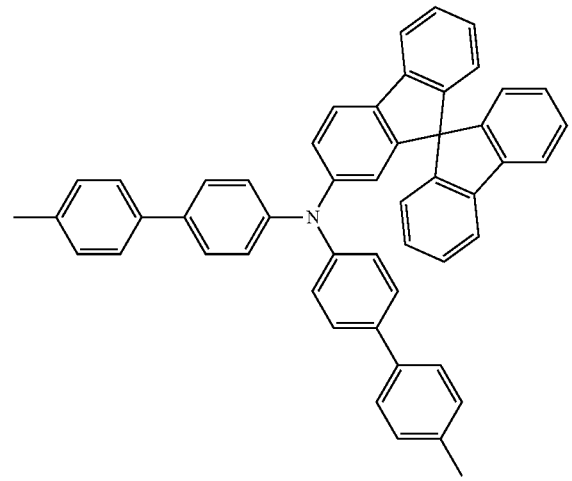

2-54
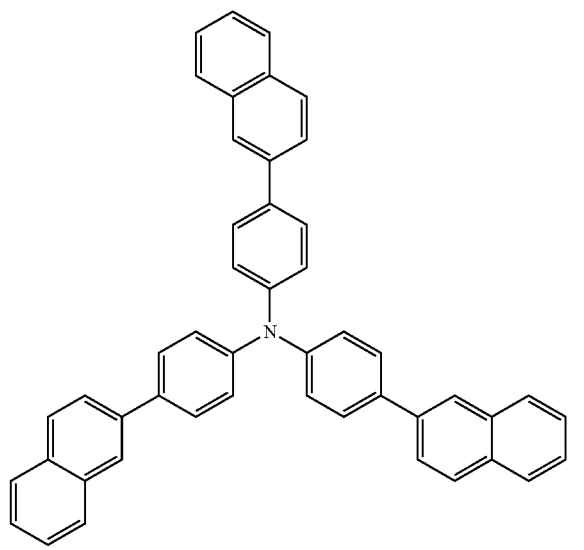
2-55
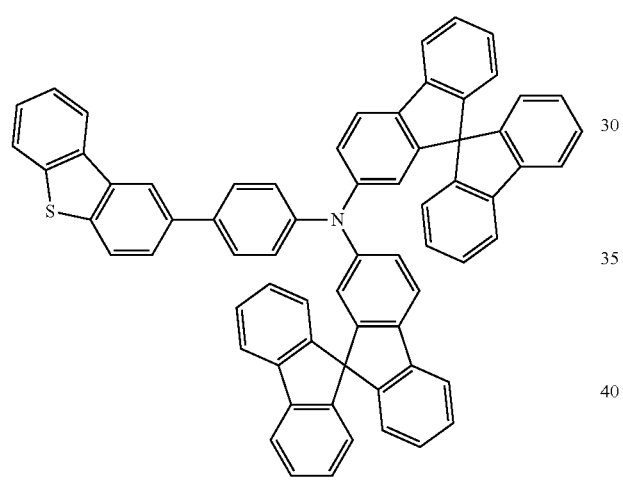
2-56
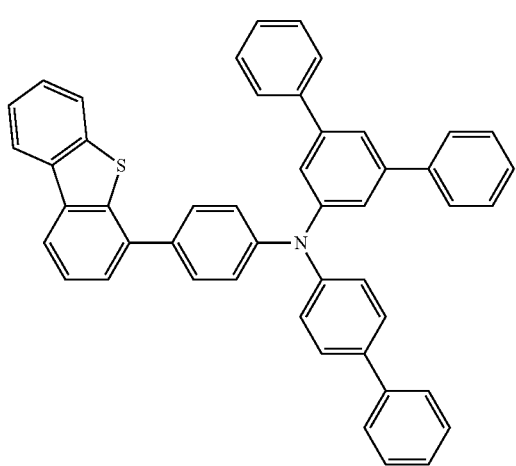
2-57
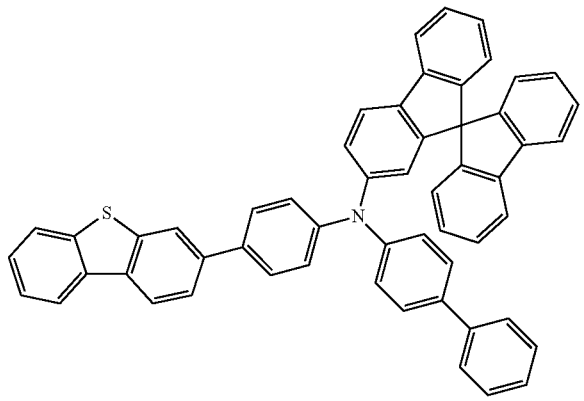
2-58
2-59
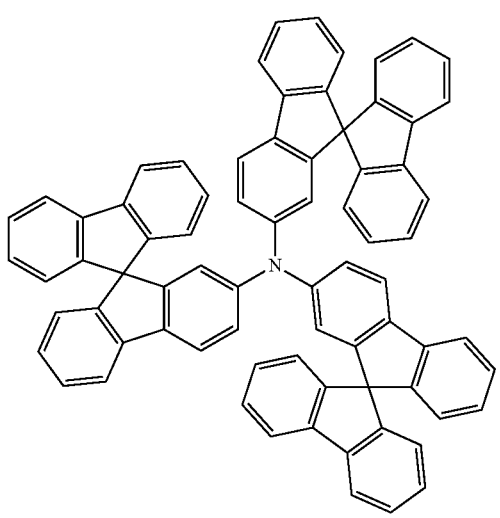

2-60
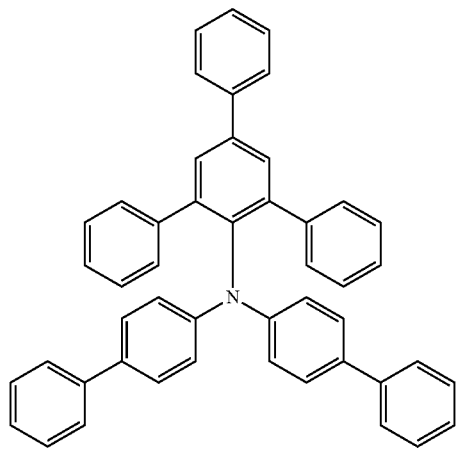
2-63
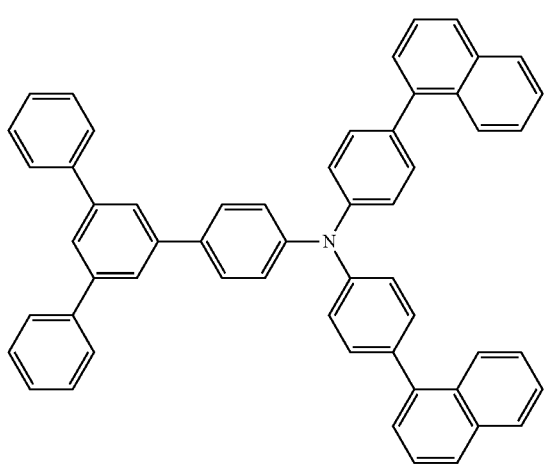
2-61
2-64
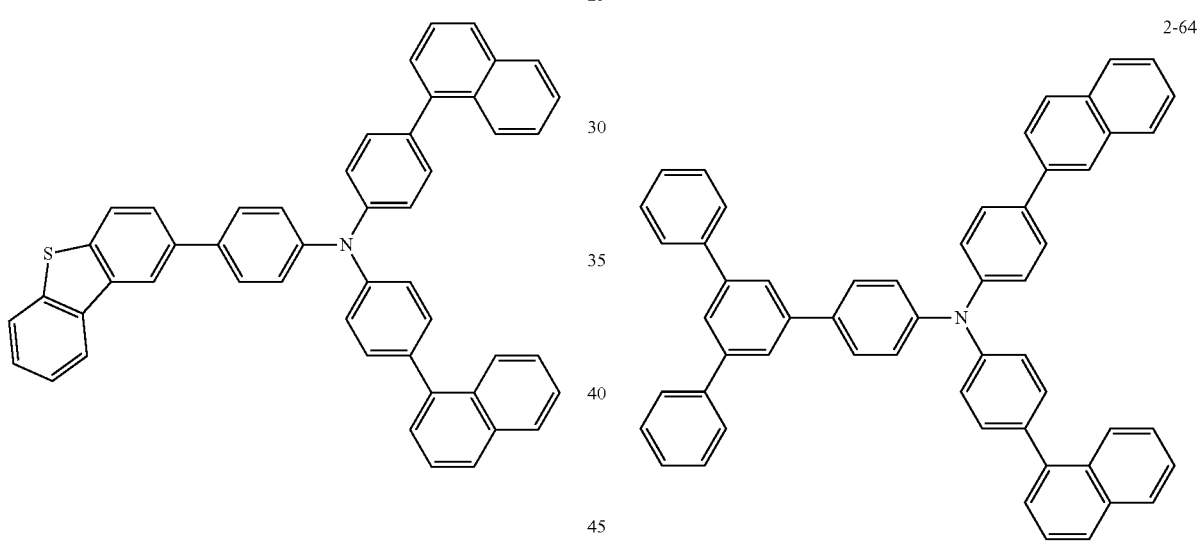
2-62
2-65
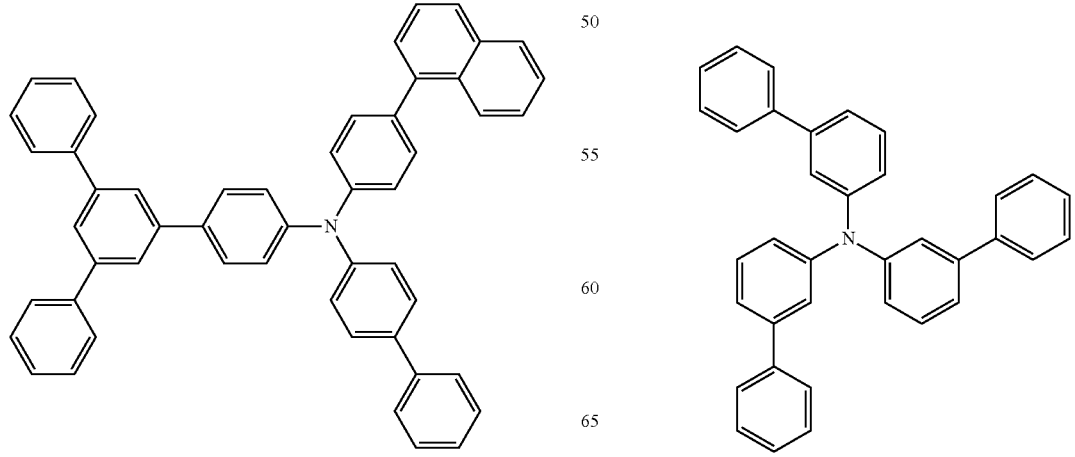

2-66
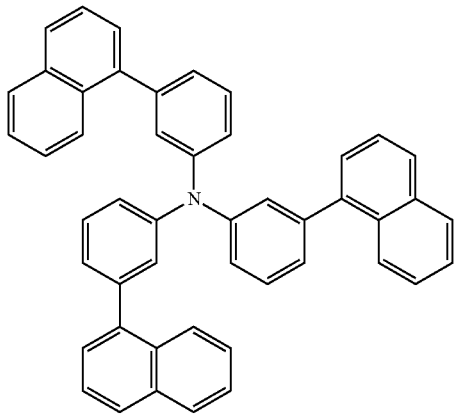

2-67
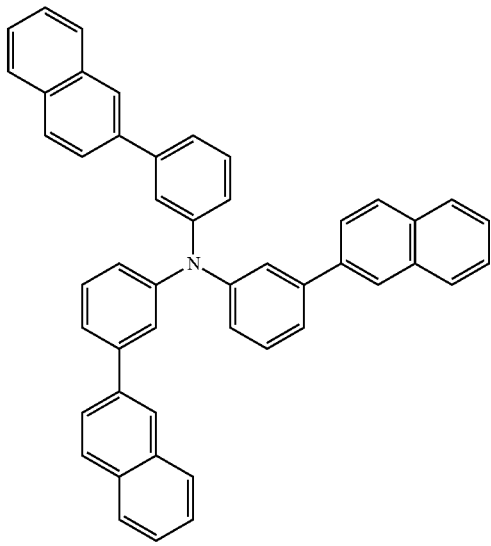

2-68
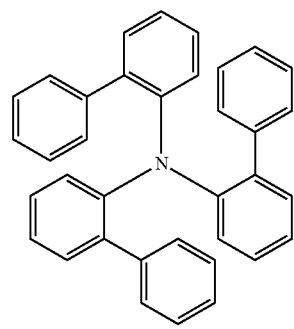

In another specific example of the present invention, the emitting auxiliary layer includes one of the compounds in which $Ar^4$ to $Ar^6$ in the formula (2) are aryl groups of $C_6$ to $C_{60}$.

In another specific example of the present invention, the emitting auxiliary layer provides one of compounds in which at least one of $Ar^4$ to $Ar^6$ of the Formula (2) is $C_6$-$C_{60}$ heteroaryl group.

In another specific example of the present invention, the hole transport layer comprises a compound represented Formula (3) and the emitting auxiliary layer comprises a compound represented Formula (2).

In another specific example of the present invention, the hole transport layer comprises a compound represented Formula (4) and the emitting auxiliary layer comprises a compound represented Formula (2).

In another specific example of the present invention, the emitting auxiliary layer comprises a mixture of two or more compounds represented by the formula (2).

In another specific example of the present invention, an electronic element includes a display device comprising the organic electronic element; and a control part driving the display apparatus characterized in that an organic electronic element comprising a first electrode, a second electrode, and an organic layer formed between the first electrode and the second electrode, wherein the organic material layer includes an emitting auxiliary layer formed between the first electrode and the emitting layer, and a hole transport layer formed between the first electrode and the emitting auxiliary layer, wherein the hole transport layer contains a compound represented by the following Formula (1), and the emitting auxiliary layer contains a compound represented by the following Formula (2).

In another specific example of the present invention, the organic electronic element may be at least one of an OLED, an organic solar cell, an organic photo conductor (OPC), Organic transistor (organic TFT) and an element for monochromic or white illumination.

Hereinafter, the synthesis examples of the compounds represented by the formulas (1) and (2) comprised in the organic electronic element of the present invention and the preparation examples of an organic electronic element of the present invention will be described in detail by way of examples. However, the following examples are only for illustrative purposes and are not intended to limit the following examples of the invention.

Synthesis Example 1

The final product 1 represented by Formula (1) according to the present invention can be synthesized by reaction between Sub 1 or Sub 2 and Sub 3 as illustrated in the following Reaction Scheme 1.

<Reaction Scheme 1>

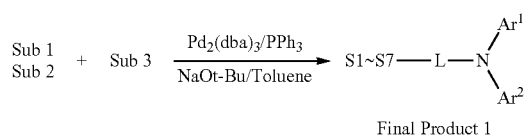

Final Product 1

*L is $L^4$ or $L^5$ defined as the Formula (1-a), and the Formula (1-b).

1. Synthesis Example of Sub 1

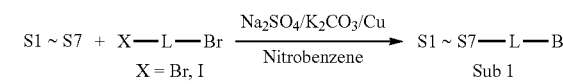

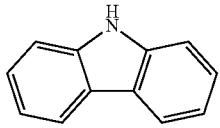

-continued

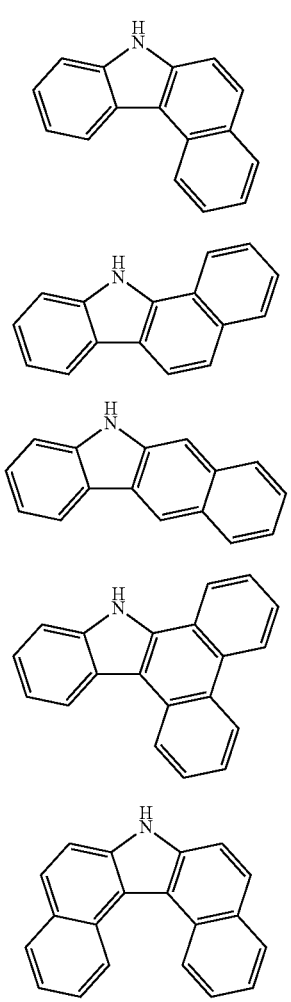

1) Synthesis Example of Sub 1-1-1(L=biphenyl)

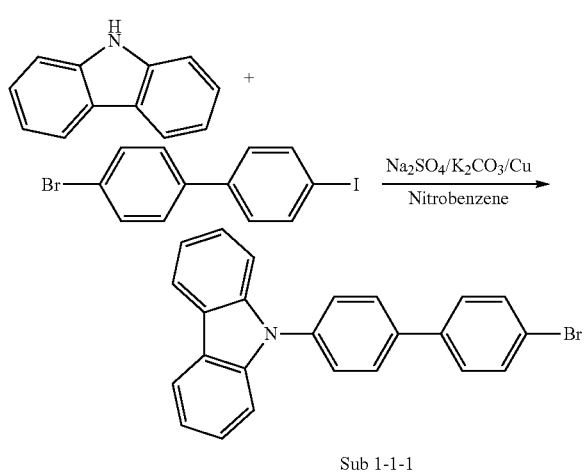

Sub 1-1-1

The starting material 9H-carbazole (50.16 g, 300 mmol) in 4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol), nitrobenzene using the synthesis method Sub 1, the product 80.05 g (yield: 67%) was obtained.

2) Synthesis Examples of Sub 1-1-2(L=9,9-dimethyl-9H-fluorene)

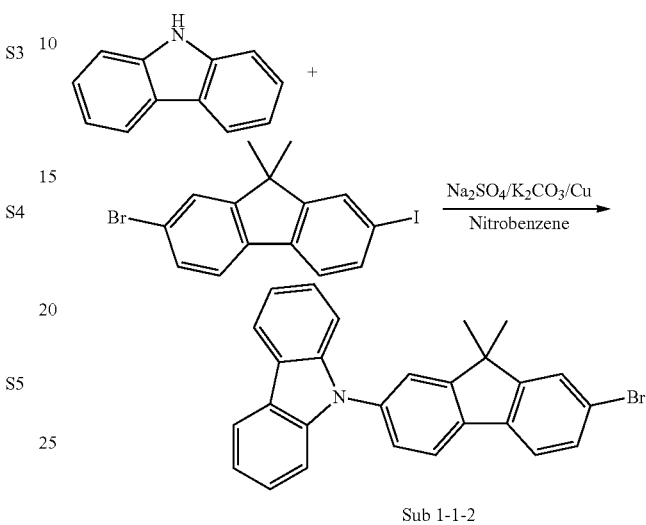

Sub 1-1-2

The starting material 9H-carbazole (50.16 g, 300 mmol) in 2-bromo-7-iodo-9,9-dimethyl-9H-fluorene (143.7 g, 360 mmol), Na₂SO₄ (42.6 g, 300 mmol), K₂CO₃ (41.4 g, 300 mmol), Cu (5.72 g, 90 mmol), nitrobenzene using the synthesis method Sub 1, the product 88.11 g (yield: 67%) was obtained.

3) Synthesis Examples of Sub 1-1-3(L=9,9-dimethyl-9H-fluorene)

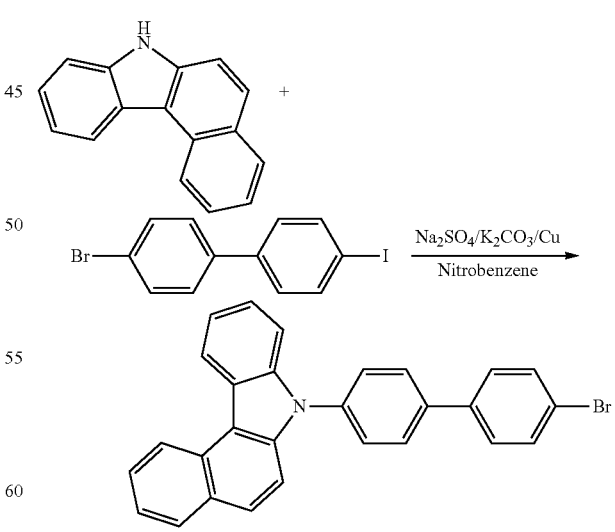

Sub 1-1-3

The starting material 7H-benzo[c]carbazole (65.18 g, 300 mmol) in 4-bromo-4'-iodo-1,1'-biphenyl(129.2 g, 360 mmol), Na₂SO₄ (42.6 g, 300 mmol), K₂CO₃ (41.4 g, 300 mmol), Cu (5.72 g, 90 mmol), nitrobenzene using the synthesis method Sub 1, the product 92.8 g (yield: 69%) was obtained.

4) Synthesis Examples of Sub 1-1-4(L=9,9-dimethyl-9H-fluorene)

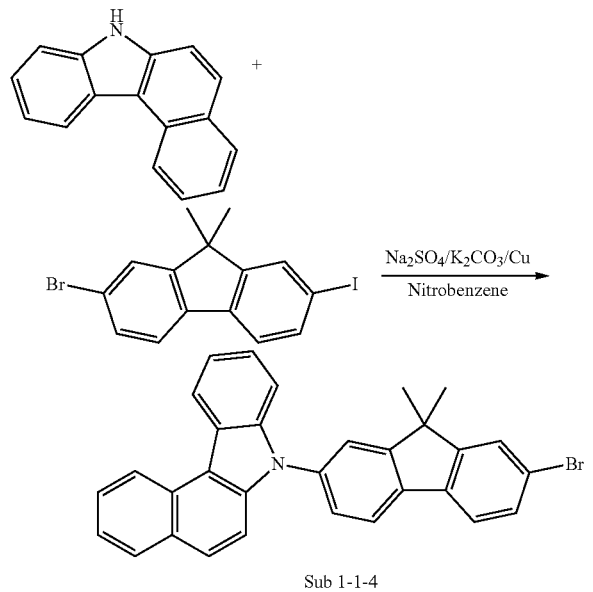

Sub 1-1-4

The starting material 7H-benzo[c]carbazole (65.18 g, 300 mmol) in 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene using the synthesis method Sub 1, the product 95.24 g (yield: 65%) was obtained.

5) Synthesis Examples of Sub 1-1-5(L=biphenyl)

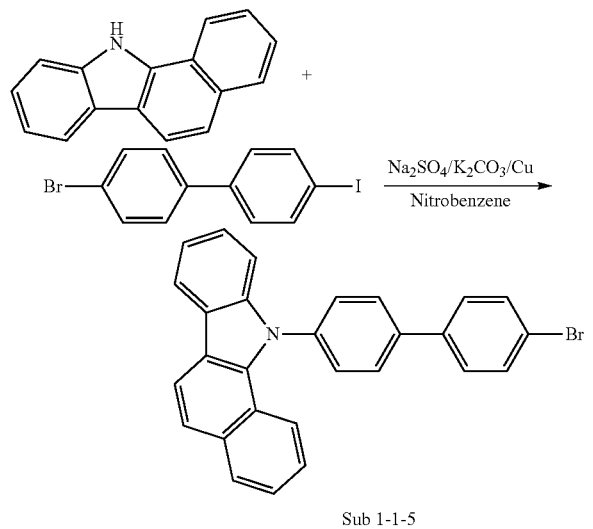

Sub 1-1-5

The starting material 11H-benzo[a]carbazole (65.18 g, 300 mmol) in 4-bromo-4'-iodo-1,1'-biphenyl(129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene using the synthesis method Sub 1, the product 80.05 g (yield: 62%) was obtained.

6) Synthesis Examples of Sub 1-1-6(L=9,9-dimethyl-9H-fluorene)

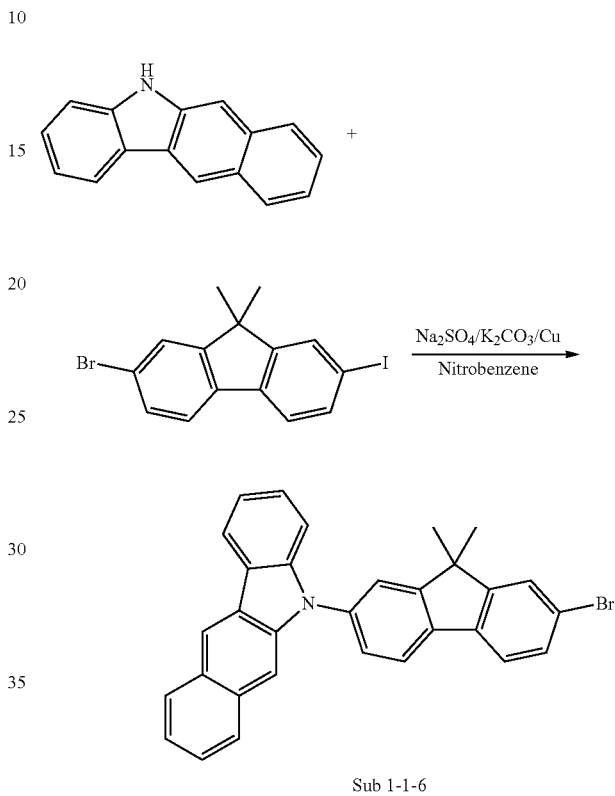

Sub 1-1-6

The starting material 5H-benzo[b]carbazole (65.18 g, 300 mmol) in 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene using the synthesis method Sub 1, the product 93.78 g (yield: 64%) was obtained.

7) Synthesis Examples of Sub 1-1-7(L=biphenyl)

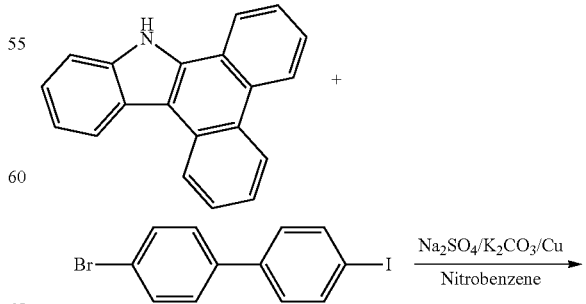

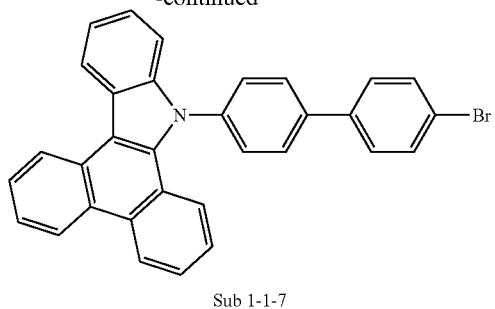

Sub 1-1-7

The starting material 9H-dibenzo[a,c]carbazole (80.2 g, 300 mmol) in 4-bromo-4'-iodo-1,1'-biphenyl(129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene using the synthesis method Sub 1, the product 98.7 g (yield: 66%) was obtained.

8) Synthesis Examples of Sub 1-1-9(L=9,9-dimethyl-9H-fluorene)

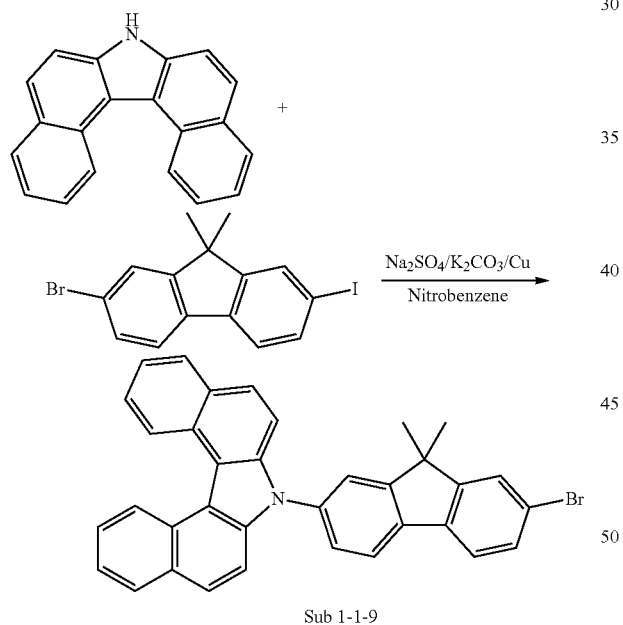

Sub 1-1-9

The starting material 7H-dibenzo[c,g]carbazole (80.2 g, 300 mmol) in 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene using the synthesis method Sub 1, the product 98.5 g (yield: 61%) was obtained.

2. Synthesis Examples of Sub 2

Sub 2 of the reaction scheme 1 can be synthesized by the reaction path of the reaction scheme 2 below.

<Reaction Scheme 2>

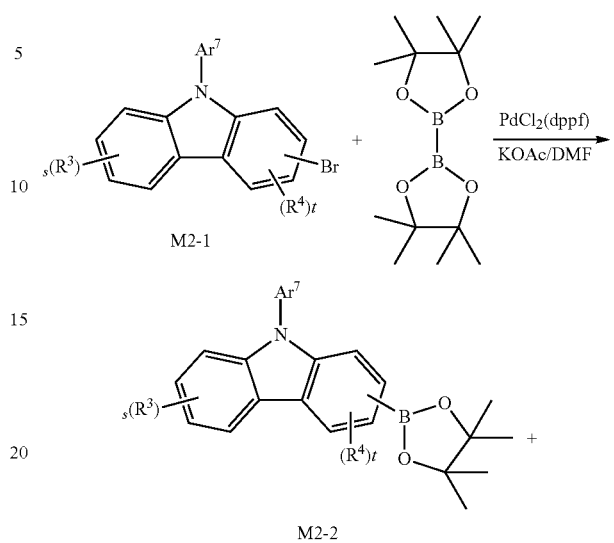

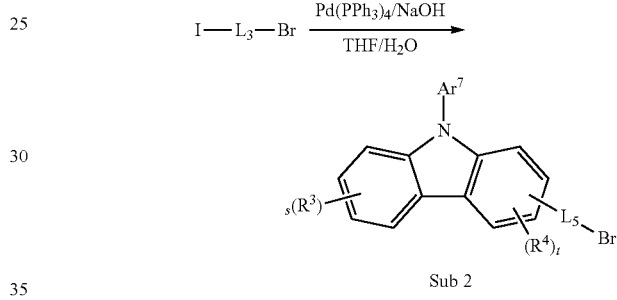

Sub 2

1) Synthesis Examples of M2-2-1

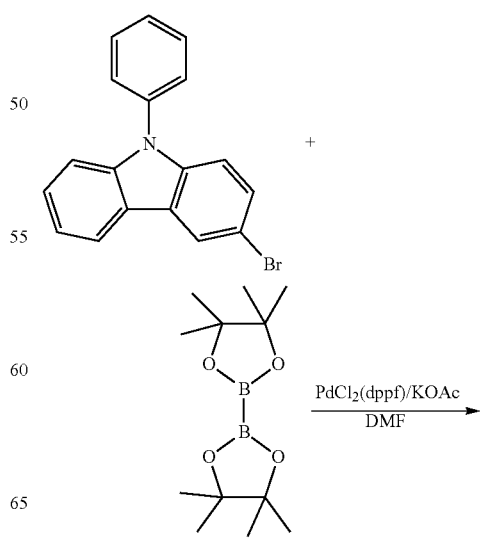

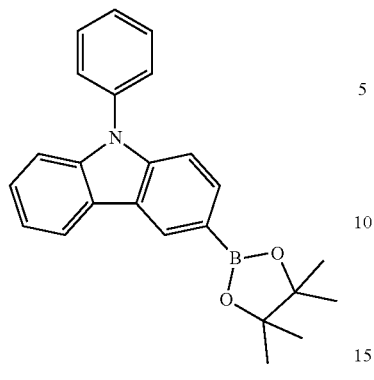

M2-2-1

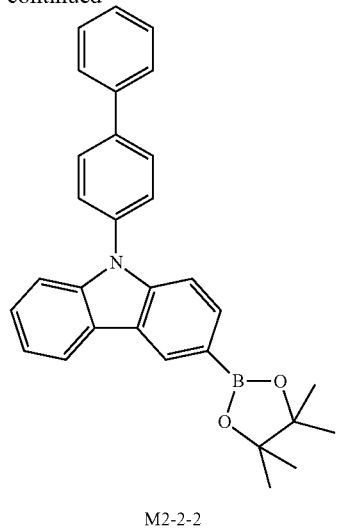

M2-2-2

After 3-bromo-9-phenyl-9H-carbazole (45.1 g, 140 mmol) was dissolved in DMF 980 mL, followed by being adding Bispinacolborate (39.1 g, 154 mmol), PdCl$_2$(dppf) catalyst (3.43 g, 4.2 mmol), KOAc (41.3 g, 420 mmol) in order, followed by stirring for 24 hours, to synthesize a borate compound, and then the resulting compound was separated over silicagel column and recrystallization to give the borate compound 35.2 g (68%).

2) Synthesis Examples of M2-2-2

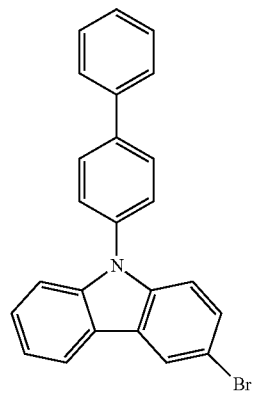

PdCl$_2$(dppf)/KOAc
DMF

The same procedure as described in the synthesis method of M2-2-1 above was carried out to obtain 40 g (64%).

3) Synthesis Examples of Sub 2-1-1

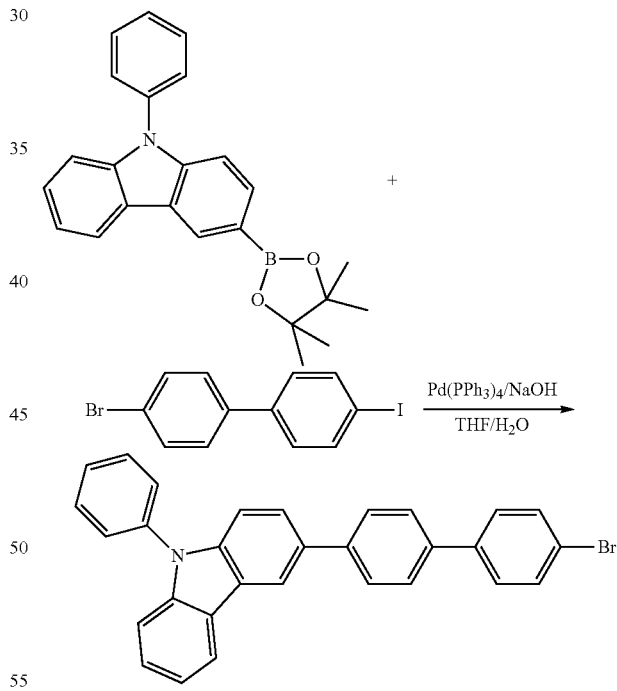

Sub 2-1-1

After M2-2-1 (29.5 g, 80 mmol) was dissolved in THF 360 mL, followed by being added 4-bromo-4'-iodo-1,1'-biphenyl(30.16 g, 84 mmol), Pd(PPh$_3$)$_4$ (2.8 g, 2.4 mmol), NaOH (9.6 g, 240 mmol), 180 mL of water, followed by reflux and stirring. Upon completion of the reaction, the reaction product was extracted with ether and water. The organic layer was dried with MgSO$_4$ and concentrated, and then the produced organic material was purified by silicagel column and recrystallized to obtain desired 26.56 g (70%).

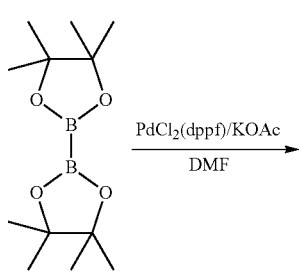

4) Synthesis Examples of Sub 2-1-2

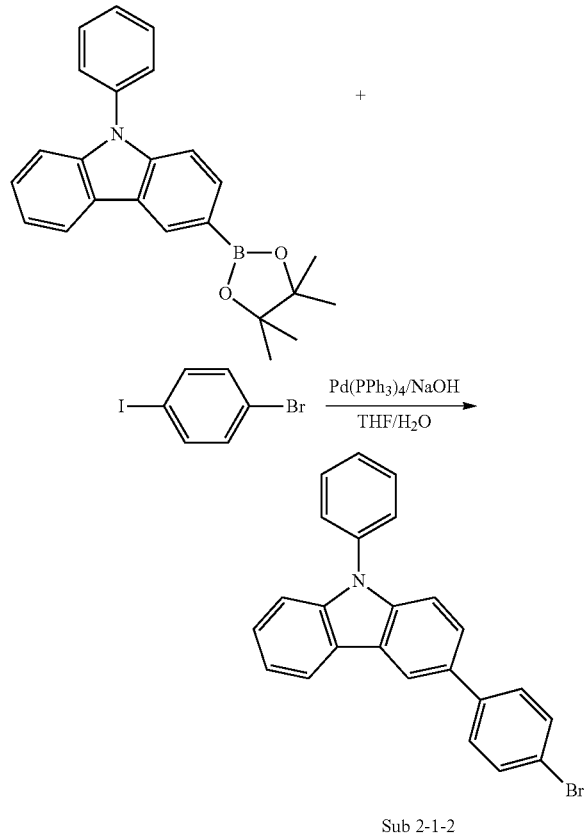

Sub 2-1-2

After M2-2-1 (29.5 g, 80 mmol) was dissolved in THF 360 mL, followed by being added 1-bromo-4-iodobenzene (23.8 g, 84 mmol), Pd(PPh₃)₄ (2.8 g, 2.4 mmol), NaOH (9.6 g, 240 mmol), 180 mL of water, followed by reflux and stirring. Upon completion of the reaction, the reaction product was extracted with ether and water. The organic layer was dried with MgSO₄ and concentrated, and then the produced organic material was purified by silicagel column and recrystallized to obtain desired 22.9 g (72%).

5) Synthesis Examples of Sub 2-1-3

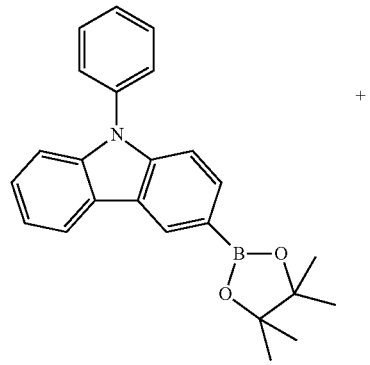

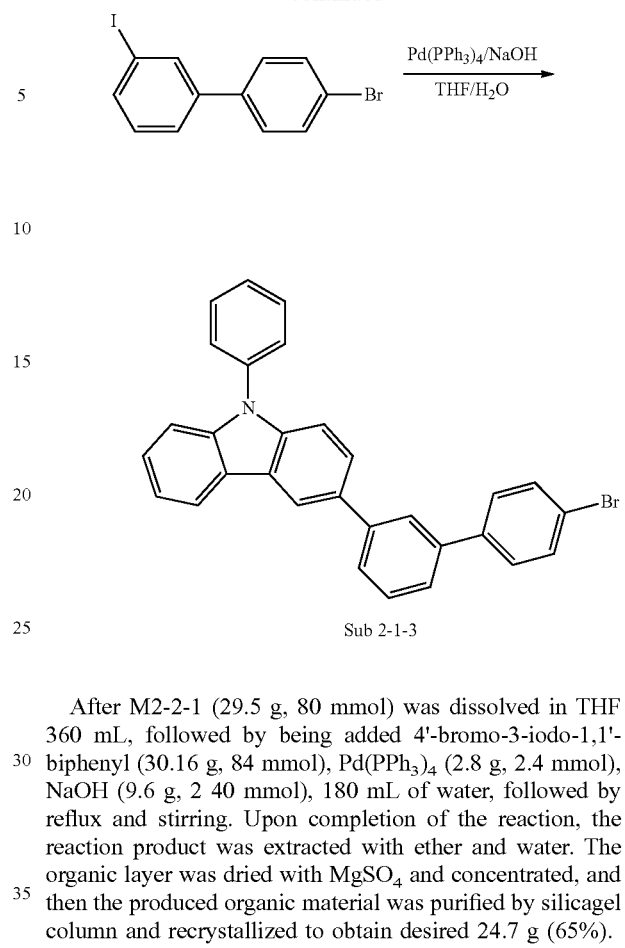

Sub 2-1-3

After M2-2-1 (29.5 g, 80 mmol) was dissolved in THF 360 mL, followed by being added 4'-bromo-3-iodo-1,1'-biphenyl (30.16 g, 84 mmol), Pd(PPh₃)₄ (2.8 g, 2.4 mmol), NaOH (9.6 g, 2 40 mmol), 180 mL of water, followed by reflux and stirring. Upon completion of the reaction, the reaction product was extracted with ether and water. The organic layer was dried with MgSO₄ and concentrated, and then the produced organic material was purified by silicagel column and recrystallized to obtain desired 24.7 g (65%).

6) Synthesis Examples of Sub 2-1-4

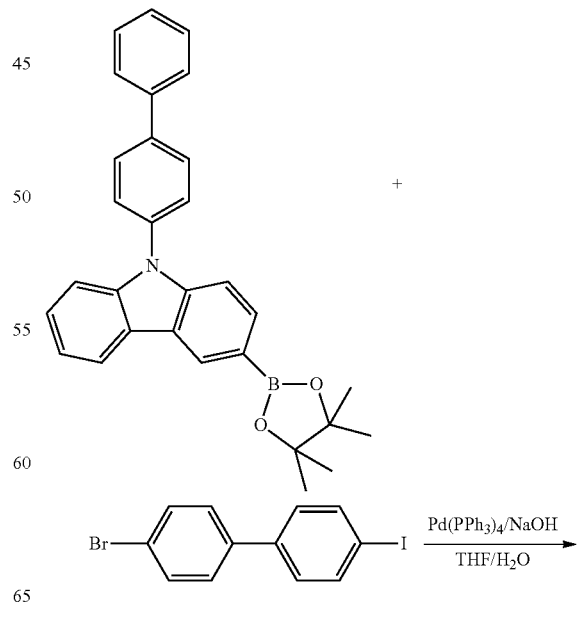

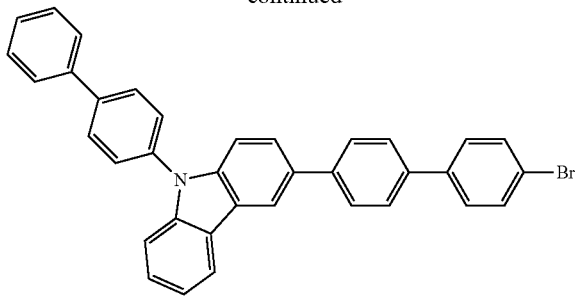

Sub 2-1-4

After M2-2-2 (35.63 g, 80 mmol) obtained by the synthesis was dissolved in THF 360 mL, followed by being added 4-bromo-4'-iodo-1,1'-biphenyl(30.16 g, 84 mmol), Pd(PPh$_3$)$_4$ (2.8 g, 2.4 mmol), NaOH (9.6 g, 240 mmol), 180 mL of water, followed by reflux and stirring. Upon completion of the reaction, the reaction product was extracted with ether and water. The organic layer was dried with MgSO$_4$ and concentrated, and then the produced organic material was purified by silicagel column and recrystallized to obtain desired 29.51 g (67%).

3. Synthesis Examples of Sub 3

Sub 3 of the reaction scheme 1 can be synthesized by the reaction path of the reaction scheme 3 below.

<Reaction Scheme 3>

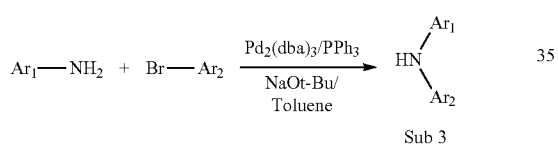

Sub 3

Synthesis Method of Sub 3

After [1,1'-biphenyl]-4-amine (1 equiv) and 4-bromo-1,1'-biphenyl (1.1 equiv) were dissolved in toluene, followed by being added respectively Pd$_2$(dba)$_3$ (0.05 equiv), PPh$_3$ (0.1 equiv), NaOt-Bu (3 equiv), followed by reflux and stirring at 100° C. for 24 hours. Upon completion of the reaction, the reaction product was extracted with ether and water. The organic layer was dried with MgSO$_4$ and concentrated, and then the produced organic material was purified by silicagel column and recrystallized to obtain desired di([1,1'-biphenyl]-4-yl)amine.

The examples of Sub 3 include, but are not limited to, the following compounds.

Sub 3-1

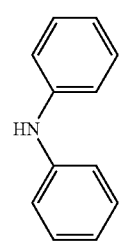

Sub 3-2

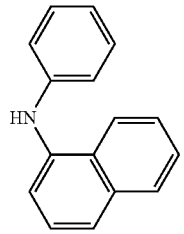

Sub 3-3

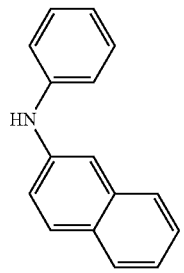

Sub 3-4

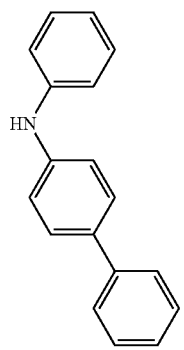

Sub 3-5

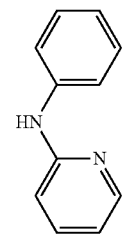

Sub 3-6

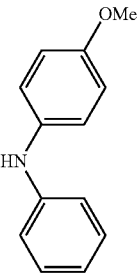

Sub 3-7
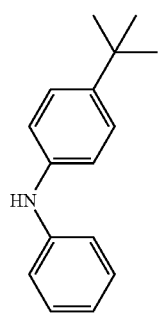
Sub 3-8
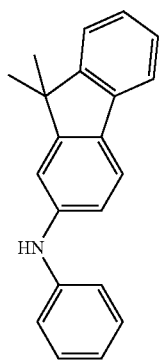
Sub 3-9
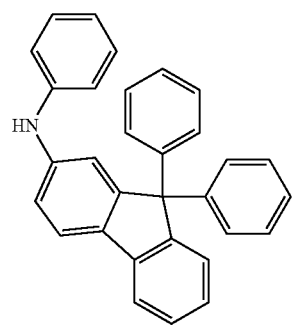
Sub 3-10
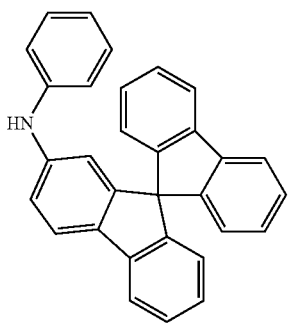
Sub 3-11
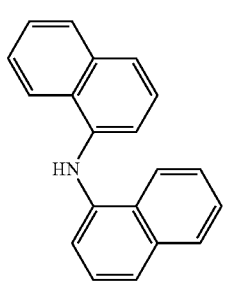
Sub 3-12
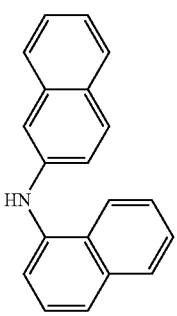
Sub 3-13
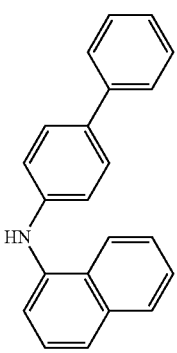
Sub 3-14
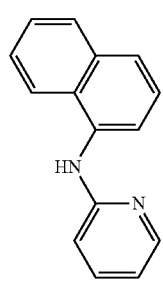
Sub 3-15
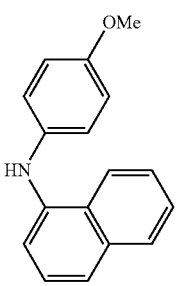
Sub 3-16
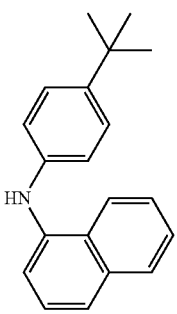

Sub 3-17
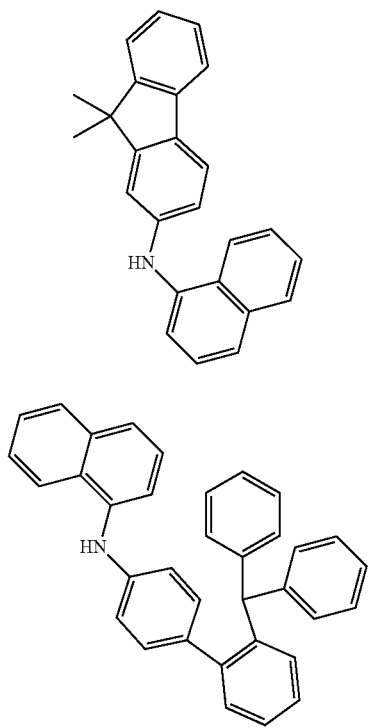
Sub 3-18
Sub 3-19
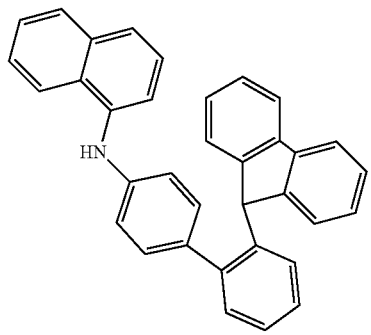
Sub 3-20
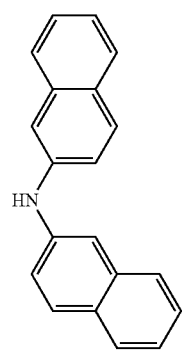
Sub 3-21
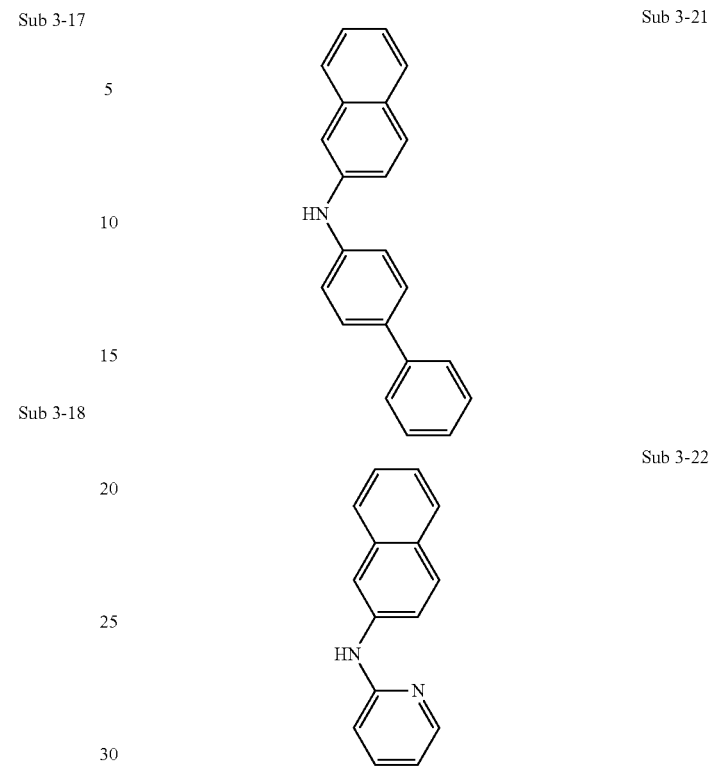
Sub 3-22
Sub 3-23
Sub 3-24

Sub 3-25
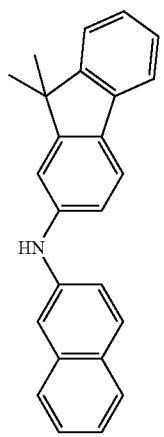
Sub 3-26
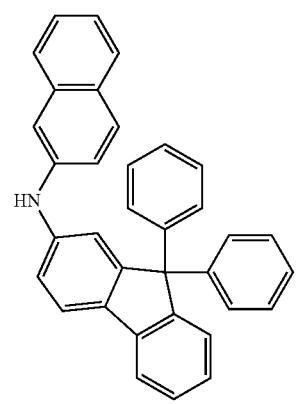
Sub 3-27
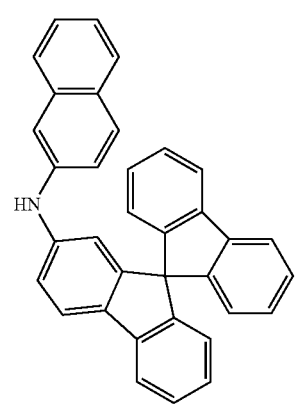
Sub 3-28
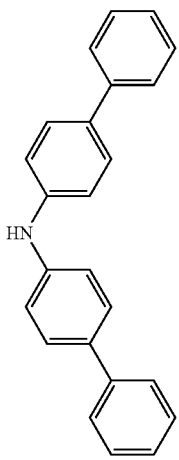
Sub 3-29
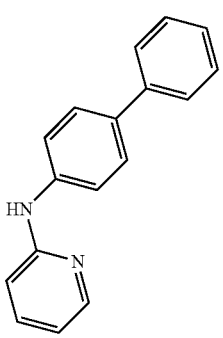
Sub 3-30
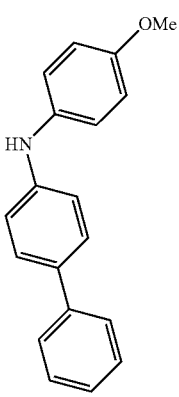
Sub 3-31
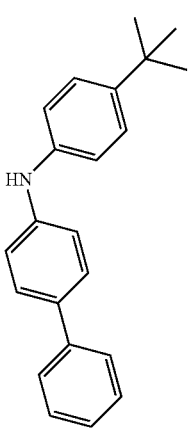

Sub 3-32
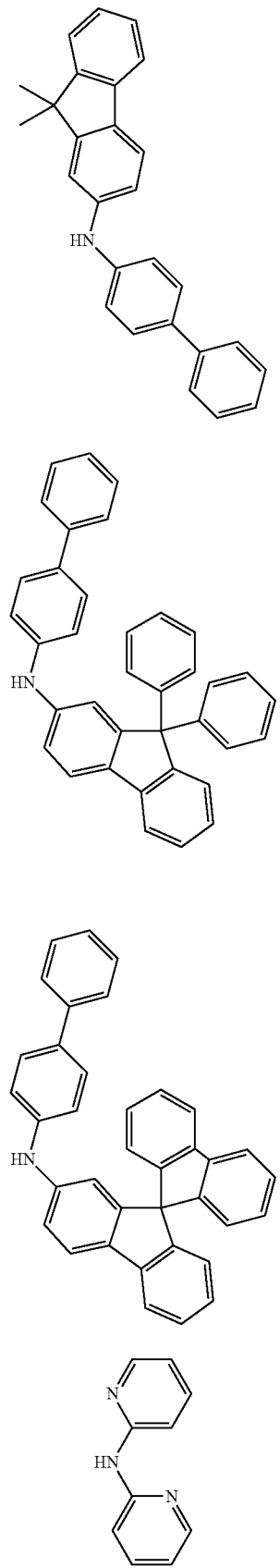
Sub 3-33
Sub 3-34
Sub 3-35
Sub 3-36
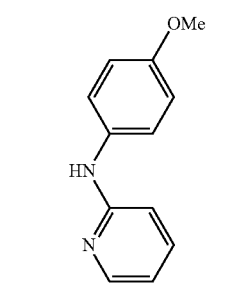
Sub 3-37
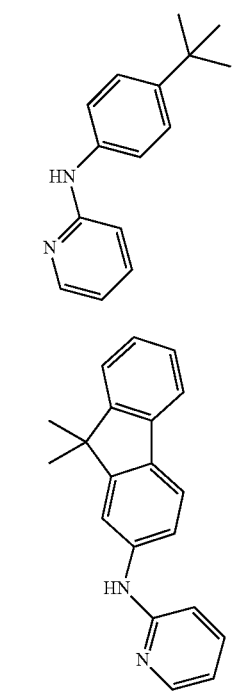
Sub 3-38
Sub 3-39
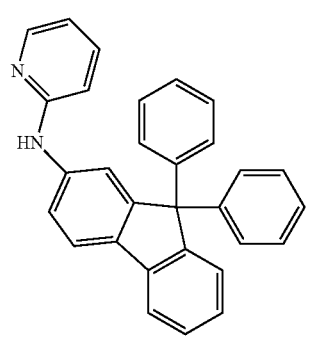
Sub 3-40
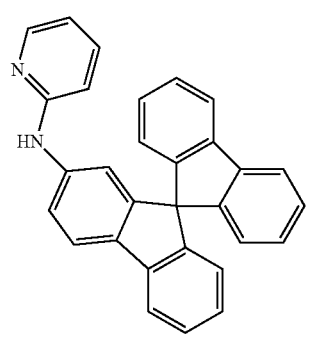

Sub 3-41
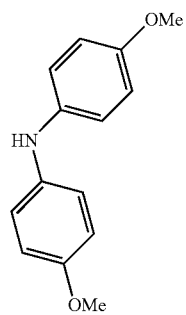
Sub 3-42
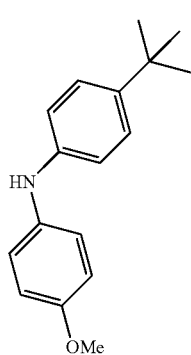
Sub 3-43
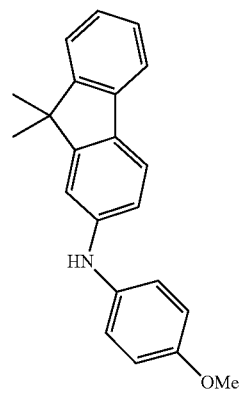
Sub 3-44
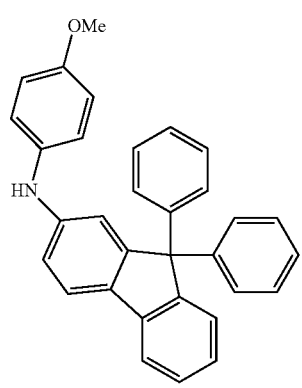
Sub 3-45
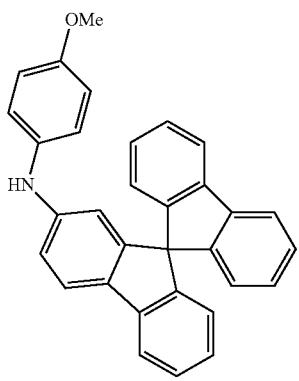
Sub 3-46
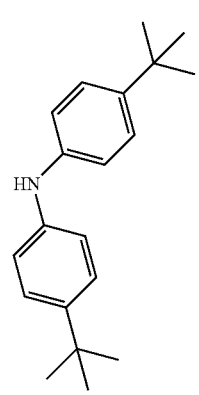
Sub 3-47
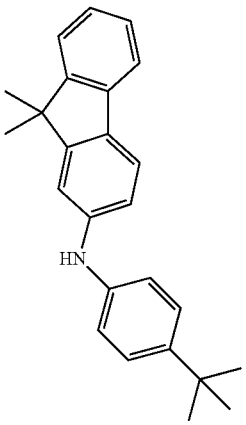
Sub 3-48
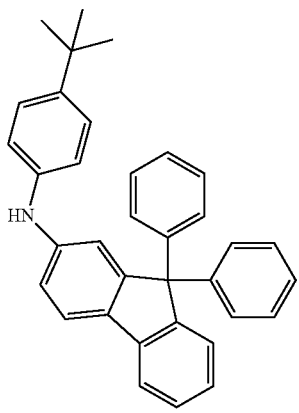

Sub 3-49

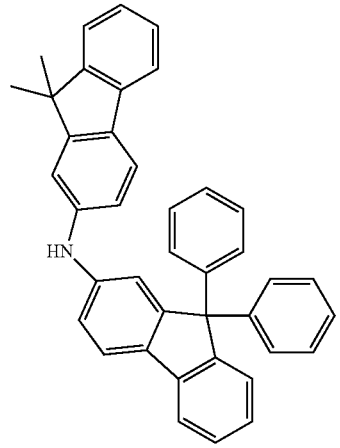

Sub 3-51

Sub 3-50

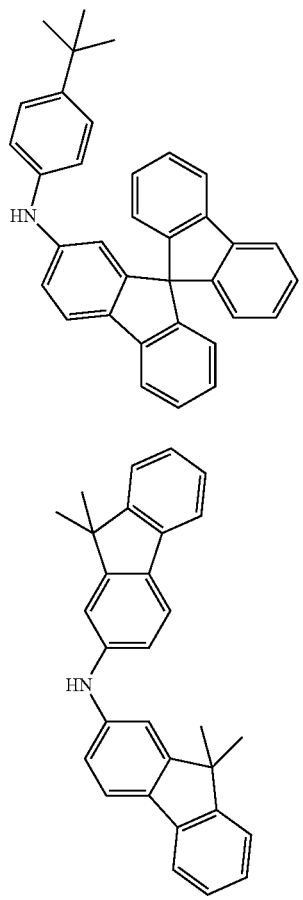

Sub 3-52

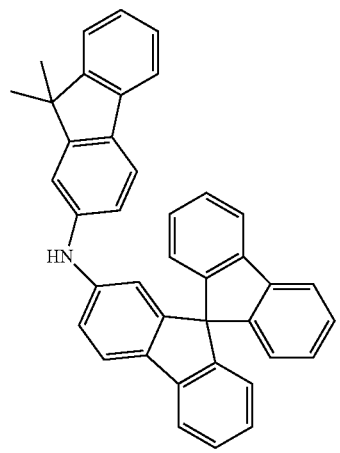

TABLE 1

| compound | FD-MS | compound | FD-MS |
|---|---|---|---|
| Sub 3-1 | m/z = 169.09(C12H11N = 169.22) | Sub 3-2 | m/z = 219.10(C16H13N = 219.28) |
| Sub 3-3 | m/z = 219.10(C16H13N = 219.28) | Sub 3-4 | m/z = 245.12(C18H15N = 245.32) |
| Sub 3-5 | m/z = 170.08(C11H10N2 = 170.21) | Sub 3-6 | m/z = 199.10(C10H13NO = 199.25) |
| Sub 3-7 | m/z = 225.15(C16H19N = 225.33) | Sub 3-8 | m/z = 285.15(C21H19N = 285.38) |
| Sub 3-9 | m/z = 409.18(C31H23N = 409.52) | Sub 3-10 | m/z = 407.17(C31H21N = 407.51) |
| Sub 3-11 | m/z = 269.12(C20H15N = 269.34) | Sub 3-12 | m/z = 269.12(C20H15N = 269.34) |
| Sub 3-13 | m/z = 295.14(C22H17N = 295.38) | Sub 3-14 | m/z = 220.10(C15H12N2 = 220.27) |
| Sub 3-15 | m/z = 249.12(C17H12NO = 249.31) | Sub 3-16 | m/z = 275.17(C20H21N = 275.39) |
| Sub 3-17 | m/z = 335.17(C25H21N = 335.44) | Sub 3-18 | m/z = 459.20(C35H25N = 459.58) |
| Sub 3-19 | m/z = 457.18(C35H23N = 457.56) | Sub 3-20 | m/z = 269.12(C20H15N = 269.34) |
| Sub 3-21 | m/z = 295.14(C22H17N = 295.38) | Sub 3-22 | m/z = 220.10(C15H2N2 = 220.27) |
| Sub 3-23 | m/z = 249.12(C17H15NO = 249.31) | Sub 3-24 | m/z = 275.17(C20H21N = 275.39) |
| Sub 3-25 | m/z = 335.17(C25H21N = 335.44) | Sub 3-26 | m/z = 459.20(C35H25N = 459.58) |
| Sub 3-27 | m/z = 457.18(C35H23N = 457.56) | Sub 3-28 | m/z = 321.15(C24H19N = 321.41) |
| Sub 3-29 | m/z = 246.12(C17H14N2 = 246.31) | Sub 3-30 | m/z = 275.13(C19H17NO = 275.34) |
| Sub 3-31 | m/z = 301.18(C22H23N = 301.42) | Sub 3-32 | m/z = 361.18(C27H23N = 361.48) |
| Sub 3-33 | m/z = 485.21(C37H27N = 485.62) | Sub 3-34 | m/z = 483.20(C37H25N = 483.60) |
| Sub 3-35 | m/z = 171.08(C10H09N3 = 171.20) | Sub 3-36 | m/z = 200.09(C12H12N2O = 200.24) |
| Sub 3-37 | m/z = 226.15(C15H18N2 = 226.32) | Sub 3-38 | m/z = 286.15(C20H18N2 = 286.37) |
| Sub 3-39 | m/z = 410.18(C30H22N2 = 410.51) | Sub 3-40 | m/z = 408.16(C30H20N2 = 408.49) |
| Sub 3-41 | m/z = 229.11(C14H15NO2 = 229.27) | Sub 3-42 | m/z = 255.16(C17H21NO = 255.35) |
| Sub 3-43 | m/z = 315.16(C22H21NO = 315.41) | Sub 3-44 | m/z = 439.19(C32H25NO = 439.55) |
| Sub 3-45 | m/z = 437.18(C32H23NO = 437.53) | Sub 3-46 | m/z = 281.21(C20H27N = 281.44) |
| Sub 3-47 | m/z = 341.21(C25H27N = 341.49) | Sub 3-48 | m/z = 465.25(C35H31N = 465.63) |
| Sub 3-49 | m/z = 463.23(C35H29N = 463.61) | Sub 3-50 | m/z = 401.21(C30H27N = 401.54) |
| Sub 3-51 | m/z = 525.25(C40H31N = 525.68) | Sub 3-52 | m/z = 523.23(C40H29N = 523.66) |

Synthesis of Final Product of Formula (1)

After Sub 1 (1 equiv) or Sub 2 (1 equiv) was dissolved in toluene, followed by being added respectively Sub 3 (1.1 equiv), Pd$_2$(dba)$_3$ (0.05 equiv), PPh$_3$ (0.1 equiv), NaOt-Bu (3equiv), followed by reflux and stirring at 100° C. for 24 hours. Upon completion of the reaction, the reaction product was extracted with ether and water. The organic layer was dried with MgSO$_4$ and concentrated, and then the produced organic material was purified by silicagel column and recrystallized to obtain desired Final Product.

Synthesis Examples of 1-17

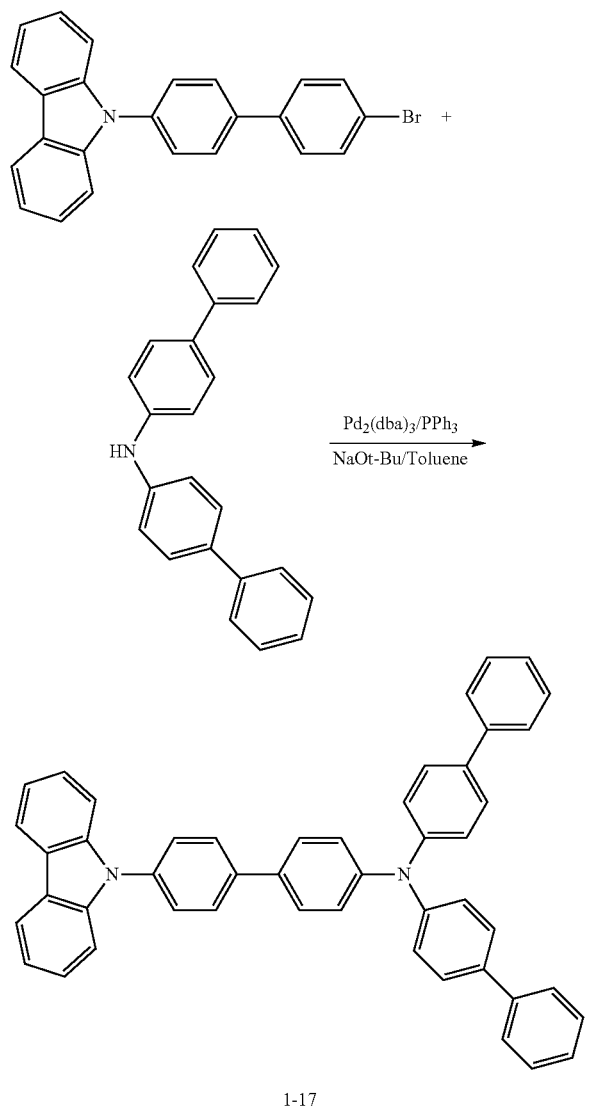

1-17

After 9-(4'-bromo-[1,1'-biphenyl]-4-yl)-9H-carbazole (9.6 g, 24 mmol) was dissolved in toluene, followed by being added respectively di([1,1'-biphenyl]-4-yl)amine (6.4 g, 20 mmol), Pd$_2$(dba)$_3$ (0.05 equiv), PPh$_3$ (0.1 equiv), NaOt-Bu (3 equiv), followed by reflux and stirring at 100° C. for 24 hours. Upon completion of the reaction, the reaction product was extracted with ether and water. The organic layer was dried with MgSO$_4$ and concentrated, and then the produced organic material was purified by silicagel column and recrystallized to obtain desired Final Product 12.9 g (yield: 84%).

Synthesis Examples of 1-32

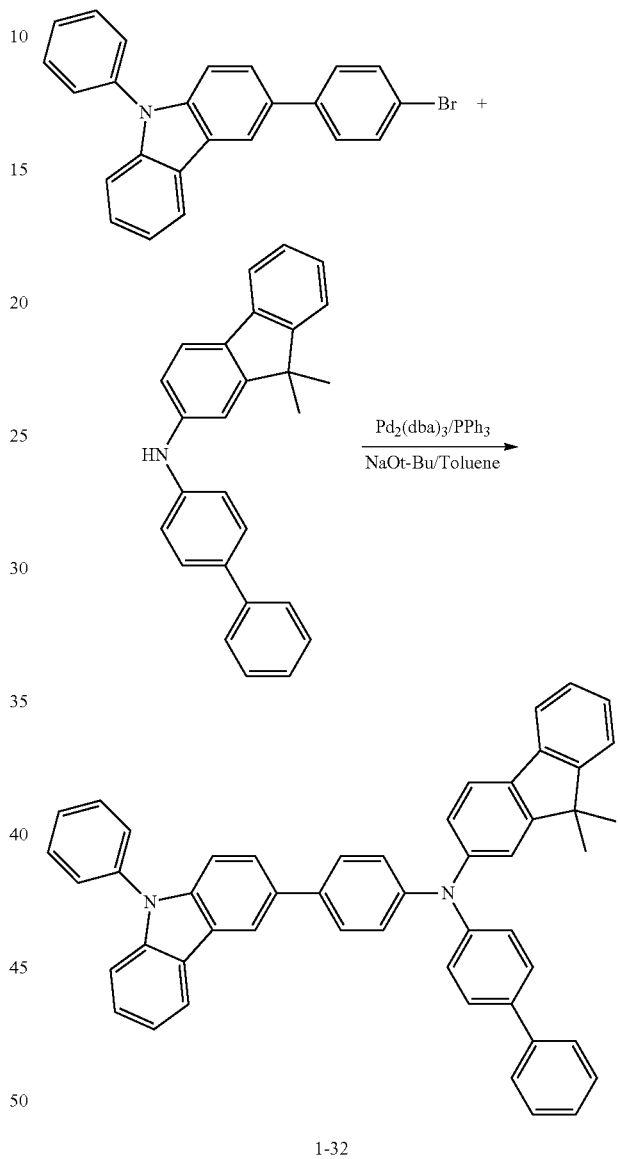

1-32

After 3-(4-bromophenyl)-9-phenyl-9H-carbazole (9.6 g, 24 mmol) was dissolved in toluene, followed by being added respectively N-([1,1'-biphenyl]-4-yl)-9,9-dimethyl-9H-fluoren-2-amine (7.2 g, 20 mmol), Pd$_2$(dba)$_3$ (0.05 equiv), PPh$_3$ (0.1 equiv), NaOt-Bu (3 equiv) followed by reflux and stirring at 100° C. for 24 hours. Upon completion of the reaction, the reaction product was extracted with ether and water. The organic layer was dried with MgSO$_4$ and concentrated, and then the produced organic material was purified by silicagel column and recrystallized to obtain desired Final Product 13.8 g (yield: 85%).

A part of the obtained product above was confirmed by the following Mass Data

TABLE 2

| compound | FD-MS | compound | FD-MS |
|---|---|---|---|
| 1-17 | m/z = 638.27 (C48H34N2 = 638.80) | 1-20 | m/z = 678.30 (C51H38N2 = 678.86) |
| 1-21 | m/z = 802.33 (C61H42N2 = 803.00) | 1-22 | m/z = 800.32 (C61H40N2 = 800.98) |
| 1-32 | m/z = 678.30 (C51H38N2 = 678.86) | 1-33 | m/z = 802.33 (C61H42N2 = 803.00) |
| 1-34 | m/z = 800.32 (C61H40N2 = 800.98) | 1-43 | m/z = 714.30 (C54H38N2 = 714.89) |
| 1-44 | m/z = 754.33 (C57H42N2 = 754.96) | 1-45 | m/z = 878.37 (C67H46N2 = 879.10) |
| 1-46 | m/z = 876.35 (C67H44N2 = 877.08) | 1-47 | m/z = 744.26 (C54H36N2S = 744.94) |
| 1-52 | m/z = 826.33 (C63H42N2 = 827.02) | 1-53 | m/z = 824.32 (C63H40N2 = 825.01) |
| 1-54 | m/z = 688.29 (C52H36N2 = 688.86) | 1-55 | m/z = 728.32 (C55H40N2 = 728.92) |
| 1-57 | m/z = 778.33 (C59H42N2 = 778.98) | 1-58 | m/z = 902.37 (C69H46N2 = 903.12) |
| 1-59 | m/z = 900.35 (C69H44N2 = 901.10) | | |

Synthesis Examples 2

The final product 2 represented by Formula (2) according to the present invention can be synthesized by reaction between Sub 4 and Sub 5 as illustrated in the following Reaction Scheme 4.

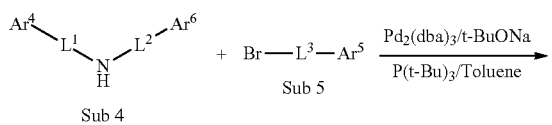

<Reaction Scheme 4>

Final product 2

Synthesis Examples Sub 4

Sub 4 of Reaction Scheme 4 can be synthesized, but not limited to, by the Reaction Path of the the following Reaction Scheme 5,

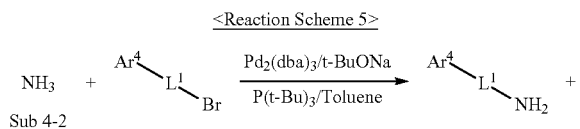

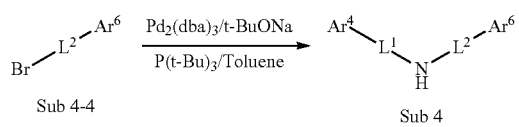

<Reaction Scheme 5>

Example of Sub 4 (1)

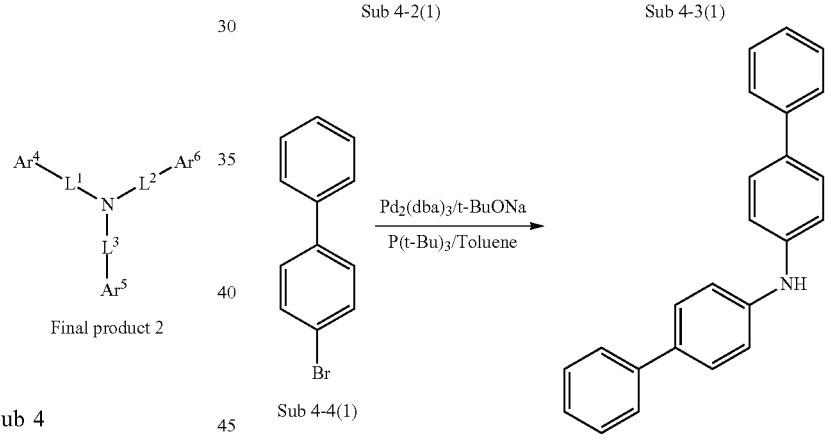

Synthesis of Sub 4-3 (1)

In a round-bottom flask, Sub 4-1 (1) (0.3 g, 20 mmol), Sub 4-2 (1) (4.7 g, 20 mmol), Pd$_2$(dba)$_3$ (0.5 g, 0.6 mmol), P(t-Bu)$_3$ (0.2 g, 2 mmol), t-BuONa (5.8 g, 60 mmol), and toluene (300 mL) were placed and allowed to react at 100° C. After completion of the reaction, the reaction product was extracted with CH$_2$Cl$_2$ and water, and the extracted organic layer was dried with MgSO$_4$ and concentrated. And the produced organic material was purified by a silicagel column and recrystallized, to give 2.5 g of Sub 4-3 (1)(yield: 75%).

Synthesis of Sub 4 (1)

In a round-bottom flask, Sub 4-3 (1) (2.5 g, 15 mmol), Sub 4-4 (1) (3.5 g, 15 mmol), Pd$_2$(dba)$_3$ (0.5 g, 0.5 mmol), P(t-Bu)$_3$ (0.2 g, 2 mmol), t-BuONa (5.8 g, 60 mmol), toluene (300 mL) were placed and allowed to react at 100° C. After completion of the reaction, the product was extracted with CH₂Cl₂ and water, and the extracted organic layer was dried over MgSO₄ and concentrated, after which the product was purified by a silicagel column and recrystallized, to give 3.8 g of Sub 4 (1)(yield:78%).

The examples of Sub 4 include, but are not limited to, the followings.

Sub 4(1)

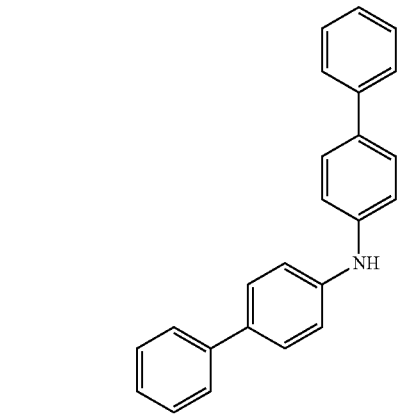

Sub 4(2)

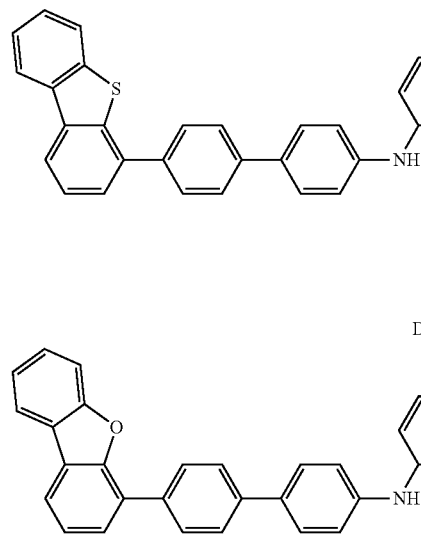

Sub 4(3)

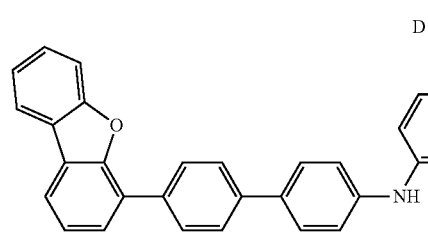

Sub 4(4)

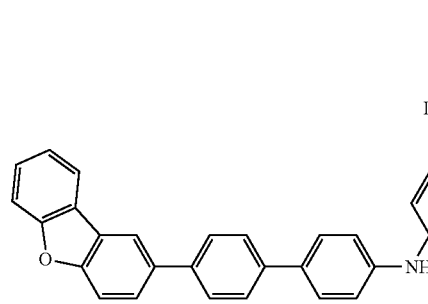

Sub 4(5)

Sub 4(6)

Sub 4(7)

Sub 4(8)

Sub 4(9)

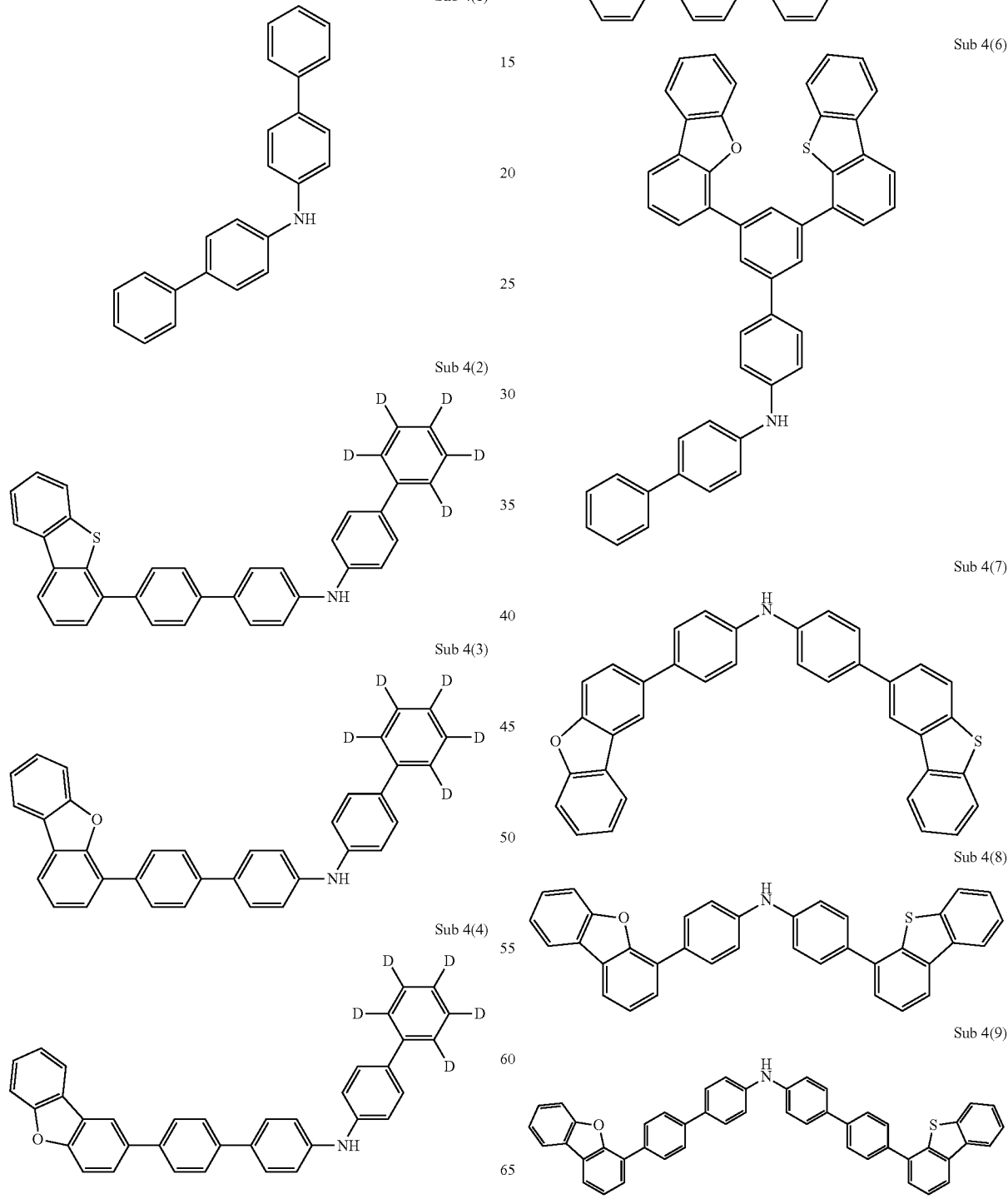

Sub 4(10)
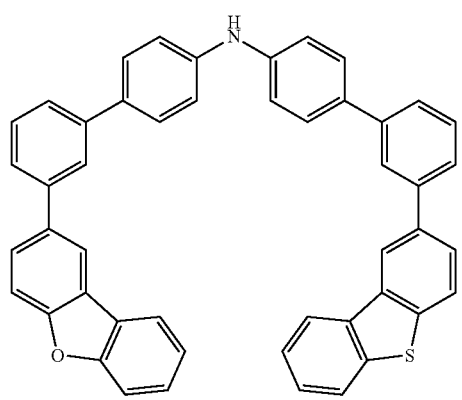
Sub 4(11)
Sub 4(12)
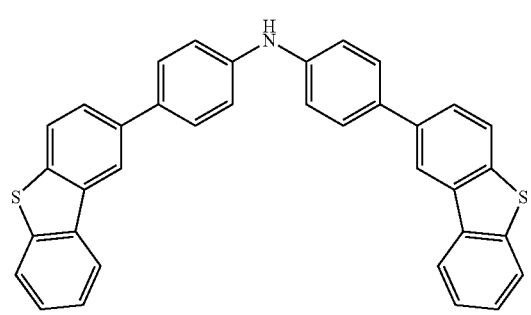
Sub 4(13)
Sub 4(14)
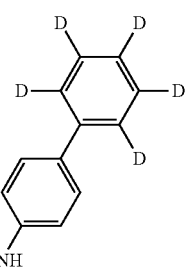
Sub 4(15)
Sub 4(16)
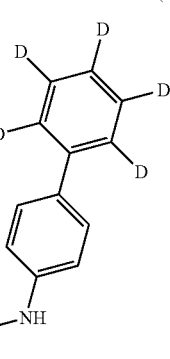
Sub 4(17)
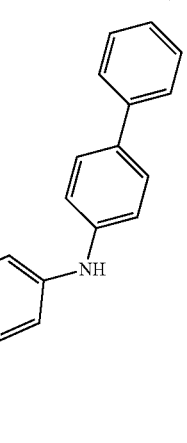
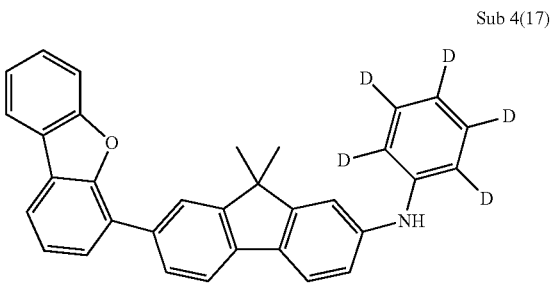

Sub 4(18)
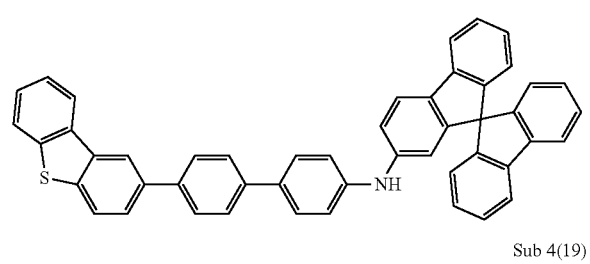
Sub 4(19)
Sub 4(20)
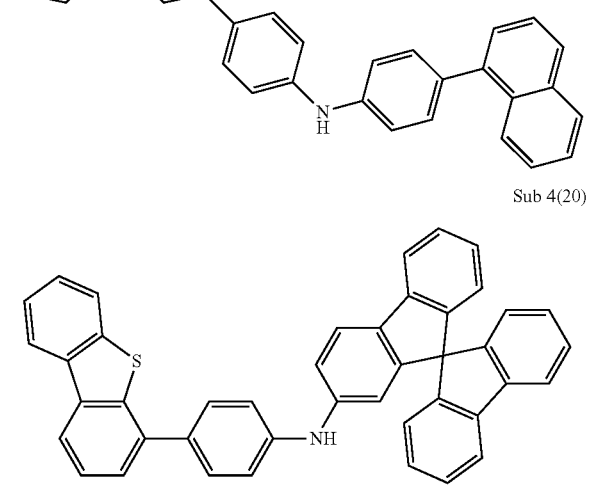
Sub 4(21)
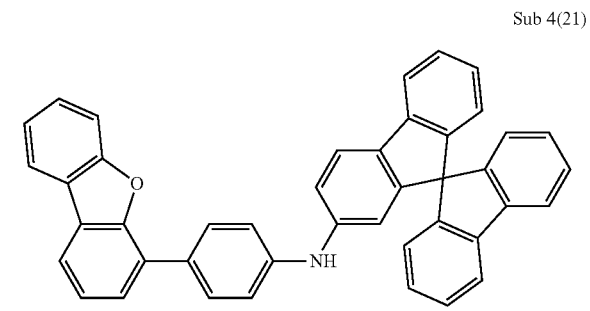
Sub 4(22)
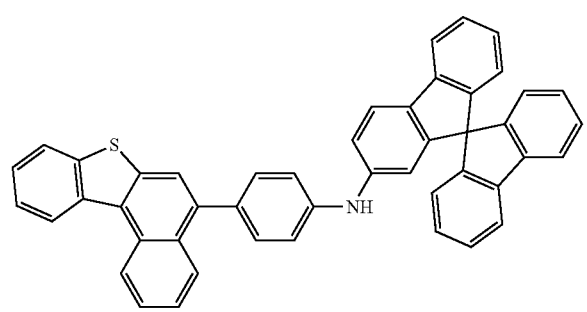
Sub 4(23)
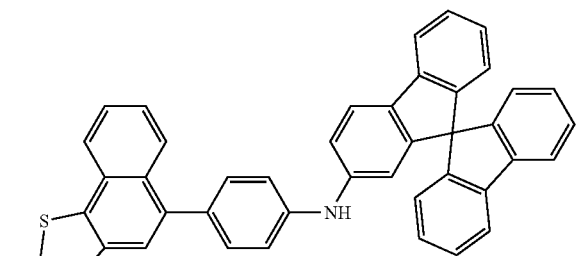
Sub 4(24)
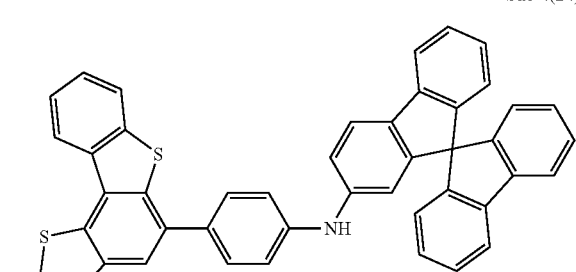
Sub 4(25)
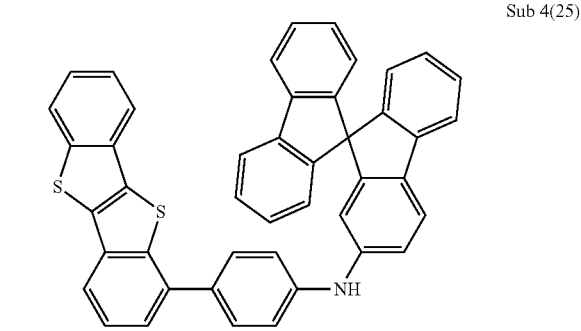
Sub 4(26)
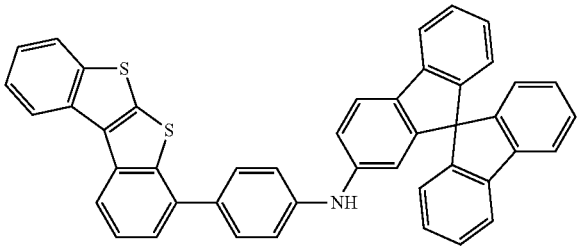
Sub 4(27)
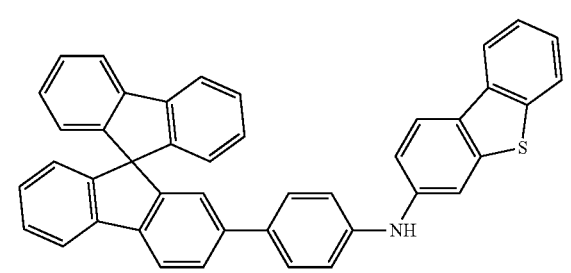

Sub 4(28)
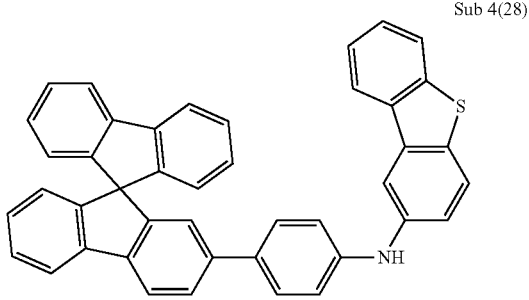
Sub 4(29)
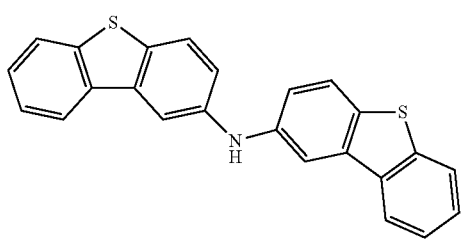
Sub 4(30)
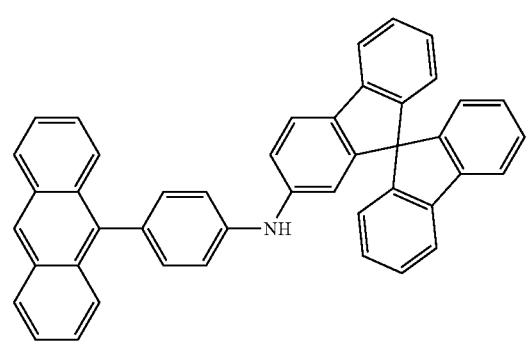
Sub 4(31)
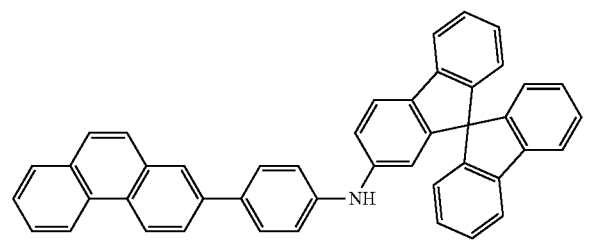
Sub 4(32)
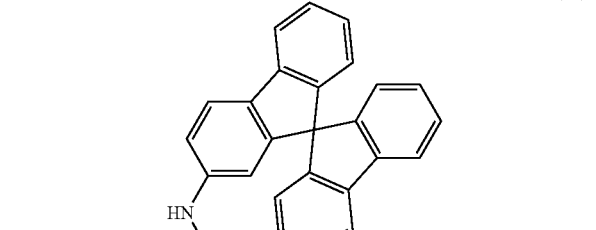
Sub 4(33)
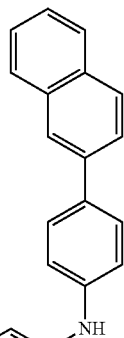
Sub 4(34)
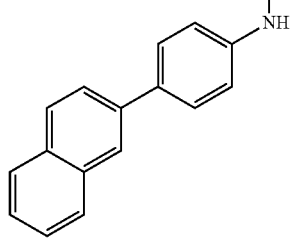
Sub 4(35)
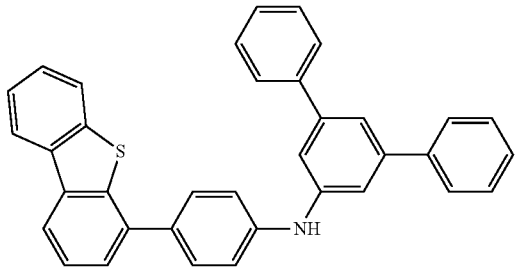
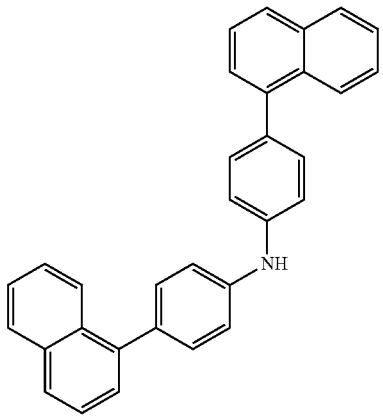

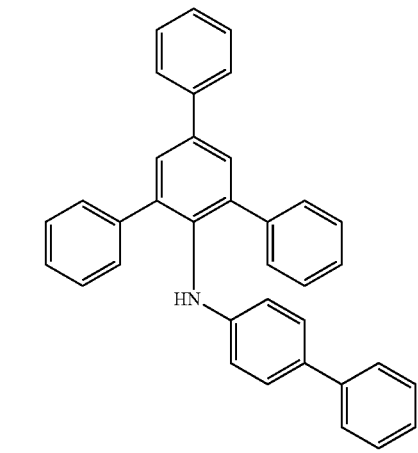

Sub 4(36)

Sub 4(37)

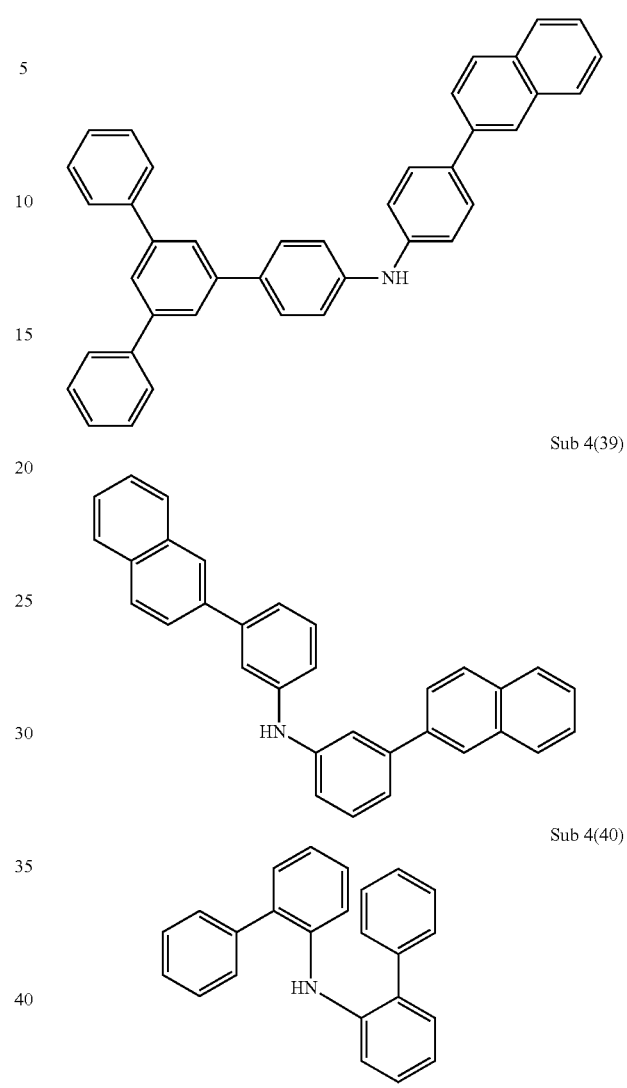

Sub 4(38)

Sub 4(39)

Sub 4(40)

TABLE 3

| compound | FD-MS | compound | FD-MS |
|---|---|---|---|
| Sub 4(1) | m/z = 321.15(C24H19N = 321.41) | Sub 4(2) | m/z = 508.20(C36H20D5NS = 508.69) |
| Sub 4(3) | m/z = 492.22(C36H20D5NO = 492.62) | Sub 4(4) | m/z = 492.22(C36H20D5NO = 492.62) |
| Sub 4(5) | m/z = 508.20(C36H20D5NS = 508.69) | Sub 4(6) | m/z = 569.21(C48H31NOS = 669.83) |
| Sub 4(7) | m/z = 517.15(C36H23NOS = 517.64) | Sub 4(8) | m/z = 517.15(C36H23NOS = 517.64) |
| Sub 4(9) | m/z = 669.21(C48H31NOS = 669.83) | Sub 4(10) | m/z = 669.21(C48H31NOS = 669.83) |
| Sub 4(11) | m/z = 533.13(C36H23NS2 = 533.70) | Sub 4(12) | m/z = 501.17(C36H23NO2 = 501.57) |
| Sub 4(13) | m/z = 517.15(C36H23NOS = 517.64) | Sub 4(14) | m/z = 532.26(C39H24D5NO = 532.68) |
| Sub 4(15) | m/z = 548.23(C39H24D5NS = 548.74) | Sub 4(16) | m/z = 543.20(C39H29NS = 543.72) |
| Sub 4(17) | m/z = 456.22(C33H20D5NO = 456.59) | Sub 4(18) | m/z = 665.22(C49H31NS = 665.84) |
| Sub 4(19) | m/z = 477.16(C34H23NS = 477.62) | Sub 4(20) | m/z = 589.19(C43H27NS = 589.75) |
| Sub 4(21) | m/z = 573.21(C43H27NO = 573.68) | Sub 4(22) | m/z = 639.20(C47H29NS = 639.80) |
| Sub 4(23) | m/z = 639.20(C47H29NS = 639.80) | Sub 4(24) | m/z = 695.17(C49H29NS2 = 695.89) |
| Sub 4(25) | m/z = 645.16(C45H27NS2 = 645.83) | Sub 4(26) | m/z = 645.16(C45H27NS2 = 645.83) |
| Sub 4(27) | m/z = 589.19(C43H27NS = 589.75) | Sub 4(28) | m/z = 589.19(C43H27NS = 589.75) |
| Sub 4(29) | m/z = 381.06(C24H15NS2 = 381.51) | Sub 4(30) | m/z = 583.23(C45H29N = 583.72) |
| Sub 4(31) | m/z = 583.23(C45H29N = 583.72) | Sub 4(32) | m/z = 645.25(C50H31N = 645.79) |
| Sub 4(33) | m/z = 421.18(C32H23N = 421.53) | Sub 4(34) | m/z = 503.17(C36H25NS = 503.66) |
| Sub 4(35) | m/z = 421.18(C32H23N = 421.53) | Sub 4(36) | m/z = 473.21(C36H27N = 473.61) |
| Sub 4(37) | m/z = 523.23(C40H29N = 523.66) | Sub 4(38) | m/z = 523.23(C40H29N = 523.66) |
| Sub 4(39) | m/z = 421.18(C32H23N = 421.53) | Sub 4(40) | m/z = 321.15(C24H19N = 321.41) |

Synthesis Example of Sub 5
The examples of Sub 5 of Reaction Scheme 4 include, but are not limited to, the followings.
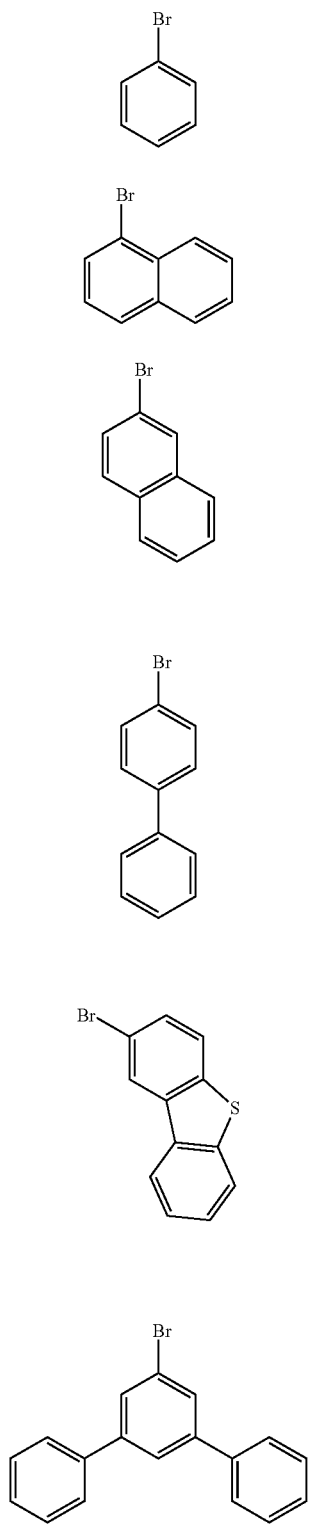
Sub 5(1)
Sub 5(2)
Sub 5(3)
Sub 5(4)
Sub 5(5)
Sub 5(6)
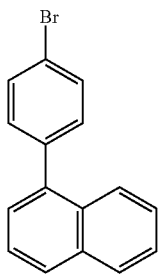
Sub 5(7)
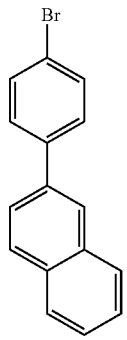
Sub 5(8)
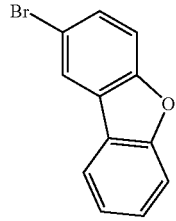
Sub 5(9)
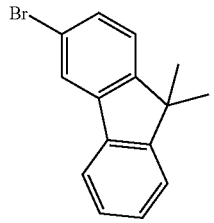
Sub 5(10)
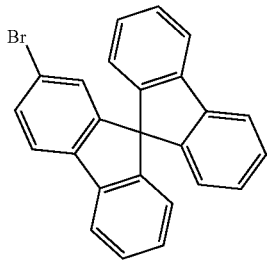
Sub 5(11)

Synthesis of Final Product 2

Synthesis Examples 2-34

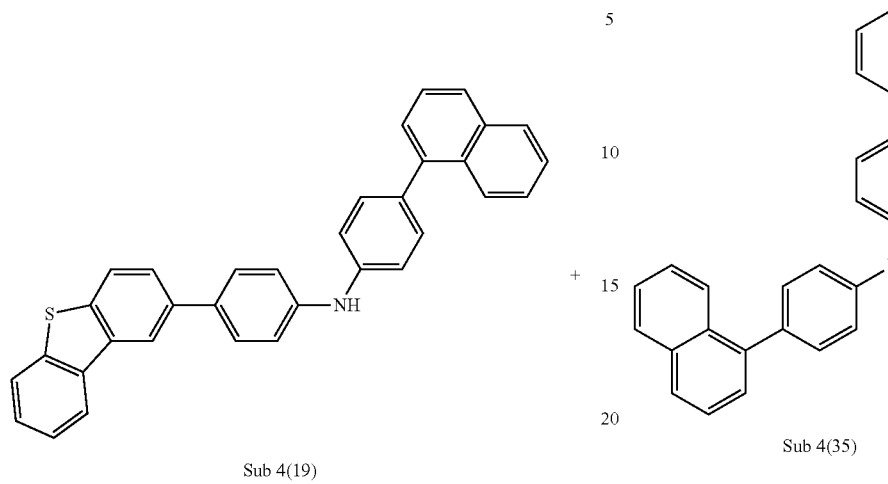

In a round-bottom flask, Sub 4 (19)(9.5 g, 20 mmol), Sub 5 (4)(4.7 g, 20 mmol), Pd$_2$(dba)$_3$ (0.5 g, 0.6 mmol), P(t-Bu)$_3$ (0.2 g, 2 mmol), t-BuONa (5.8 g, 60 mmol), and toluene (300 mL) were placed and allowed to react at 100° C. After completion of the reaction, the product was extracted with CH$_2$Cl$_2$ and water, and the extracted organic layer was dried with MgSO$_4$ and concentrated. And the product was purified by a silicagel column and recrystallized to give 9.8 g of 2-34 (yield:78%).

Synthesis Examples 2-58

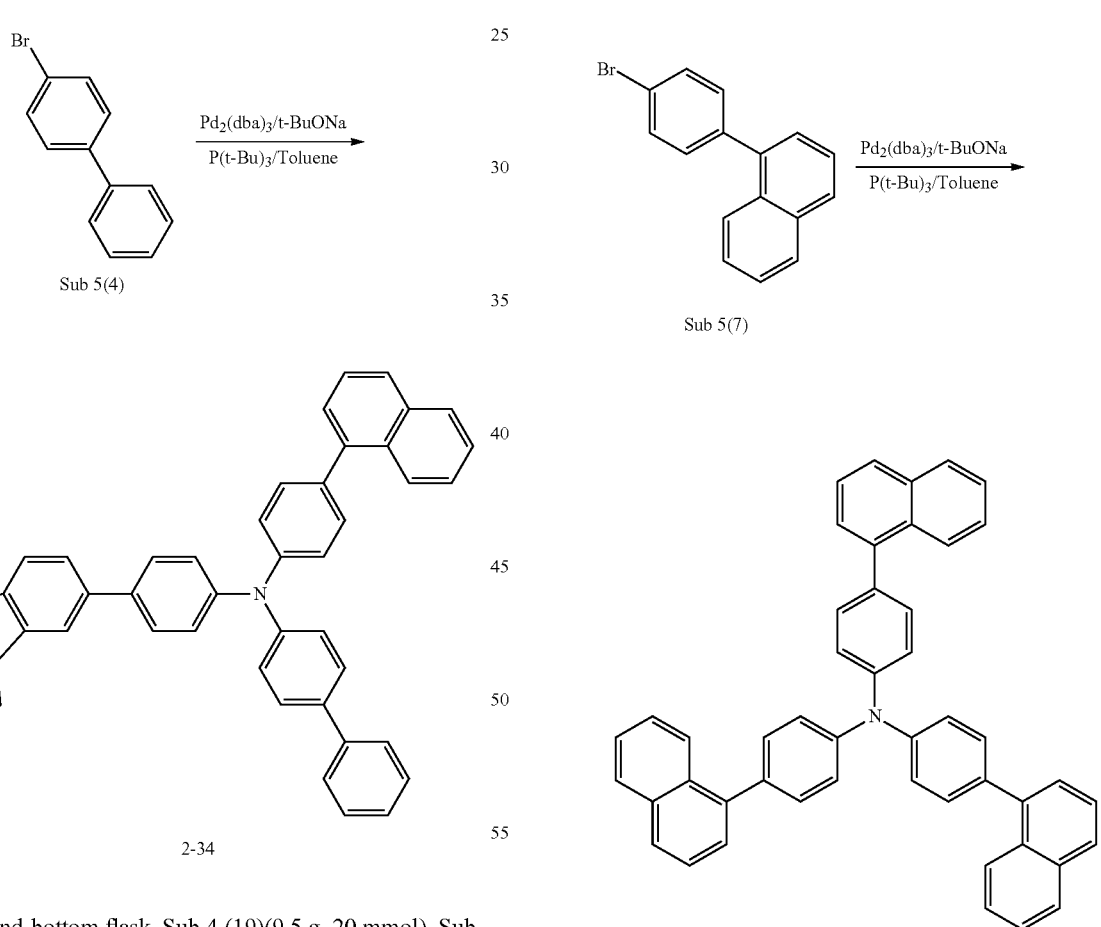

In a round-bottom flask, Sub 4 (35) 8.4 g, 20 mmol), Sub 5 (7)(5.7 g, 20 mmol), Pd$_2$(dba)$_3$ (0.5 g, 0.6 mmol), P(t-Bu)$_3$ (0.2 g, 2 mmol), t-BuONa (5.8 g, 60 mmol), and toluene (300 mL) were placed and using the synthetic method 2-34, to obtain the product of 2-58 10.4 g (yield:83%)

Synthesis Examples 2-59

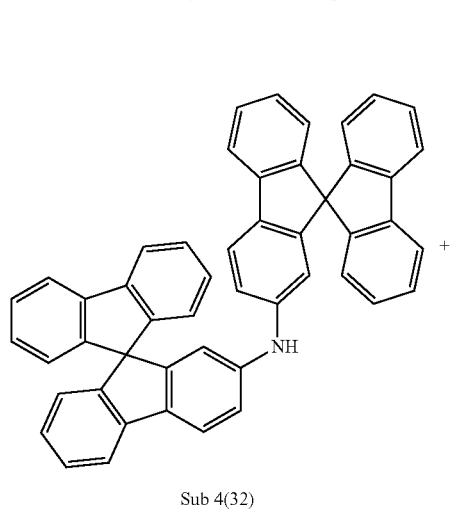

Sub 4(32)

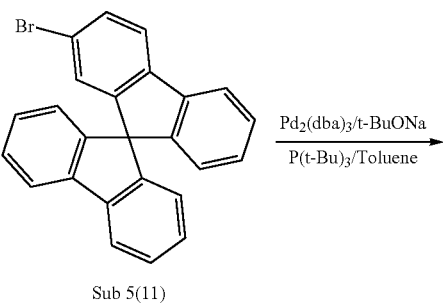

Sub 5(11)

Pd₂(dba)₃/t-BuONa
—————————————→
P(t-Bu)₃/Toluene

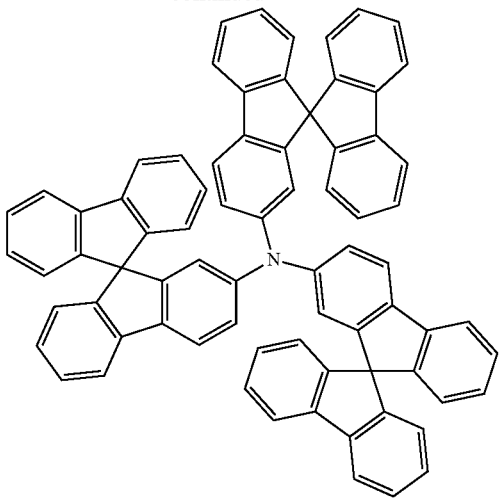

2-59

In a round-bottom flask, Sub 4 (32)(12.9 g, 20 mmol), Sub 5 (11)(7.9 g, 20 mmol), Pd2(dba)3 (0.5 g, 0.6 mmol), P(t-Bu)3 (0.2 g, 2 mmol), t-BuONa (5.8 g, 60 mmol), and toluene (300 mL) were placed and using the synthetic method of 2-34, to obtain the product of 2-59 5.2 g (yield: 79%)

TABLE 4

| compound | FD-MS | compound | FD-MS |
|---|---|---|---|
| 2-1 | m/z = 473.21(C36H27N = 473.61) | 2-2 | m/z = 660.26(C48H28D5NS = 660.88) |
| 2-3 | m/z = 644.29(C48H28D5NO = 644.81) | 2-4 | m/z = 644.29(C48H28D5NO = 644.81) |
| 2-5 | m/z = 660.26(C48H28D5NS = 660.88) | 2-6 | m/z = 821.28(C60H39NOS = 822.02) |
| 2-7 | m/z = 669.21(C48H31NOS = 669.83) | 2-8 | m/z = 669.21(C48H31NOS = 669.83) |
| 2-9 | m/z = 821.28(C60H39NOS = 822.02) | 2-10 | m/z = 821.28(C60H39NOS = 822.02) |
| 2-11 | m/z = 761.22(C54H35NS2 = 761.99) | 2-12 | m/z = 685.19(C48H31NS2 = 685.90) |
| 2-13 | m/z = 685.19(C48H31NS2 = 685.90) | 2-14 | m/z = 837.25(C60H39NS2 = 838.09) |
| 2-15 | m/z = 761.22(C54H35NS2 = 761.99) | 2-16 | m/z = 837.25(C60H39NS2 = 838.09) |
| 2-17 | m/z = 669.21(C48H31NOS = 669.83) | 2-18 | m/z = 669.21(C48H31NOS = 669.83) |
| 2-19 | m/z = 669.21(C48H31NOS = 669.83) | 2-20 | m/z = 821.28(C60H39NOS = 822.02) |
| 2-21 | m/z = 684.32(C51H32D5NO = 684.88) | 2-22 | m/z = 700.30(C51H32D5NS = 700.94) |
| 2-23 | m/z = 695.26(C51H37NS = 695.91) | 2-24 | m/z = 608.29(C45H28D5NO = 608.78) |
| 2-25 | m/z = 817.28(C61H39NS = 818.03) | 2-26 | m/z = 629.22(C46H31NS = 629.81) |
| 2-27 | m/z = 741.25(C55H35NS = 741.94) | 2-28 | m/z = 725.27(C55H35NO = 725.87) |
| 2-29 | m/z = 629.22(C46H31NS = 629.81) | 2-30 | m/z = 725.27(C55H35NO = 725.87) |
| 2-31 | m/z = 791.26(C59H37NS = 792.00) | 2-32 | m/z = 791.26(C59H37NS = 792.00) |
| 2-33 | m/z = 847.24(C61H37NS2 = 848.08) | 2-34 | m/z = 629.22(C46H31NS = 629.81) |
| 2-35 | m/z = 791.26(C59H37NS = 792.00) | 2-36 | m/z = 613.24(C46H31NO = 613.74) |
| 2-37 | m/z = 613.24(C46H31NO = 613.74) | 2-38 | m/z = 613.24(C46H31NO = 613.74) |
| 2-39 | m/z = 613.24(C46H31NO = 613.74) | 2-40 | m/z = 797.22(C57H35NS2 = 798.02) |
| 2-41 | m/z = 797.22(C57H35NS2 = 798.02) | 2-42 | m/z = 741.25(C55H35NS = 741.94) |
| 2-43 | m/z = 741.25(C55H35NS = 741.94) | 2-44 | m/z = 665.22(C49H31NS = 665.84) |
| 2-45 | m/z = 695.17(C49H29NS2 = 695.89) | 2-46 | m/z = 695.17(C49H29NS2 = 695.89) |
| 2-47 | m/z = 563.08(C36H21NS3 = 563.75) | 2-48 | m/z = 735.29(C57H37N = 735.91) |
| 2-49 | m/z = 735.29(C57H37N = 735.91) | 2-50 | m/z = 635.26(C49H33N = 635.79) |
| 2-51 | m/z = 735.29(C57H37N = 735.91) | 2-52 | m/z = 797.31(C62H39N = 797.98) |
| 2-53 | m/z = 663.29(C51H37N = 663.85) | 2-54 | m/z = 623.26(C48H33N = 623.78) |
| 2-55 | m/z = 903.30(C68H41NS = 904.12) | 2-56 | m/z = 655.23(C48H33NS = 655.85) |
| 2-57 | m/z = 741.25(C55H35NS = 741.94) | 2-58 | m/z = 623.26(C48H33N = 623.78) |
| 2-59 | m/z = 959.36(C75H45N = 960.17) | 2-60 | m/z = 625.28(C48H35N = 625.80) |
| 2-61 | m/z = 679.23(C50H33NS = 679.87) | 2-62 | m/z = 675.29(C52H37N = 675.86) |
| 2-63 | m/z = 725.31(C56H39N = 725.92) | 2-64 | m/z = 725.31(C56H39N = 725.92) |
| 2-65 | m/z = 473.21(C36H27N = 473.61) | 2-66 | m/z = 623.26(C48H33N = 623.78) |
| 2-67 | m/z = 623.26(C48H33N = 623.78) | 2-68 | m/z = 473.21(C36H27N = 473.61) |

Manufacture and Evaluation of Organic Electronic Element

Example 1) Manufacture and Test of Blue OLED (EBL)

On an ITO layer (anode) formed on a glass substrate, 2-TNATA was vacuum deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum deposited on the hole injection layer to form a hole transport layer with a thickness of 60 nm. Then, the compound of the present invention was vacuum deposited on the hole transport layer to form an EBL with a thickness of 20 nm. On the EBL, an light emitting layer with a thickness of 30 nm was deposited using 9,10-di(naphthalen-2-yl)anthracene as a host doped with BD-052X (Idemitsukosan) as a dopant in a weight ratio of 96:4. (1,1'-bisphenyl)-4-olato)bis(2-methyl-8-quinolinolato)aluminum (hereinafter will be abbreviated as BAlq) was vacuum deposited to form a hole blocking layer with a thickness of 40 nm, and an electron transport layer was formed using tris(8-quinolinol)aluminum (hereinafter will be abbreviated as Alq3) to a thickness of 40 nm. After that, an alkali metal halide, LiF was deposited as an electron injection layer to a thickness of 0.2 nm, and Al was deposited as a cathode to a thickness of 150 nm to manufacture an OLED.

To the OLEDs which were manufactured in examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 500 cd/m$^2$. In the following table, the results on the manufacture of a device and evaluation are shown.

Comparative Example 1 and 2

Except for not using the emitting auxiliary layer, an OLED was manufactured in the same manner as described in the embodiment 1.

Comparative Example 3

Except for forming a hole transport layer using the compound 2-1 instead of the compound represented by Formula (1) and except for not using the emitting auxiliary layer and, an OLED was manufactured in the same manner as described in the embodiment 1.

TABLE 5

|  | compounds of the hole transport layer | compounds of the emitting auxiliary layer | Voltage | Current Density | Brightness (cd/m2) | Efficiency | Lifetime T (95) |
|---|---|---|---|---|---|---|---|
| Comparative Example (1) | compound (1-17) | — | 4.7 | 13.9 | 500.0 | 3.6 | 93.2 |
| Comparative Example (2) | compound (1-32) | — | 4.2 | 12.2 | 500.0 | 4.1 | 95.8 |
| Comparative Example (3) | compound (2-58) | — | 4.9 | 15.6 | 500.0 | 3.2 | 84.3 |
| Example (1) | compound (1-17) | compound (2-1) | 4.8 | 8.8 | 500.0 | 5.7 | 115.1 |
| Example (2) | compound (1-17) | compound (2-12) | 4.8 | 8.9 | 500.0 | 5.6 | 132.0 |
| Example (3) | compound (1-17) | compound (2-54) | 4.8 | 9.1 | 500.0 | 5.5 | 142.6 |
| Example (4) | compound (1-17) | compound (2-56) | 4.8 | 8.8 | 500.0 | 5.7 | 132.4 |
| Example (5) | compound (1-17) | compound (2-58) | 4.8 | 8.1 | 500.0 | 6.2 | 154.8 |
| Example (6) | compound (1-17) | compound (2-60) | 4.8 | 9.4 | 500.0 | 5.3 | 114.1 |
| Example (7) | compound (1-17) | compound (2-61) | 4.8 | 9.7 | 500.0 | 5.2 | 130.2 |
| Example (8) | compound (1-17) | compound (2-62) | 4.9 | 9.1 | 500.0 | 5.5 | 123.6 |
| Example (9) | compound (1-17) | compound (2-63) | 4.8 | 8.6 | 500.0 | 5.8 | 140.8 |
| Example (10) | compound (1-17) | compound (2-64) | 4.8 | 9.6 | 500.0 | 5.2 | 139.0 |
| Example (11) | compound (1-17) | compound (2-66) | 4.8 | 9.1 | 500.0 | 5.5 | 114.7 |
| Example (12) | compound (1-17) | compound (2-67) | 4.8 | 9.2 | 500.0 | 5.5 | 125.3 |
| Example (13) | compound (1-32) | compound (2-1) | 4.3 | 7.4 | 500.0 | 6.7 | 133.6 |
| Example (14) | compound (1-32) | compound (2-12) | 4.3 | 8.0 | 500.0 | 6.2 | 147.0 |
| Example (15) | compound (1-32) | compound (2-54) | 4.5 | 7.2 | 500.0 | 7.0 | 144.2 |
| Example (16) | compound (1-32) | compound (2-56) | 4.2 | 7.4 | 500.0 | 6.8 | 110.7 |
| Example (17) | compound (1-32) | compound (2-58) | 4.3 | 7.0 | 500.0 | 7.1 | 150.9 |
| Example (18) | compound (1-32) | compound (2-60) | 4.2 | 7.3 | 500.0 | 6.8 | 122.9 |
| Example (19) | compound (1-32) | compound (2-61) | 4.3 | 7.3 | 500.0 | 6.9 | 144.4 |
| Example (20) | compound (1-32) | compound (2-62) | 4.3 | 8.1 | 500.0 | 6.2 | 147.8 |
| Example (21) | compound (1-32) | compound (2-63) | 4.2 | 8.3 | 500.0 | 6.0 | 136.8 |
| Example22) | compound (1-32) | compound (2-64) | 4.4 | 8.0 | 500.0 | 6.3 | 138.6 |
| Example (23) | compound (1-32) | compound (2-66) | 4.4 | 7.4 | 500.0 | 6.8 | 127.7 |
| Example (24) | compound (1-32) | compound (2-67) | 4.4 | 7.2 | 500.0 | 7.0 | 138.0 |

Example 2) Manufacture and Test of Green Organic Light Emitting Diode

First, on an ITO layer (anode) formed on a glass substrate, N$^1$-(naphthalen-2-yl)-N$^4$,N$^4$-bis (4-(naphthalen-2-yl(phenyl)amino)phenyl)-N$^1$-phenylbenzene-1,4-diamine (hereinafter will be abbreviated as 2-TNATA) was vacuum-deposited to form a thickness of 60 nm, and subsequently, the inventive compound represented by the formula (1) was vacuum-deposited on the film as a hole transport compound to a thickness of 60 nm to form a hole transport layer. Then, the inventive compound represented by the formula (2) was vacuum-deposited as an emitting auxiliary layer material to a thickness of 20 nm to form an emitting auxiliary layer.

After forming the emitting auxiliary layer, CBP [4,4'-N, N'-dicarbazole-biphenyl] was used as a host on the emitting auxiliary layer, and Ir (ppy) 3 [tris (2-phenylpyridine)-iridium] was doped as a dopant at a weight ratio of 95:5 to deposit an emitting layer with a thickness of 30 nm on the emitting auxiliary layer. (1,1'-bisphenyl)-4-olato)bis(2-methyl-8-quinolinolato) aluminum (hereinafter will be abbreviated as BAlq) was vacuum deposited to form a hole blocking layer with a thickness of 10 nm, and Tris (8-quinolinol) aluminum (hereinafter abbreviated as Alq3) was deposited to a thickness of 40 nm as an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

To the OLEDs which were manufactured in examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 5000 cd/m$^2$. In the following table, the results on the manufacture of a device and evaluation are shown.

Comparative Example 4, 5

Except for not using the emitting auxiliary layer, an OLED was manufactured in the same manner as described in the embodiment 1 above.

Comparative Example 6

Except for forming a hole transport layer using the compound 2-1 instead of the compound represented by Formula (1) and except for not using the emitting auxiliary layer and, an OLED was manufactured in the same manner as described in the embodiment 1.

transport layer, and the compound of the Formula (2) is used as the emitting auxiliary layer, the efficiency and the lifetime were remarkably improved, even though the driving voltage was about the same or slightly higher, than that of the comparative example using the compound of formula (1) as the hole transport layer without using the luminescent auxiliary layer.

Further, comparing the comparative examples (1), (2), (4), and (5) without emitting auxiliary layer, wherein the compound 1-17 and 1-32 represented by the formula (1) were respectively used as the hole transport layer, and the examples (1) to (24), (25), and (48) using the compound represented by Formula (2), it can be seen that the efficiency and the life span are remarkably improved. This is because when the compound of the present invention is used as an emitting auxiliary layer, due to the deep HOMO energy levels inherent to the inventive compounds, a suitable amount of holes in the emitting layer can be efficiently transferred from the hole transport layer, and the holes and electrons in the emitting layer make a charge balance and it is considered that the interface deterioration at the interface of the emitting layer are prevented and the efficiency and life span are increased. Also, as the charge balance in the emitting layer increases, the surplus polaron in the emitting layer decreases, and the light emitting material deformation decreases, it is considered that color purity improvement, life span, and efficiency increase.

As can be seen from the results of Comparative Examples (3) or (6) and Examples (1) to (24), (25) and (48), when the compound represented by the formula (2) is used alone as the hole transport layer, the efficiency and the life span were lower than that of the example using the compound of

TABLE 6

| | compounds of the hole transport layer | compounds of the emitting auxiliary layer | Voltage | Current Density | Brightness (cd/m2) | Efficiency | Lifetime T (95) |
|---|---|---|---|---|---|---|---|
| comparative example (4) | compound (1-17) | — | 5.5 | 17.9 | 5000.0 | 28.0 | 93.0 |
| comparative example (5) | compound (1-32) | — | 5.0 | 14.3 | 5000.0 | 35.0 | 97.3 |
| comparative example (6) | compound (2-58) | — | 5.8 | 20.0 | 5000.0 | 25.0 | 89.1 |
| example (25) | compound (1-17) | compound (2-7) | 5.6 | 13.5 | 5000.0 | 37.1 | 148.2 |
| example (26) | compound (1-17) | compound (2-12) | 5.5 | 13.7 | 5000.0 | 36.5 | 110.9 |
| example (27) | compound (1-17) | compound (2-54) | 5.5 | 13.9 | 5000.0 | 36.1 | 117.8 |
| example (28) | compound (1-17) | compound (2-56) | 5.6 | 12.2 | 5000.0 | 41.0 | 111.5 |
| example (29) | compound (1-17) | compound (2-58) | 5.7 | 11.2 | 5000.0 | 44.5 | 135.3 |
| example (30) | compound (1-17) | compound (2-60) | 5.7 | 11.2 | 5000.0 | 44.5 | 137.0 |
| example (31) | compound (1-17) | compound (2-61) | 5.7 | 12.8 | 5000.0 | 39.1 | 150.0 |
| example (32) | compound (1-17) | compound (2-62) | 5.7 | 12.2 | 5000.0 | 40.9 | 125.4 |
| example (33) | compound (1-17) | compound (2-63) | 5.7 | 12.0 | 5000.0 | 41.6 | 130.8 |
| example (34) | compound (1-17) | compound (2-64) | 5.5 | 13.5 | 5000.0 | 37.1 | 122.1 |
| example (35) | compound (1-17) | compound (2-66) | 5.8 | 11.9 | 5000.0 | 42.2 | 143.4 |
| example (36) | compound (1-17) | compound (2-67) | 5.6 | 11.8 | 5000.0 | 42.3 | 115.5 |
| example (37) | compound (1-32) | compound (2-7) | 5.2 | 11.1 | 5000.0 | 44.9 | 116.0 |
| example (38) | compound (1-32) | compound (2-12) | 5.1 | 11.8 | 5000.0 | 42.5 | 125.2 |
| example (39) | compound (1-32) | compound (2-54) | 5.2 | 13.2 | 5000.0 | 38.0 | 132.4 |
| example (40) | compound (1-32) | compound (2-56) | 5.1 | 13.8 | 5000.0 | 36.1 | 138.3 |
| example (41) | compound (1-32) | compound (2-58) | 5.1 | 12.7 | 5000.0 | 39.3 | 132.6 |
| example (42) | compound (1-32) | compound (2-60) | 5.2 | 11.4 | 5000.0 | 43.8 | 122.0 |
| example (43) | compound (1-32) | compound (2-61) | 5.3 | 14.3 | 5000.0 | 35.0 | 146.0 |
| example (44) | compound (1-32) | compound (2-62) | 5.1 | 12.7 | 5000.0 | 39.5 | 145.3 |
| example (45) | compound (1-32) | compound (2-63) | 5.0 | 11.6 | 5000.0 | 43.2 | 113.9 |
| example (46) | compound (1-32) | compound (2-64) | 5.3 | 13.1 | 5000.0 | 38.1 | 139.5 |
| example (47) | compound (1-32) | compound (2-66) | 5.2 | 14.1 | 5000.0 | 35.6 | 131.6 |
| example (48) | compound (1-32) | compound (2-67) | 5.3 | 14.2 | 5000.0 | 35.2 | 133.2 |

As can be seen from the results of Table 5 and Table 6, when the compound of the Formula (1) is used as the hole formula (1) as the hole transporting layer, but it can be confirmed that excellent results are obtained in efficiency and life span when used as an emitting auxiliary layer. That is, unlike the case of using the compound of formula (2) as the hole transport layer, the result of the device was improved when used as the emitting auxiliary layer, and this indicates that the characteristics of the device can be significantly changed by using a compound in a specific layer, in particular, it shows that the performance varies depending on the combination of the hole transport layer material and the emitting auxiliary layer material.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

The invention claimed is:

1. An organic electronic element comprising:
a first electrode, a second electrode, and an organic layer formed between the first electrode and the second electrode, wherein the organic material layer includes an emitting auxiliary layer formed between the first electrode and the emitting layer, and a hole transport layer formed between the first electrode and the emitting auxiliary layer, wherein the hole transport layer contains a compound represented by the following Formula (1), and the emitting auxiliary layer contains a compound represented by the following Formula (2),

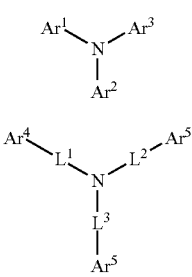

in Formulas (1) and (2), $Ar^1$, $Ar^2$, $Ar^4$, $Ar^5$ and $Ar^6$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$alkyl group; a $C_2$-$C_{20}$ aklenyl group; a $C_2$-$C_{20}$ alkynyl group; a $C_1$-$C_{30}$ alkoxyl group; a $C_6$-$C_{30}$ aryloxy group; and -L'-N($R_a$)($R_b$) (where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring;

and a $C_2$-$C_{60}$ heterocyclic group containing at least one heteroatom of O, N, S, Si, or P), and
$Ar^3$ is at least one of the Formula (1-a) or Formula (1-b) below,

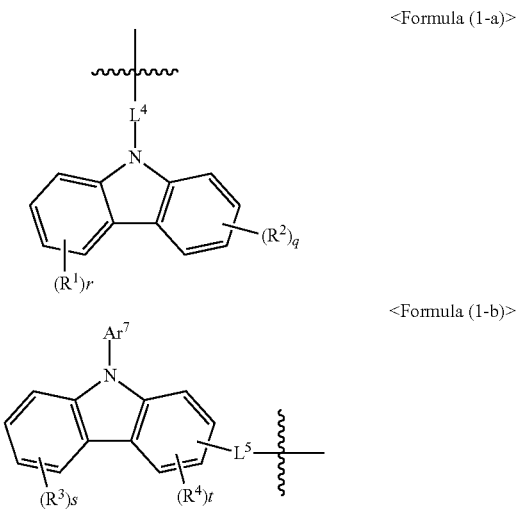

wherein q, r and s are each an integer of 0 to 4, t is an integer of 0 to 3, and $R^1$, $R^2$, $R^3$, $R^4$ are the same or different, and are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$) ($R_b$) (wherein, L', $R_a$ and $R_b$ are the same as indicated above), wherein in case q, r and s are each an integer of 2 or more, $R^1$, $R^2$ and $R^3$ are each in plural and are the same or different, and a plurality of $R^1$ or a plurality of $R^2$ or a plurality of $R^3$ or a plurality of $R^4$ may combine to each other to form a ring, and
$L^4$ is selected from the group consisting of a $C_6$-$C_{60}$ arylene group, and a fluorenylene group; a fused ring group of a $C_3$-$C_{60}$ aliphatic ring and a $C_6$-$C_{60}$ aromatic ring; and a $C_2$-$C_{60}$ heterocyclic group including at least one heteroatom of O, N, S, Si or P, and
$L^5$ is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group including at least one heteroatom of O, N, S, Si or P, and
$Ar^7$ is independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$) (wherein, L', $R_a$ and $R_b$ are as defined above), and
$L^1$, $L^2$ and $L^3$ are selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P, wherein the aryl group, fluorenyl group, heterocyclic group, fused ring group, alkyl group, alkenyl group, alkynyl group, alkoxyl group, aryloxy group, arylene group and fluorenylene group may be substituted with one or more substituents selected from the group consisting of deuterium; halogen; a silane group; a siloxane group; boron group; a germanium group; a cyano group; a nitro group; -L'-N($R_a$)($R_b$); a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{60}$ aryl group; a $C_6$-$C_{60}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group, wherein the substituents may combine each other to form a saturated or unsaturated ring selected from the group consisting of a $C_3$-$C_{60}$ aliphatic ring, a $C_6$-$C_{60}$ aromatic ring, a $C_2$-$C_{60}$ heterocyclic ring, and a fused ring formed by the combination thereof.

2. The organic electronic element according to claim 1, wherein the compound represented by the Formula (1) is one of compounds of the following Formulas (3) to (4),

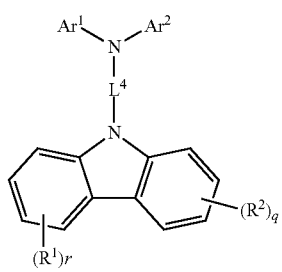
<Formula (3)>

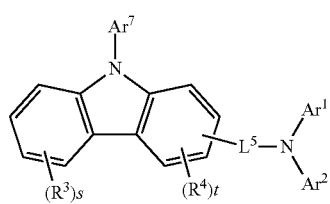
<Formula (4)> in Formula (3) and Formula (4), $R^1$, $R^2$, $R^3$, $R^4$, $L^4$, $L^5$, $Ar^1$, $Ar^2$, $Ar^7$, q, r, s, and t are the same as defined in claim 1.

3. The organic electronic element according to claim 1, wherein the compound represented by the Formula (1) is one of compounds represented by the following of Formula (5) to Formula (7),

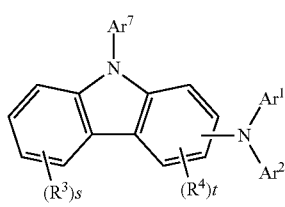
<Formula (5)>

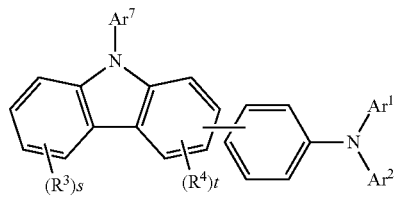
<Formula (6)>

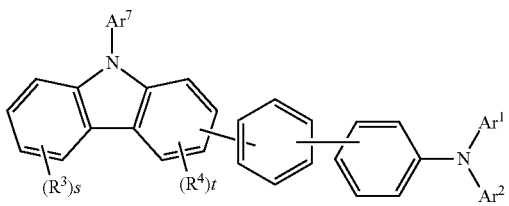
<Formula (7)> in Formula (5), Formula (6) and Formula (7), $R^3$, $R^4$, $Ar^1$, $Ar^2$, $Ar^7$, s, and t are the same as defined in claim 1.

4. The organic electronic element according to claim 1, wherein the compound represented by the Formula (2) of the emission-auxiliary layer is one of compounds of Formula (8) to Formula (12) below,

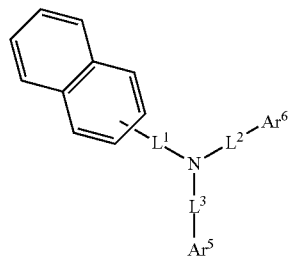
<Formula (8)>

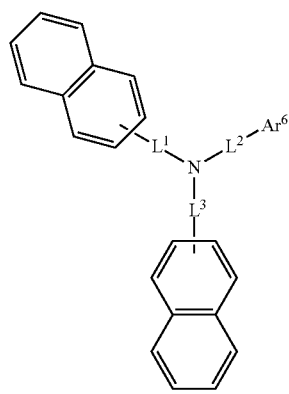
<Formula (9)>

105

-continued

<Formula (10)>

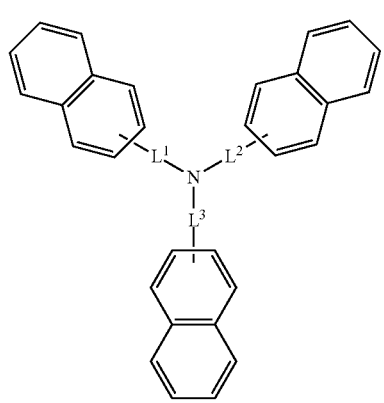

<Formula (11)>

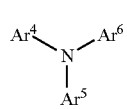

<Formula (12)>

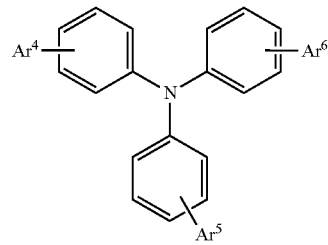

in Formula (8), Formula (9), Formula (10), Formula (11) and Formula (12), $L^1$, $L^2$, $L^3$, $Ar^4$, $Ar^5$, and $Ar^6$ are the same as defined in claim 1.

5. The organic electronic element according to claim 1, wherein $L^1$, $L^2$, $L^3$, and $L^5$ in the compounds represented by the Formula (1) and the Formula (2) are a single bond, or $L^1$, $L^2$, $L^3$, $L^4$ and $L^5$ are represented by the following Formulas,

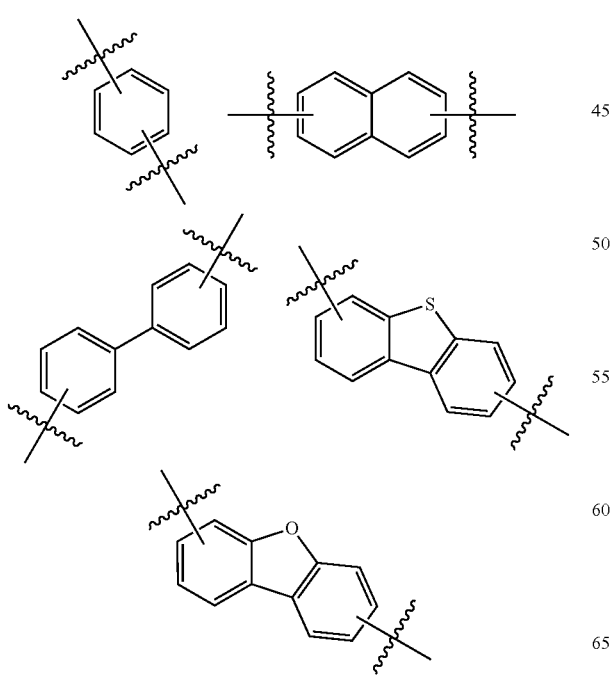

106

-continued

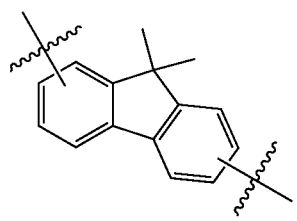

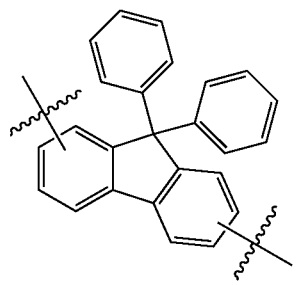

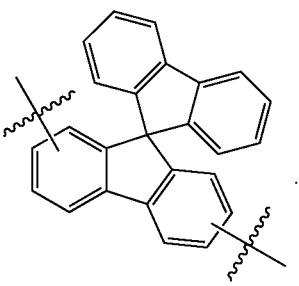

6. The organic electronic element according to claim 2, wherein the compounds represented by the formula (1) of the hole transport layer or by the Formulas (3) to (7) are one of the following compounds, 1-1

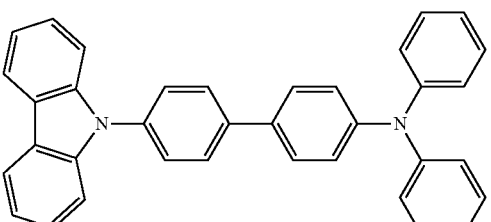

1-2

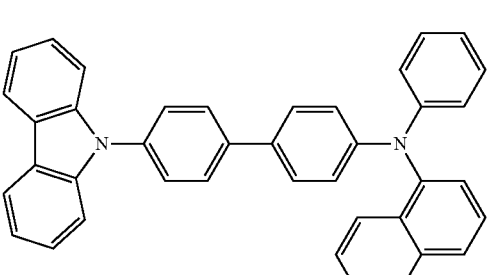

1-3
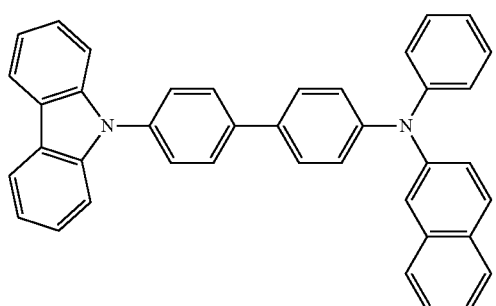
1-4
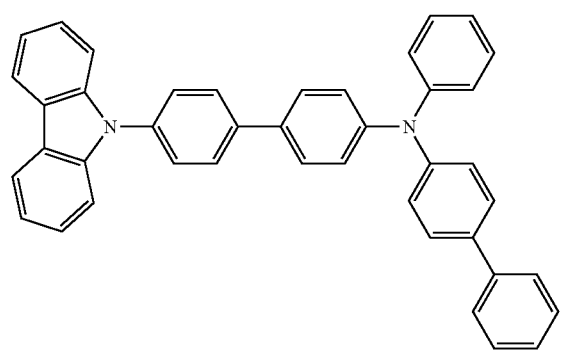
1-5
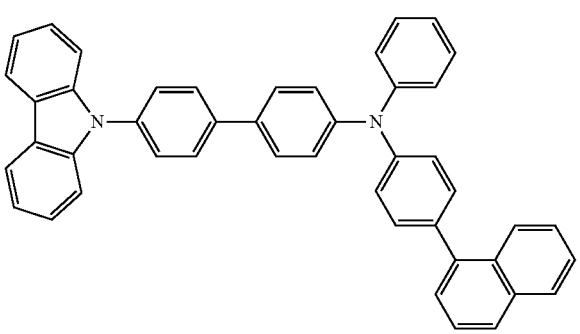
1-6
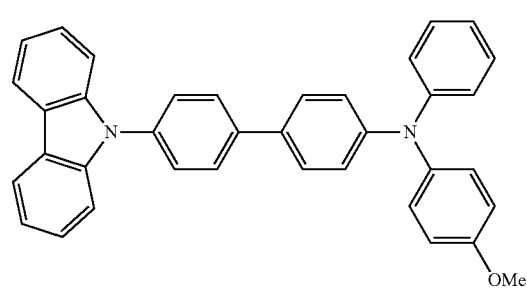
1-7
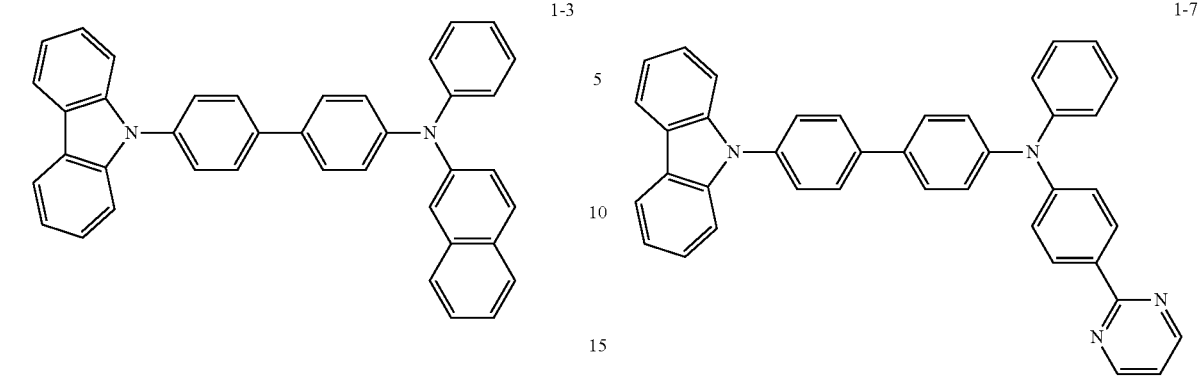
1-8
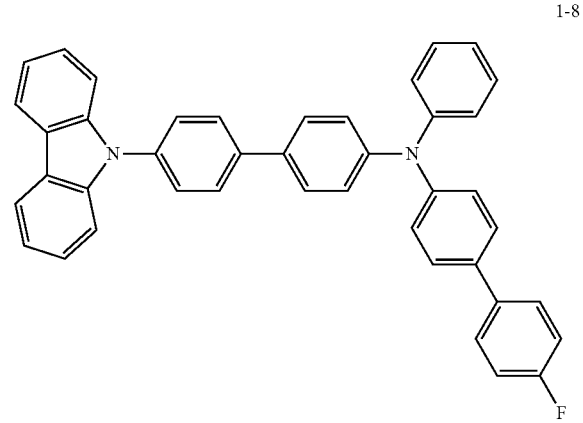
1-9
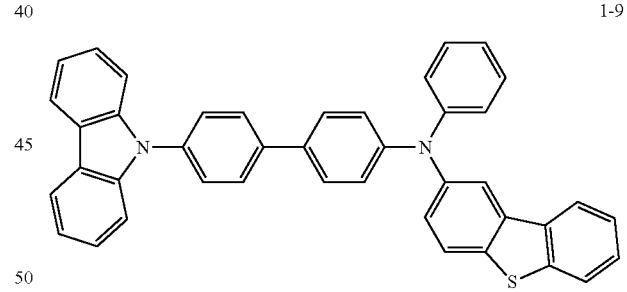
1-10
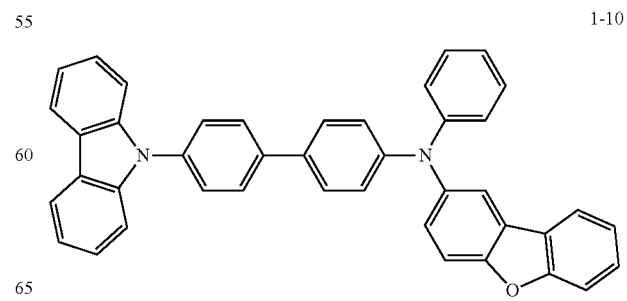

1-11
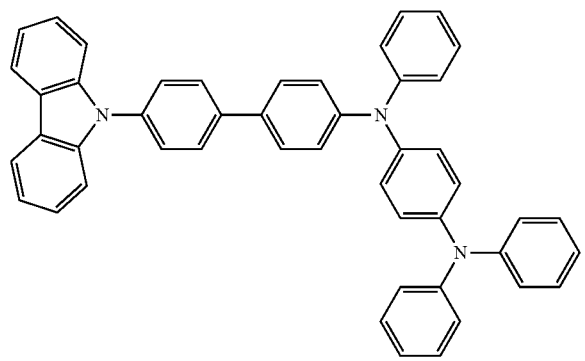
1-12
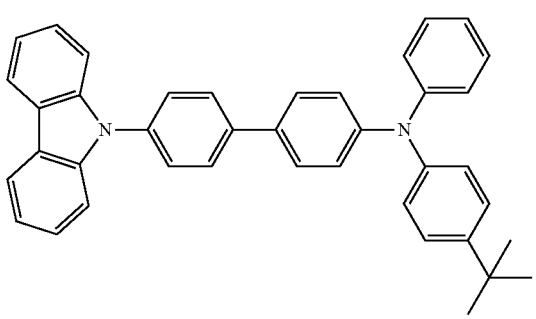
1-13
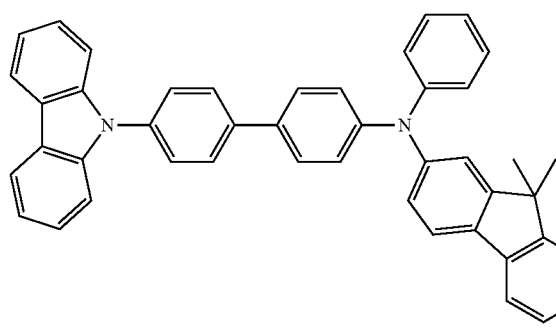
1-14
1-15
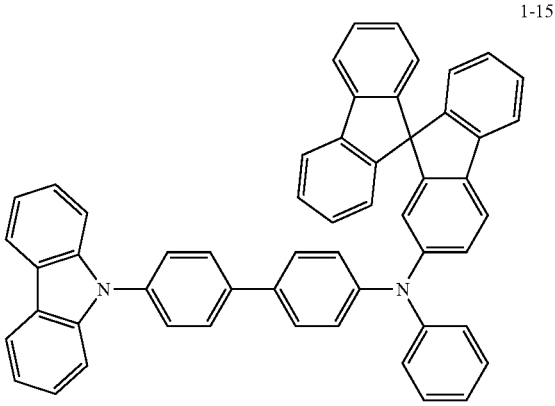
1-16
1-17
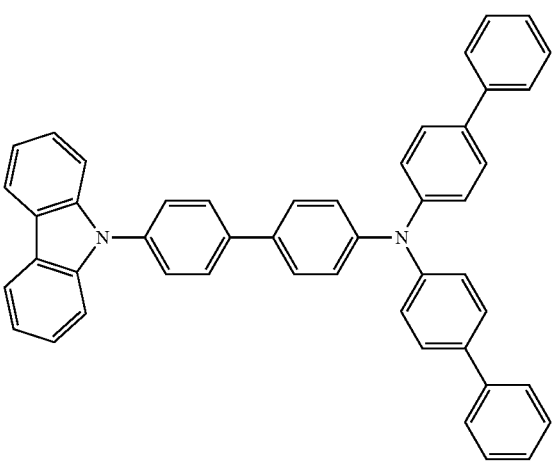

-continued
1-18
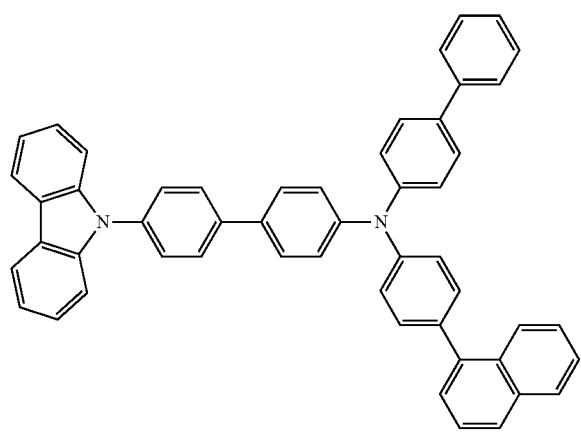
1-19
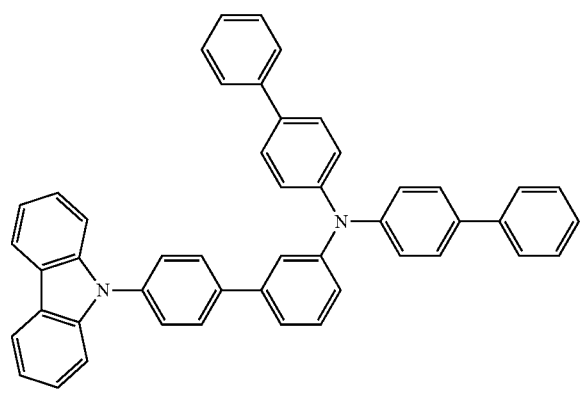
1-20
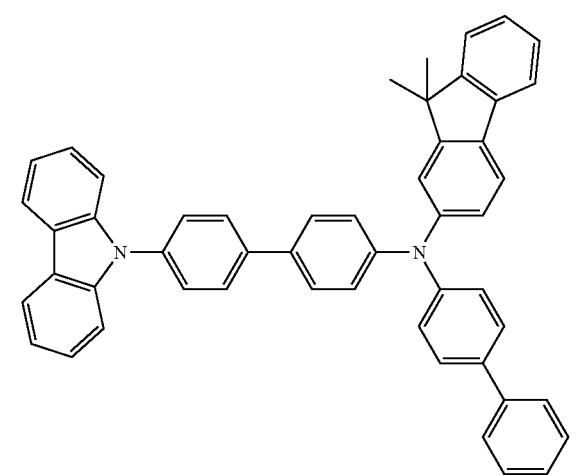
-continued
1-21
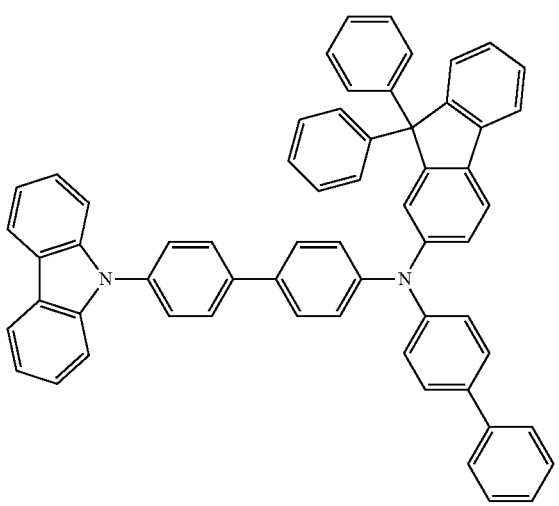
1-22
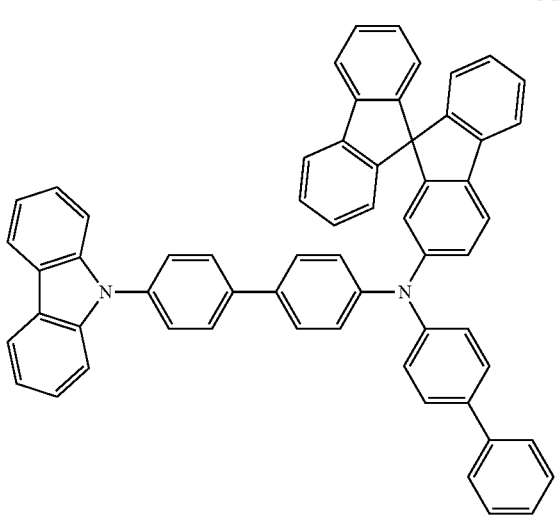
1-23

1-24
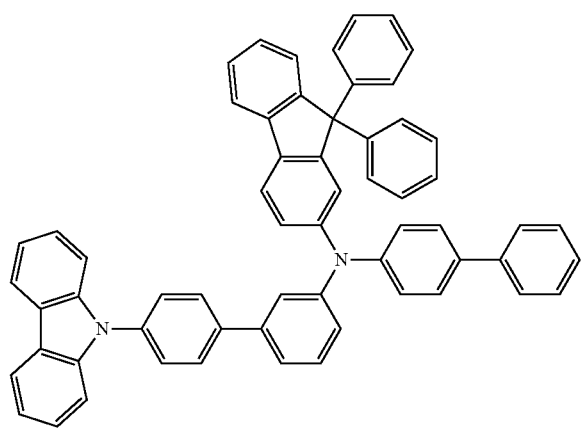
1-25
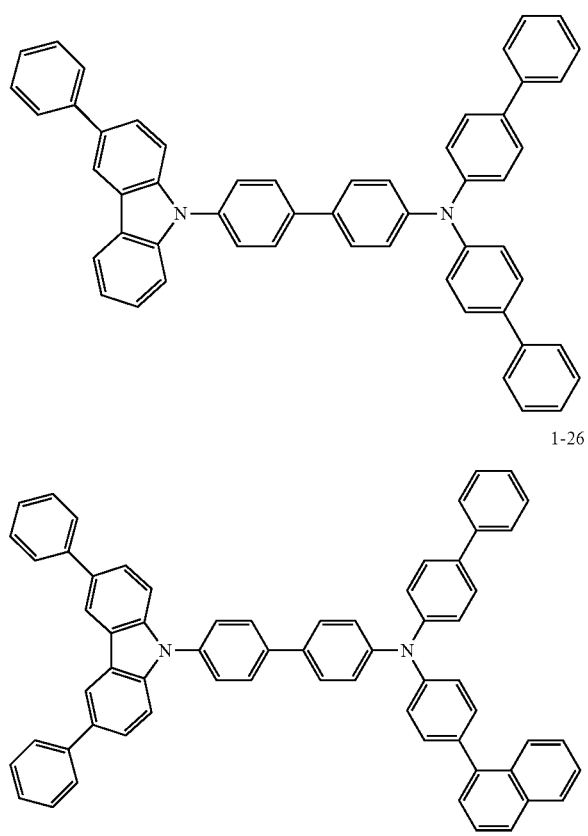
1-26
1-27
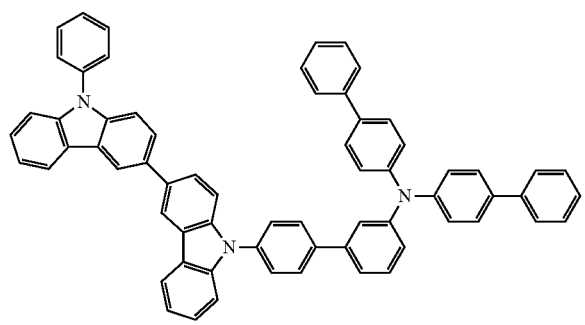
1-28
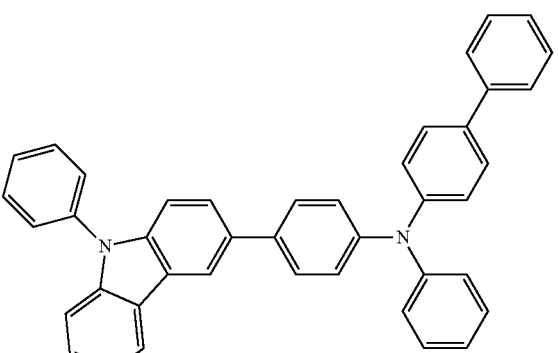
1-29
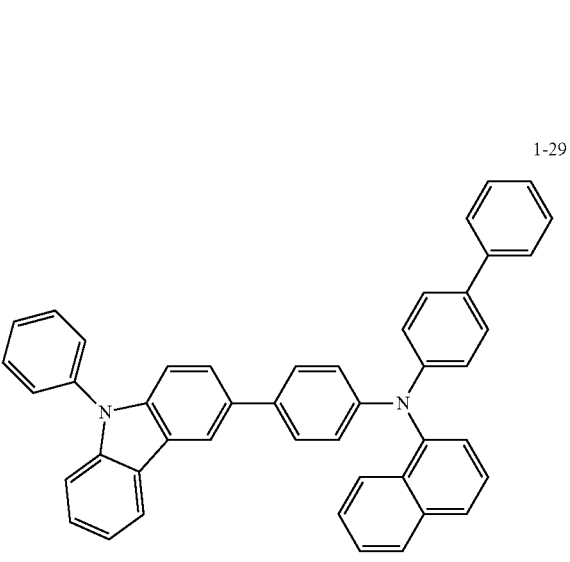
1-30
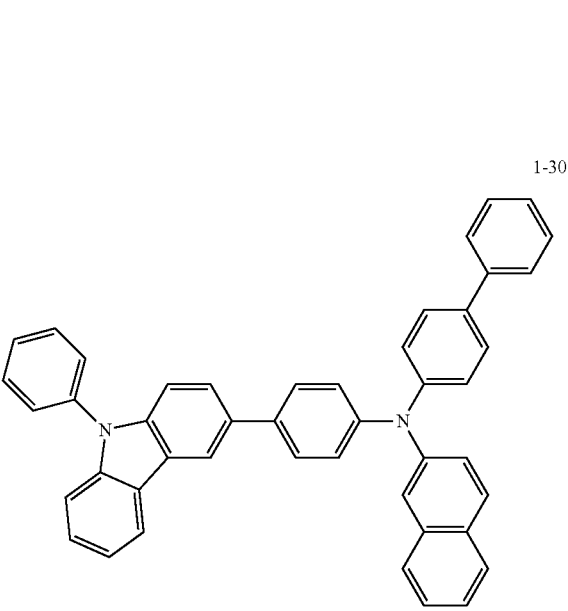

1-31
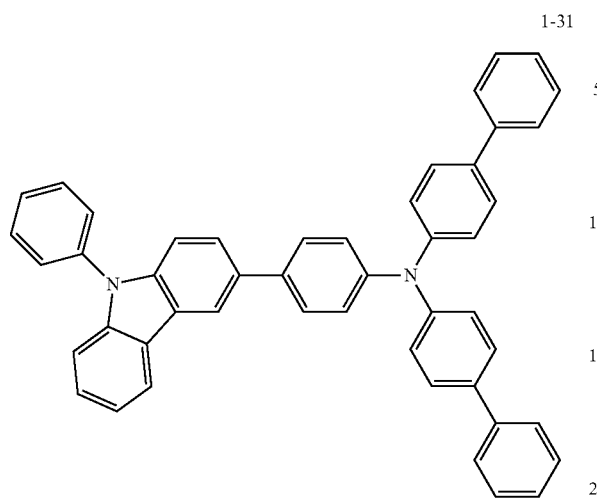
1-32
1-33
1-34
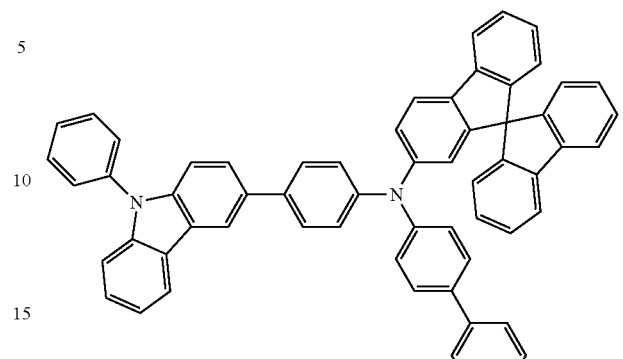
1-35
1-36
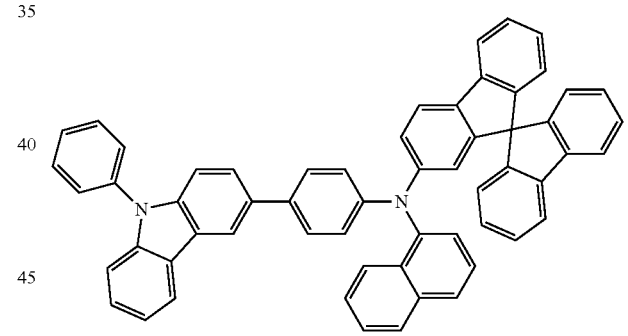
1-37
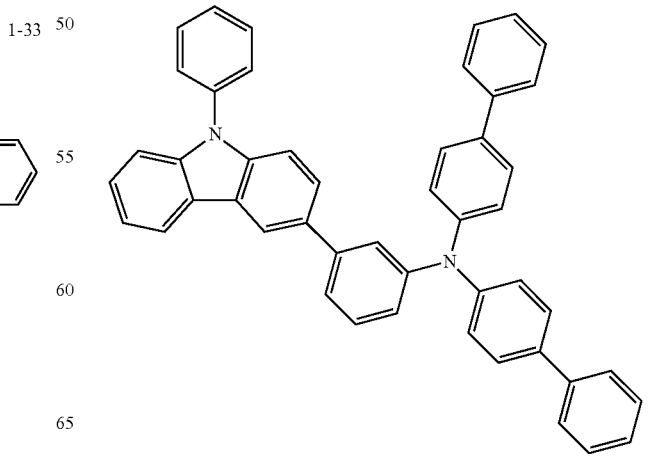

1-38
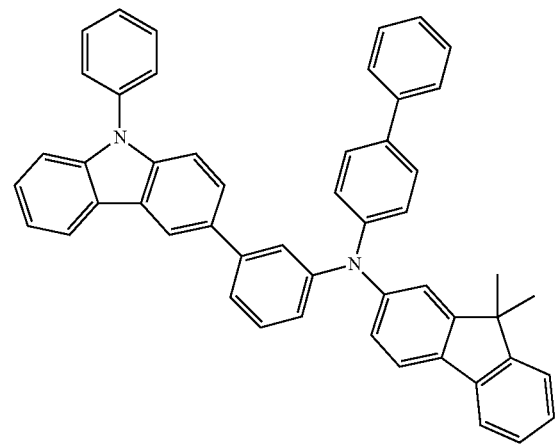
1-39
1-40
1-41
1-42
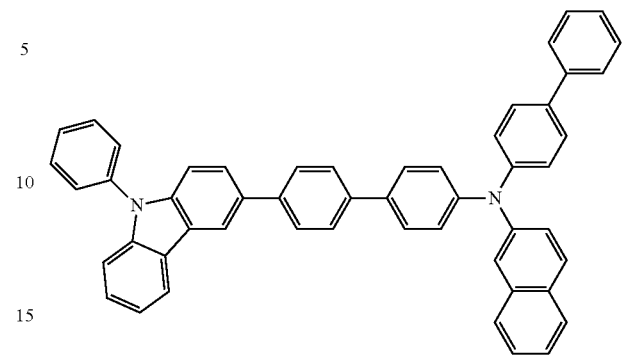
1-43
1-44
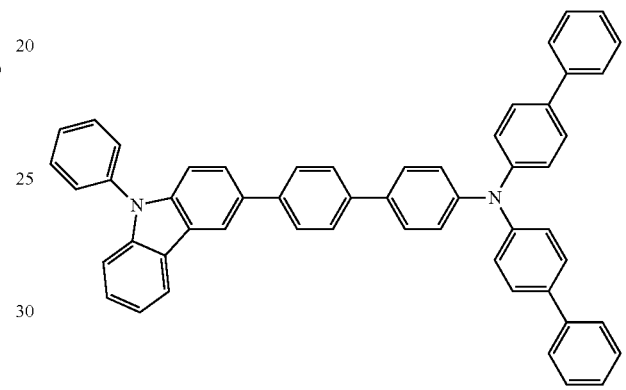
1-45
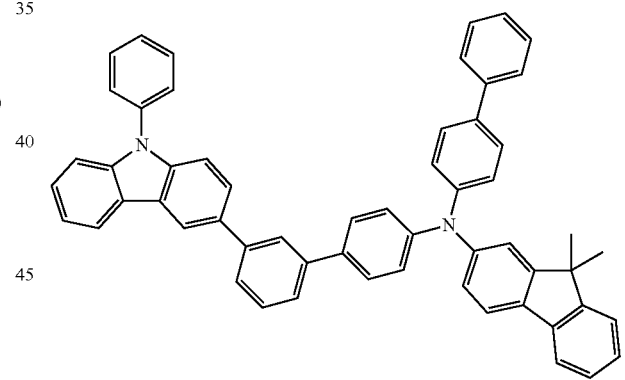
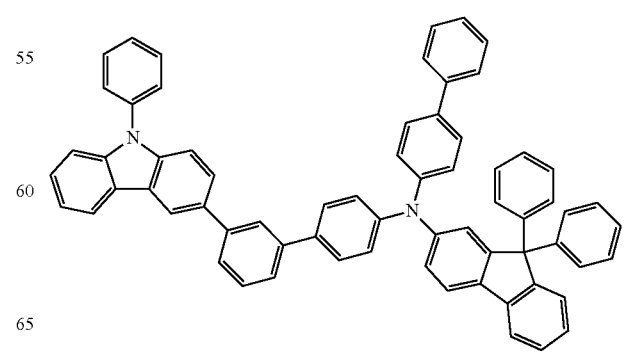

1-46
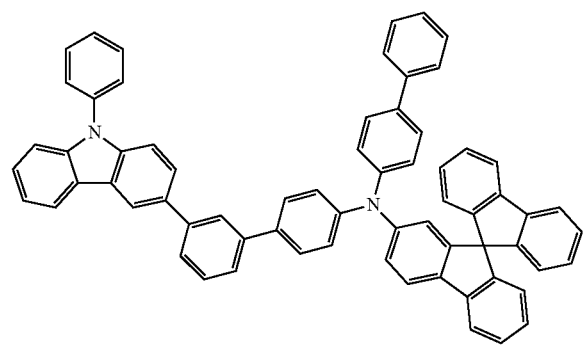
1-47
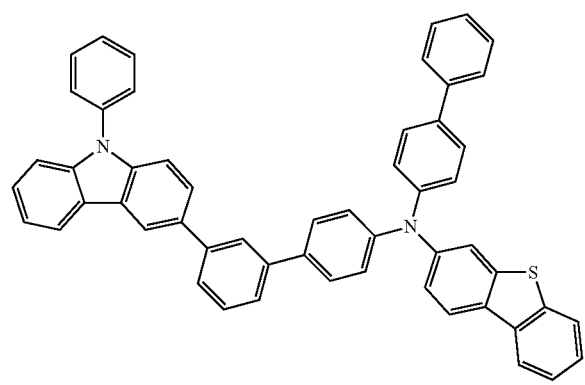
1-48
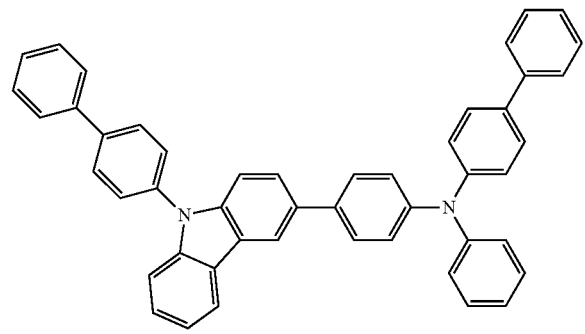
1-49
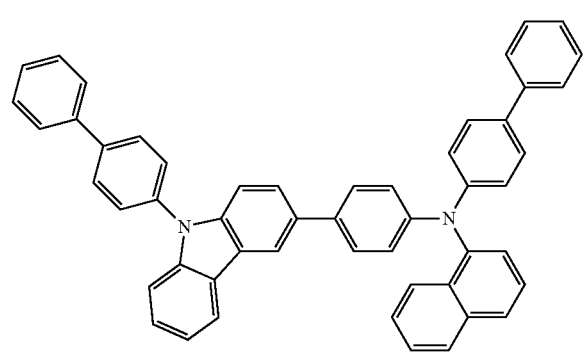
1-50
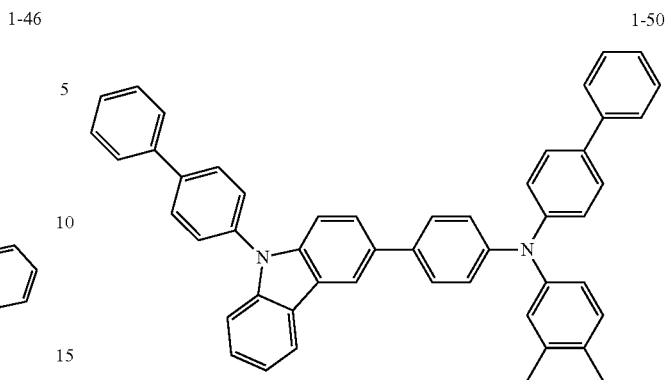
1-51
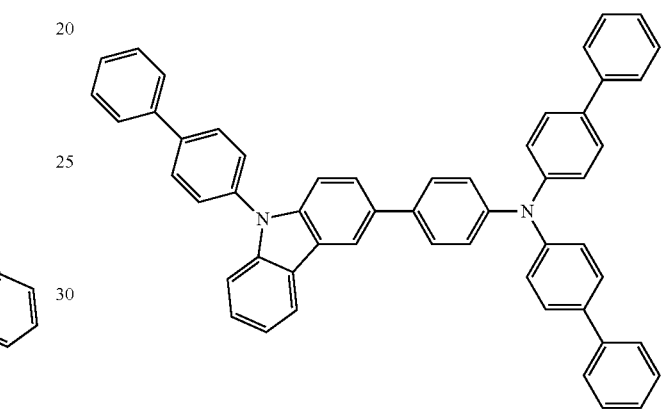
1-52
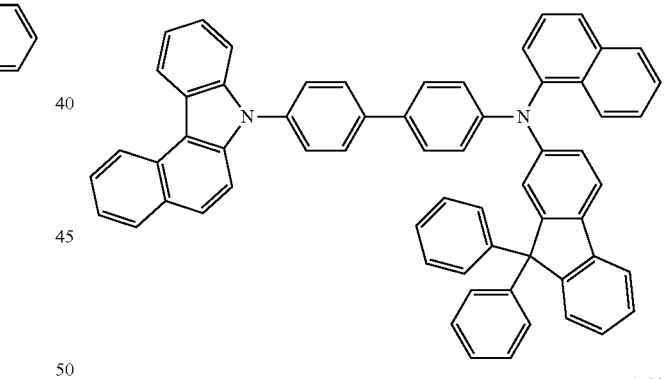
1-53
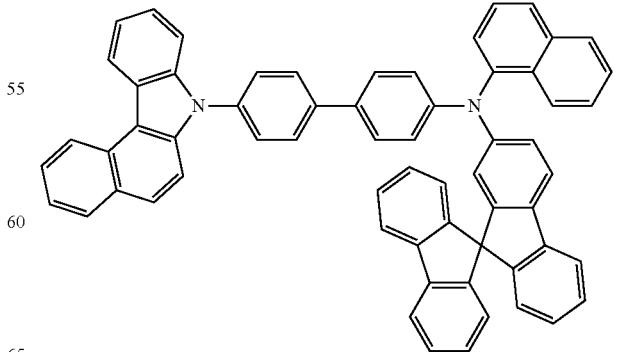

1-54
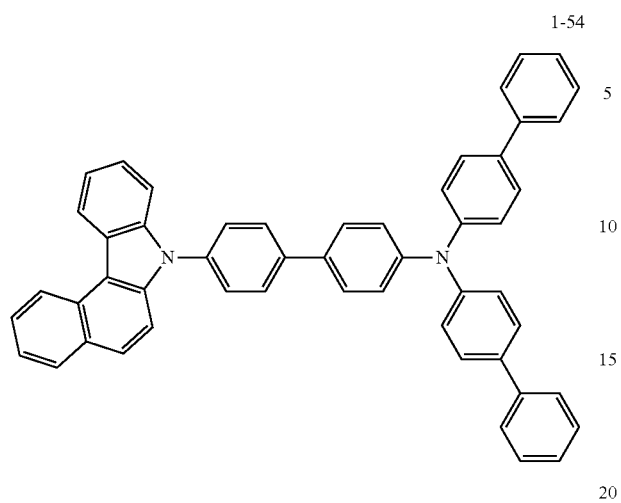
1-57
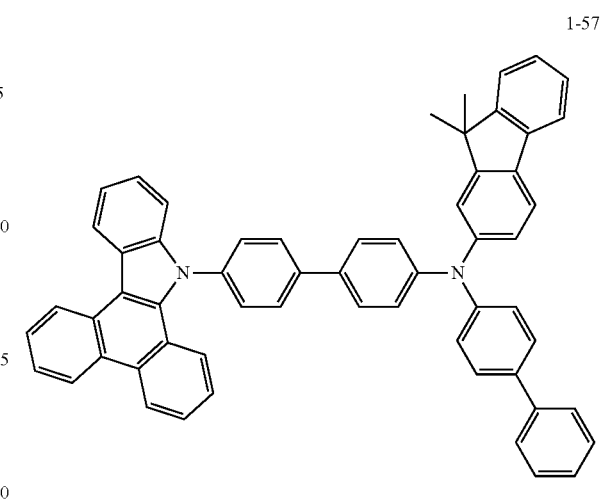
1-55
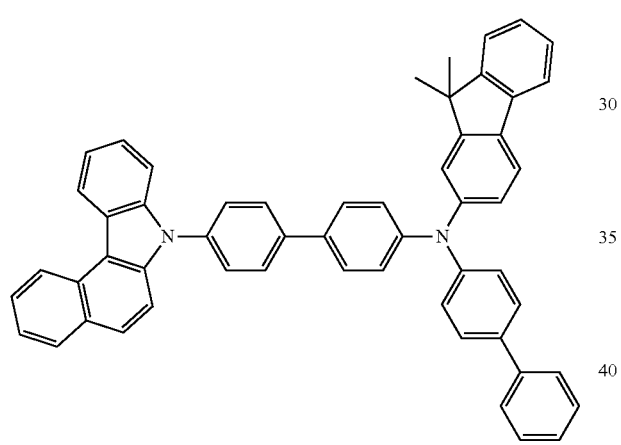
1-58
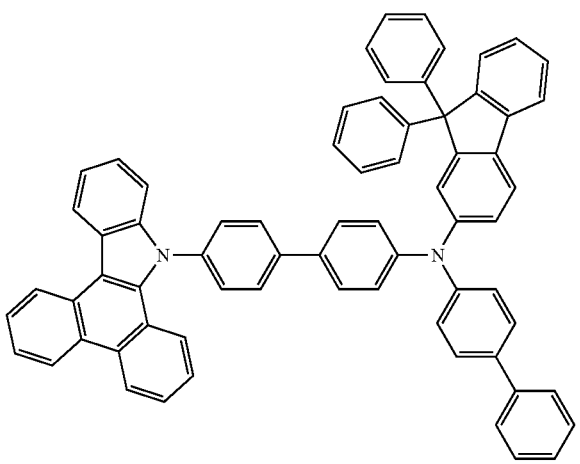
1-56
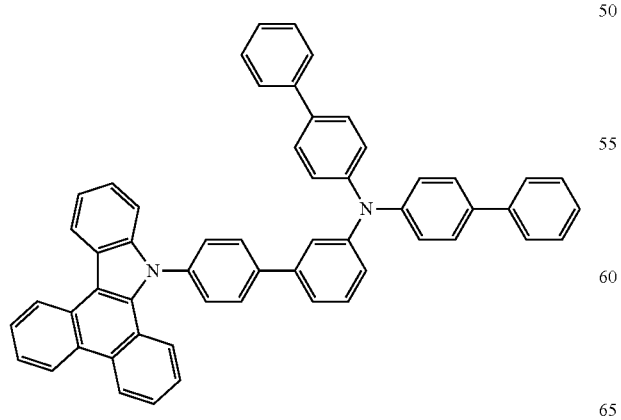
1-59
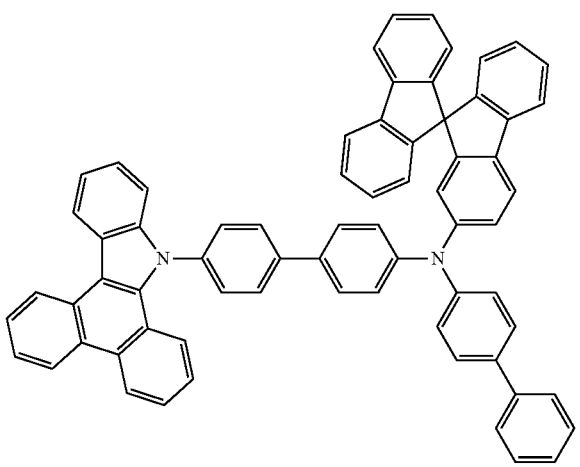

-continued
1-60
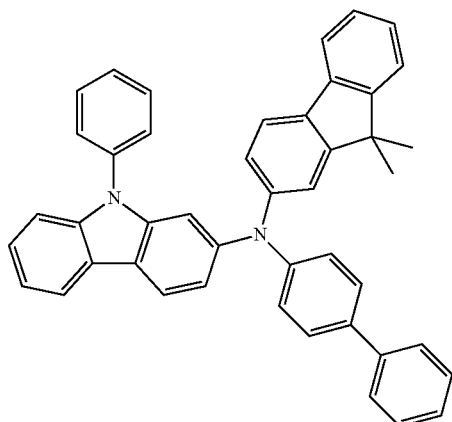
1-61
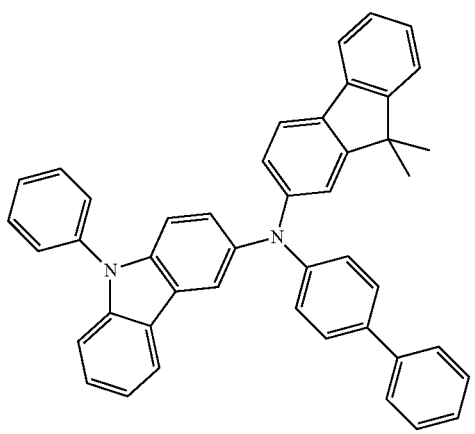
1-62
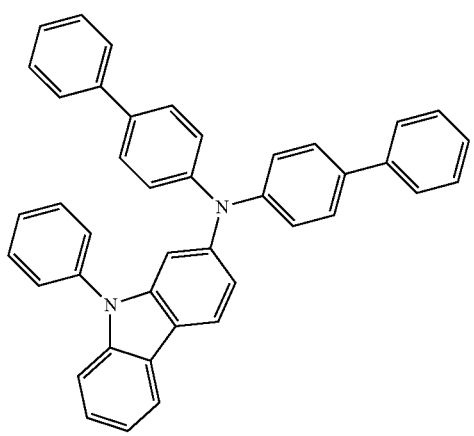
-continued
1-63
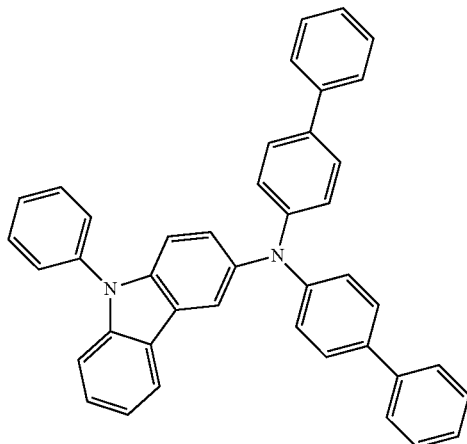
1-64
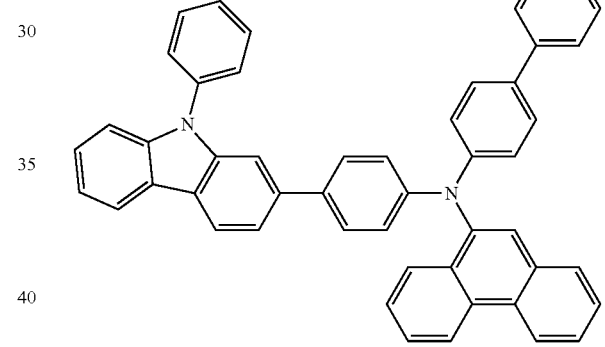
1-65
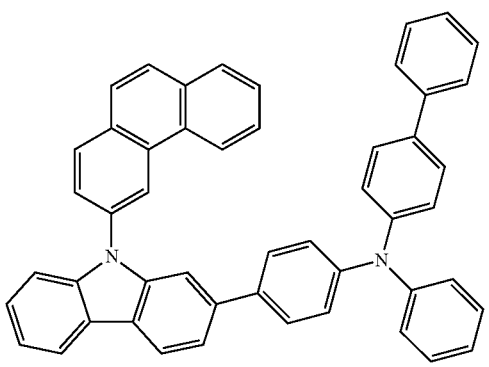

1-66
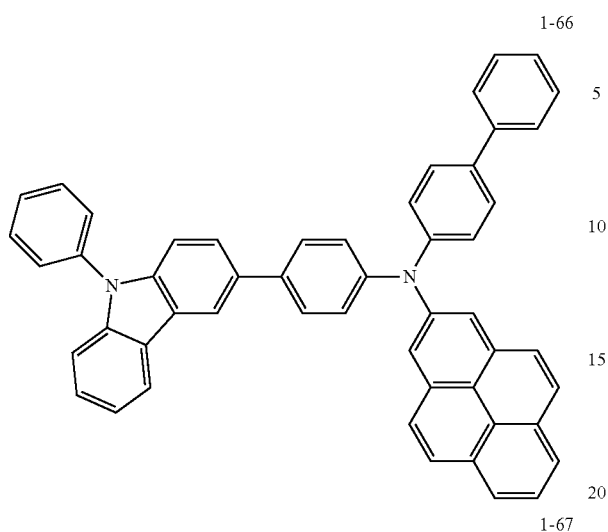
1-67
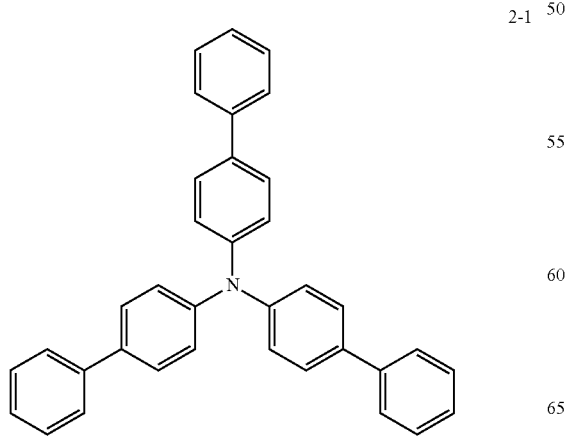
7. The organic electronic element according to claim 4, wherein the compounds represented by the formula (2) of the emitting-auxiliary layer or by the formulas (8) to (12) are one of the following compounds,
2-1
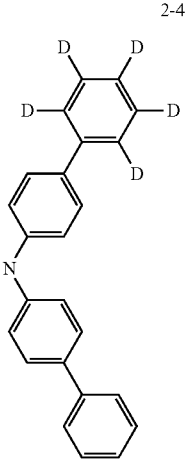
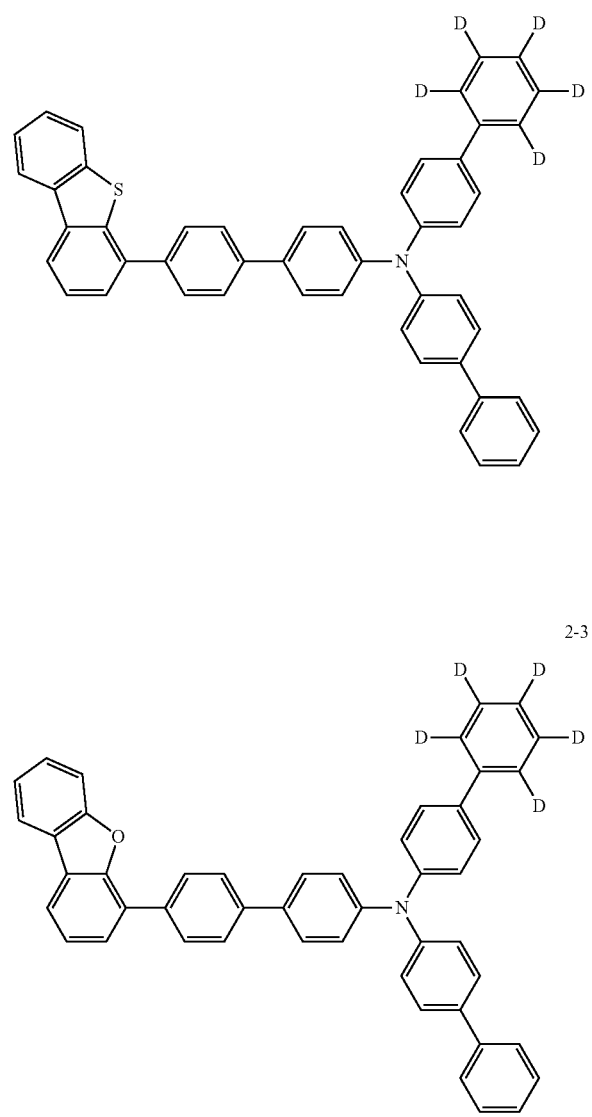

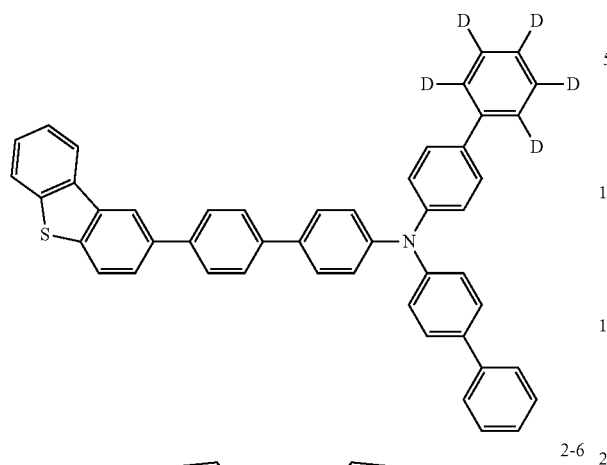
2-5
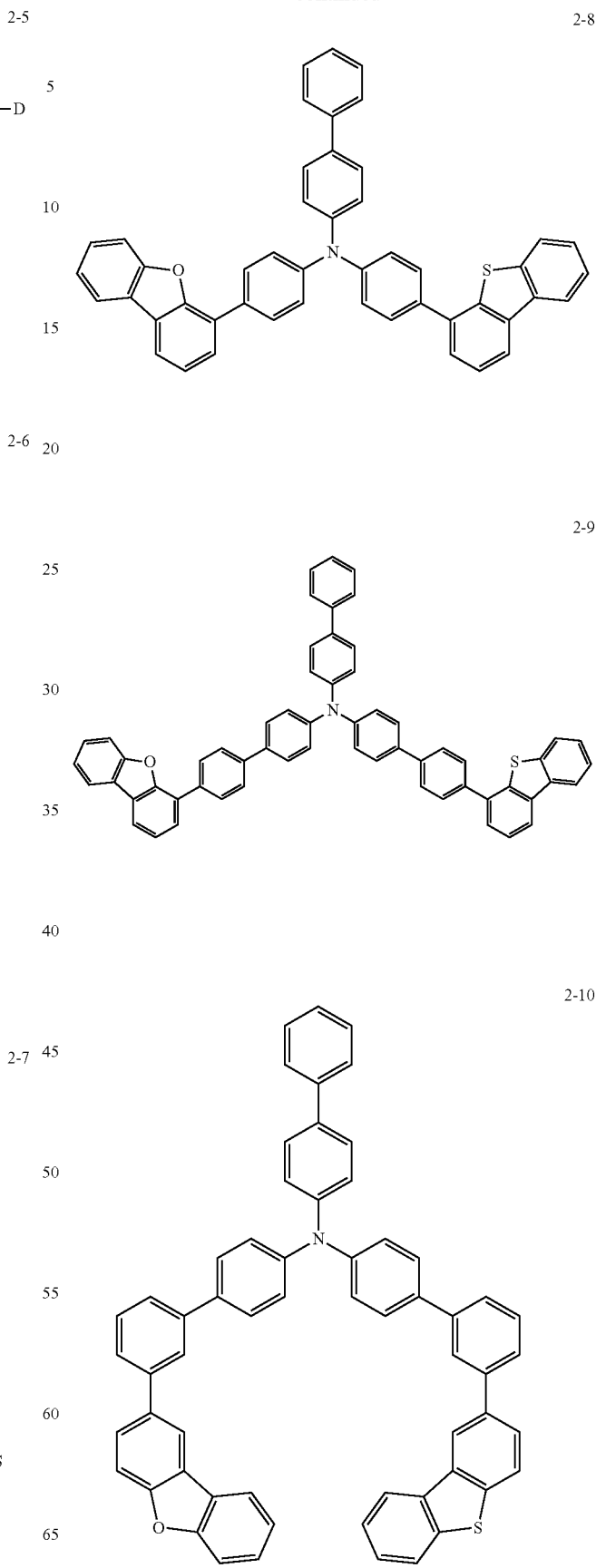
2-6
2-7
2-8
2-9
2-10

2-11
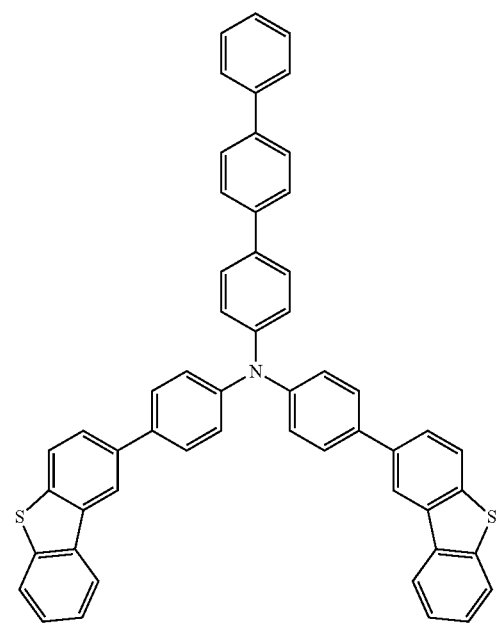
2-12
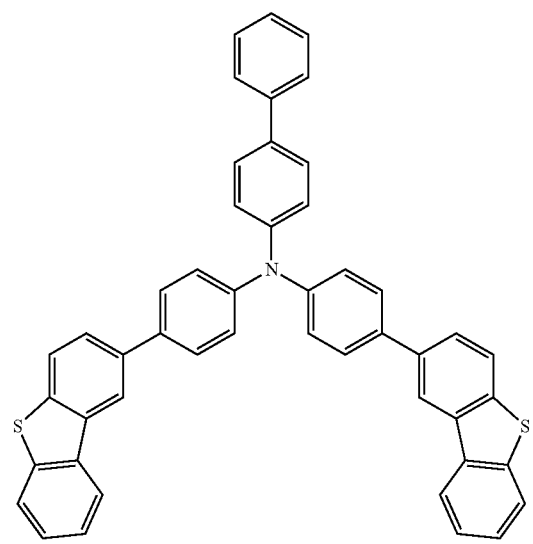
2-13
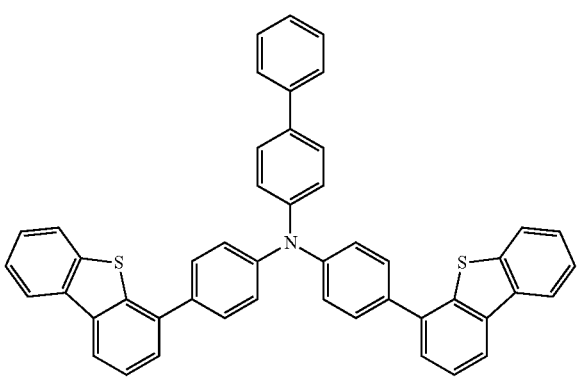
2-14
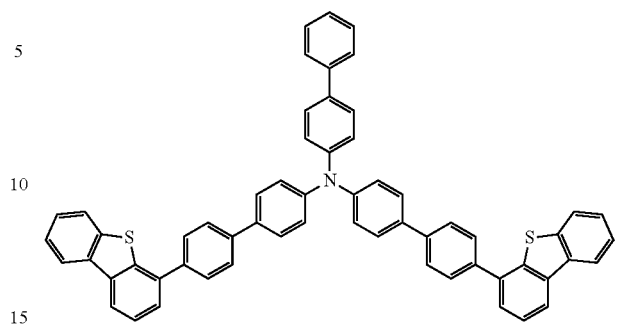
2-15
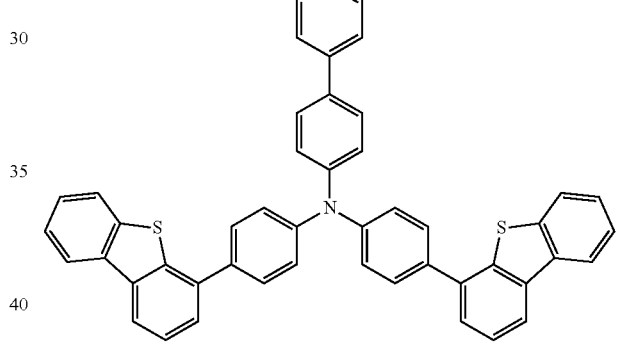
2-16

2-17
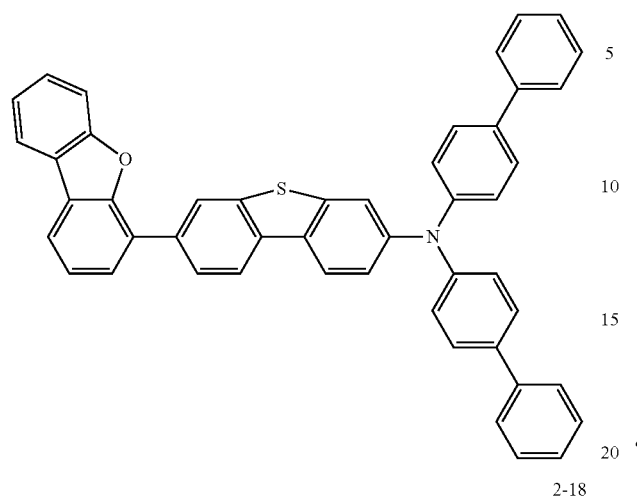
2-20
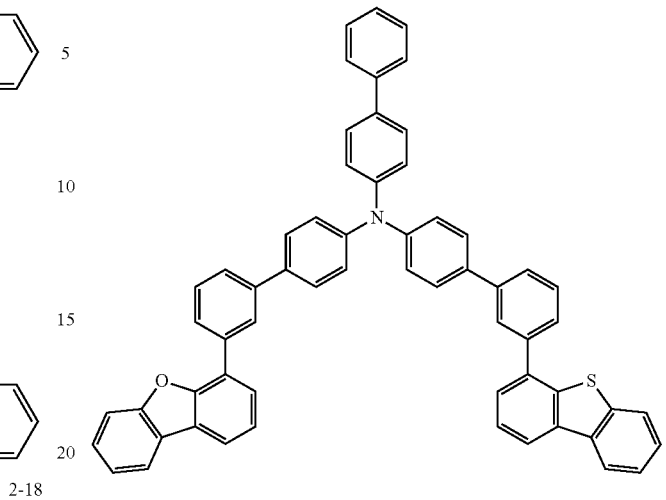
2-18
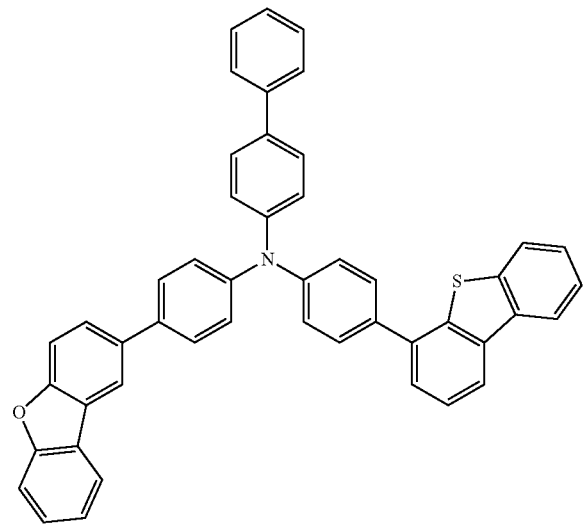
2-21
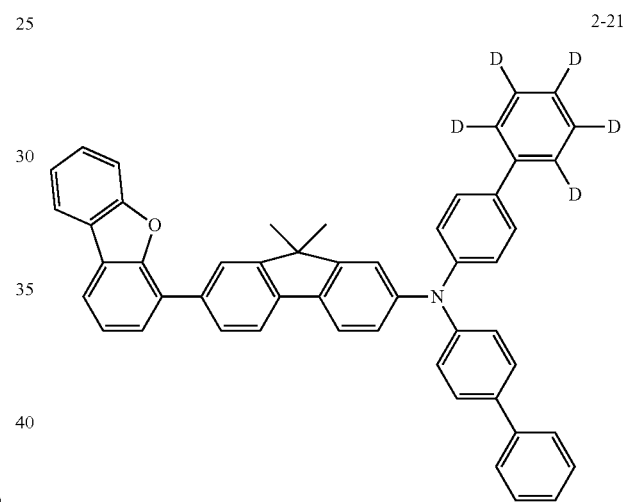
2-19
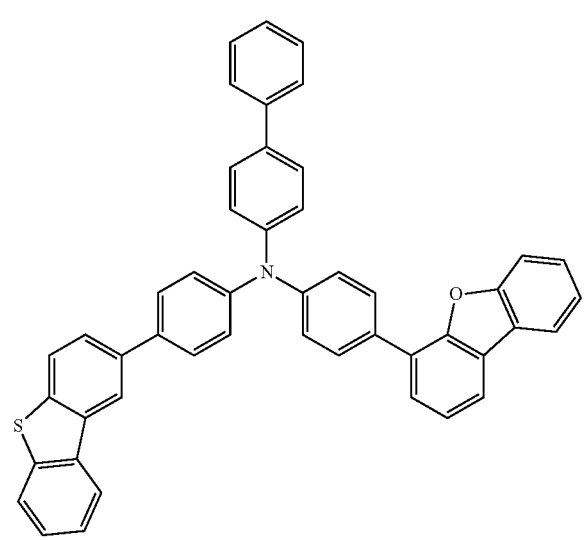
2-22
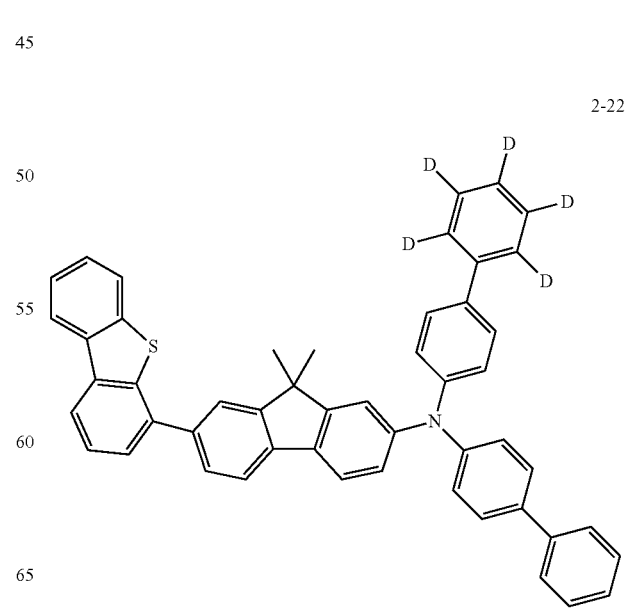

2-23
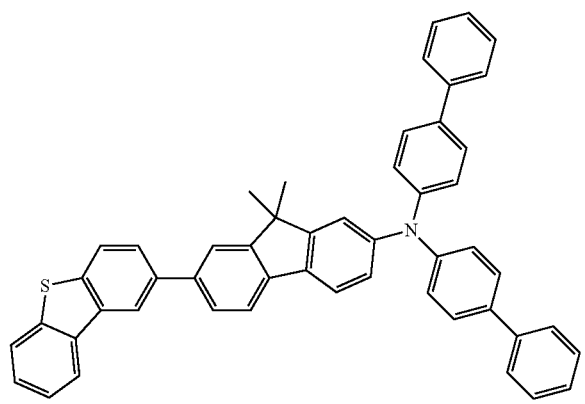
2-26
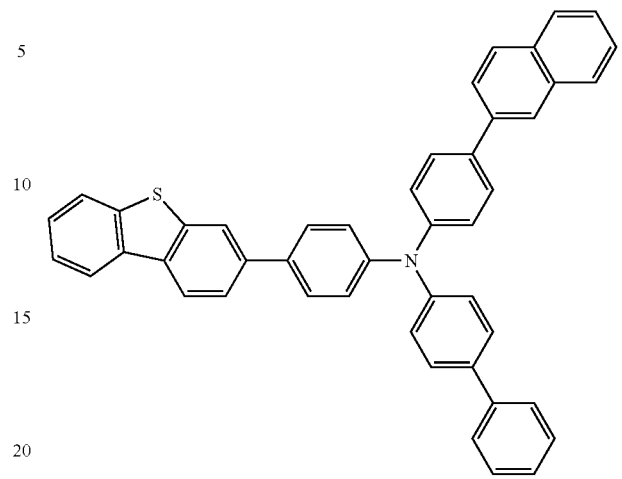
2-24
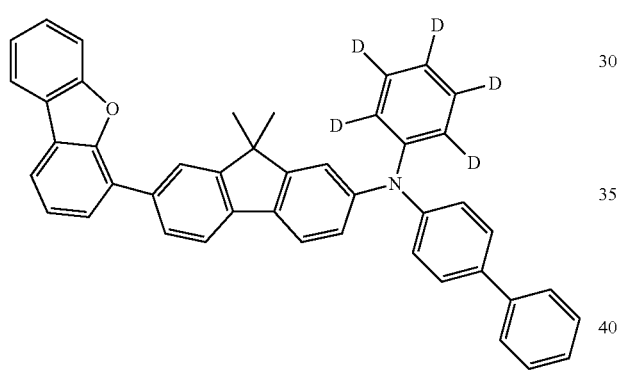
2-27
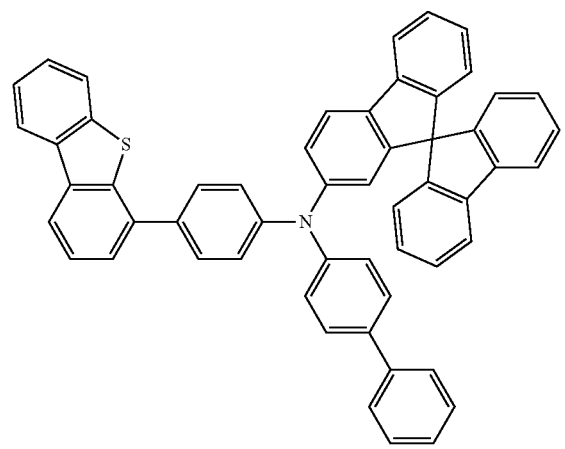
2-25
2-28
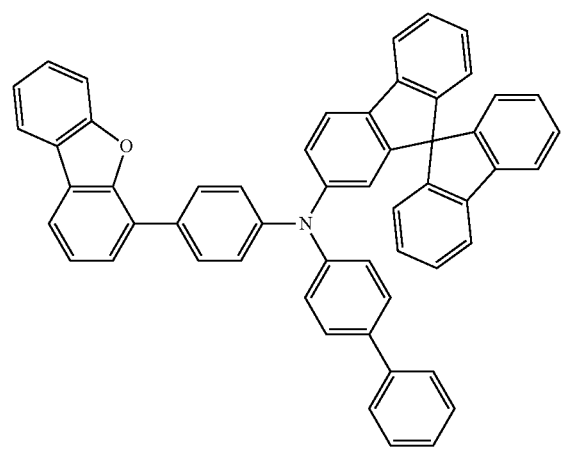

2-29
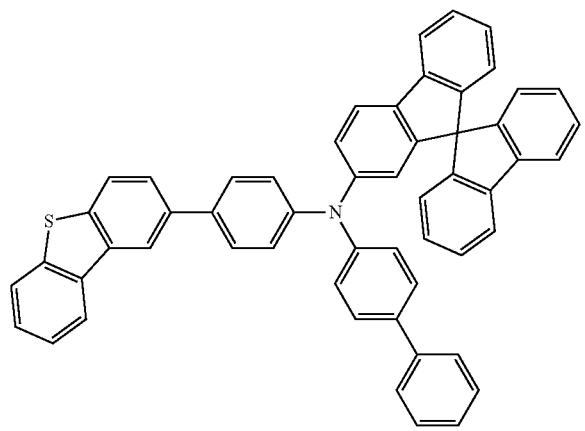
2-32
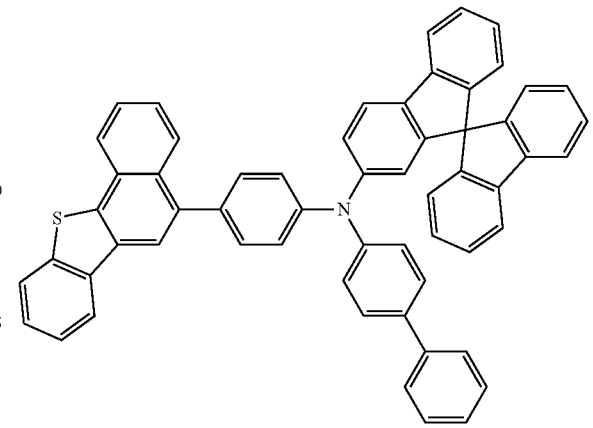
2-30
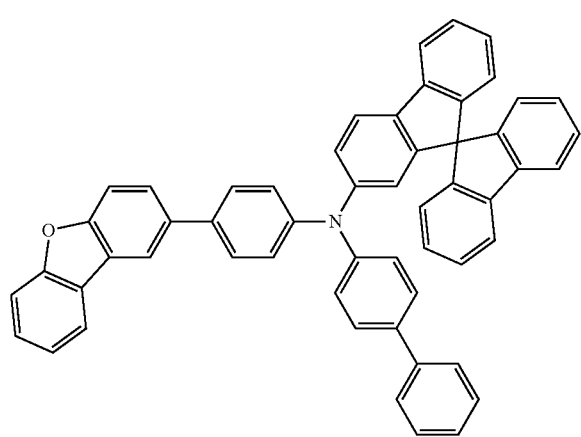
2-33
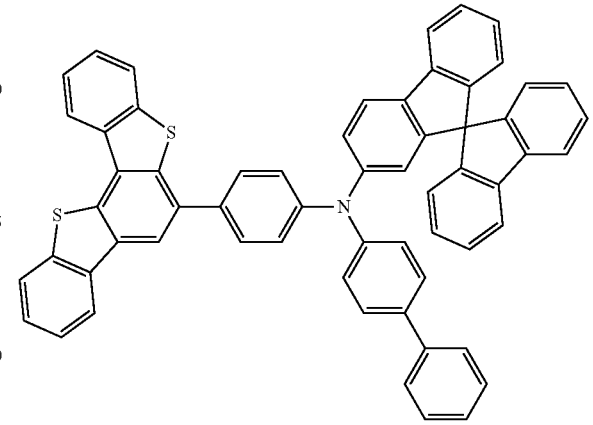
2-31
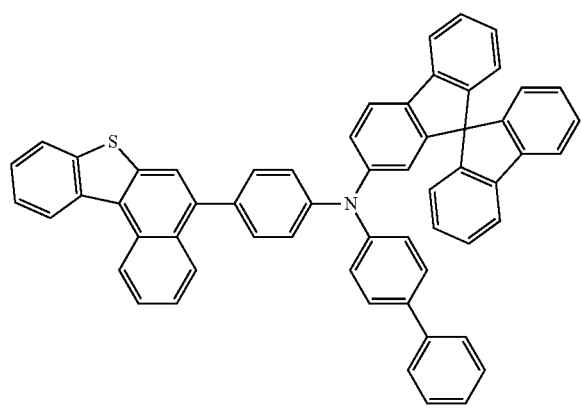
2-34
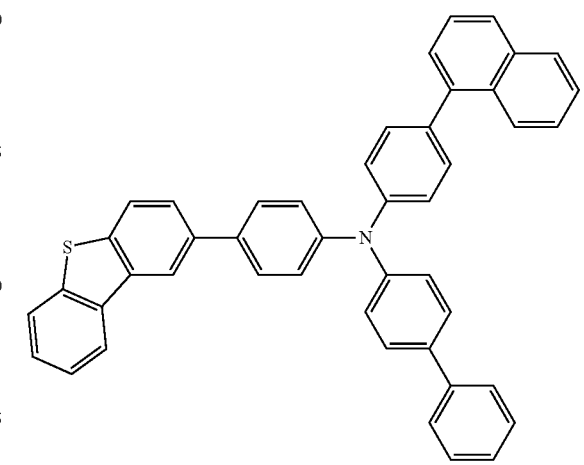

2-35
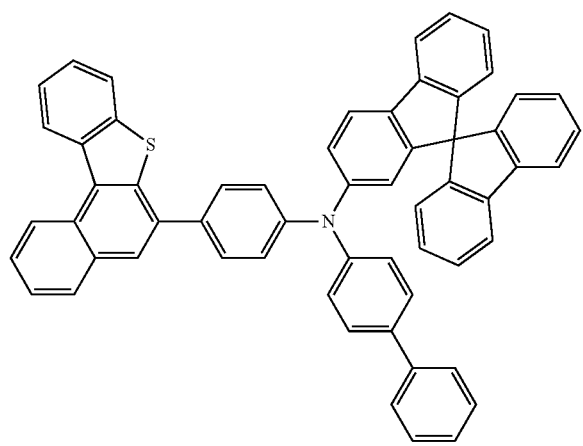
2-36
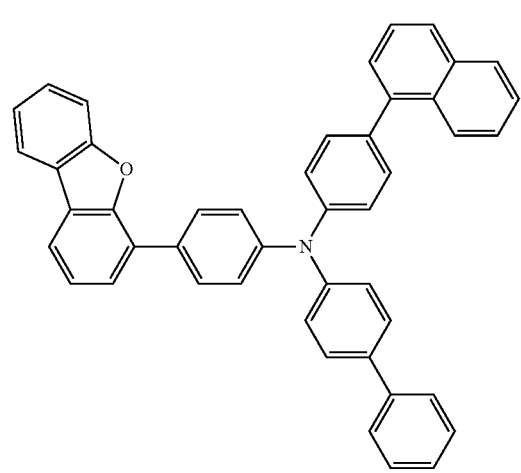
2-37
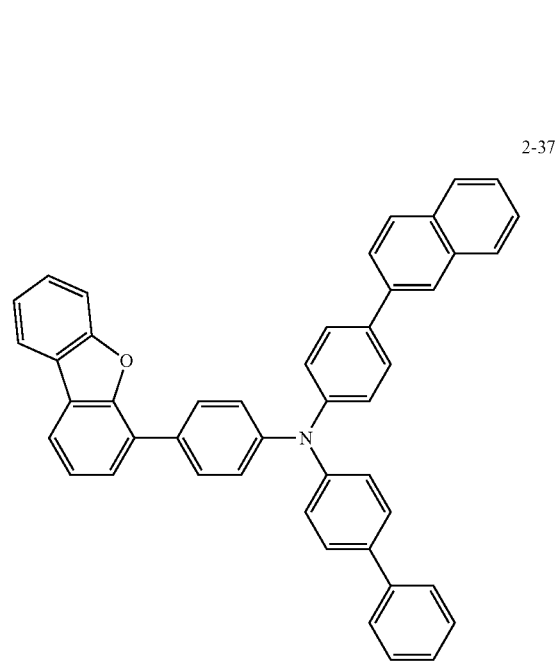
2-38
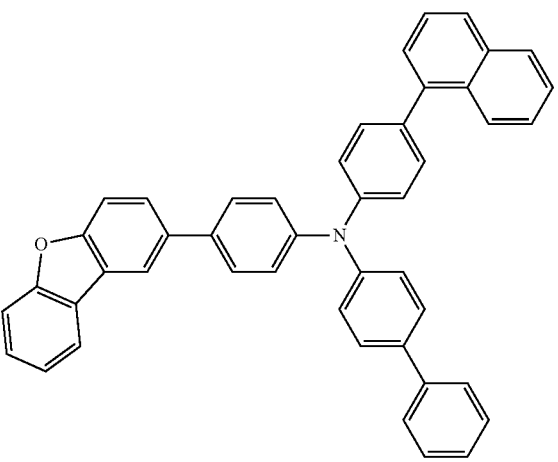
2-39
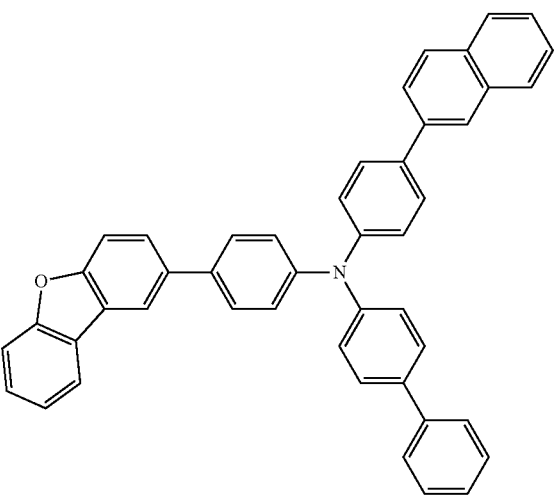
2-40
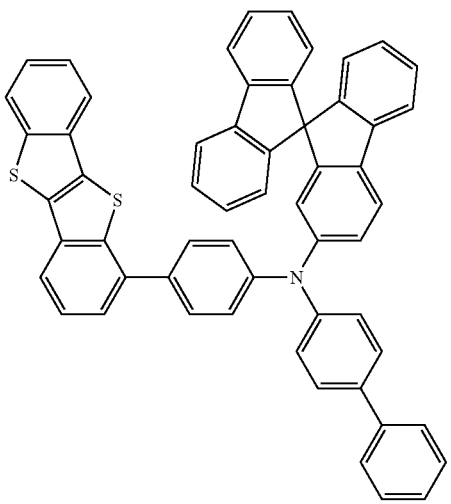

2-41
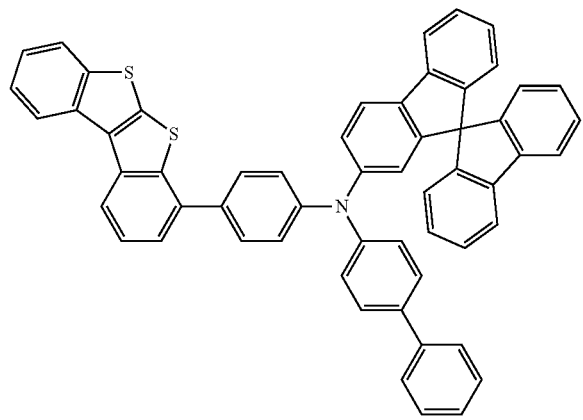
2-42
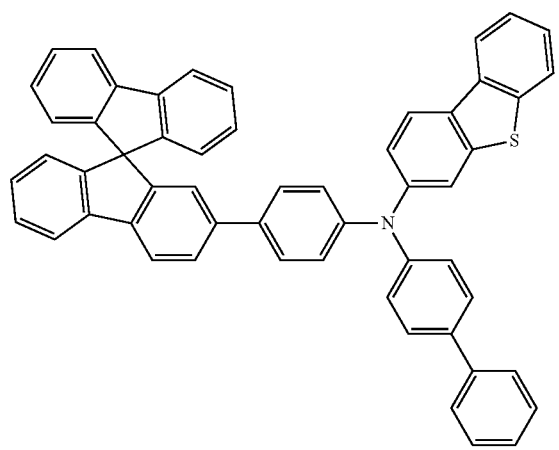
2-43
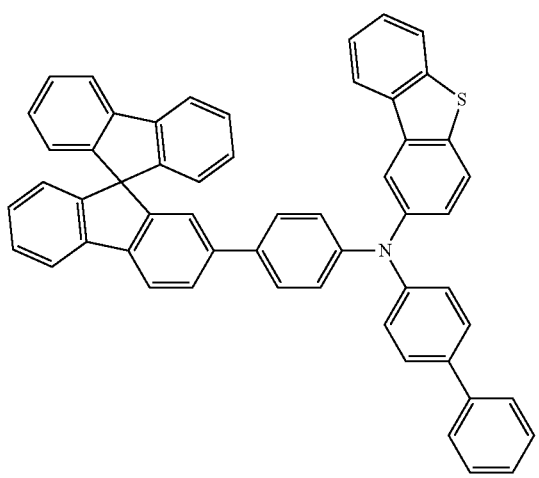
2-44
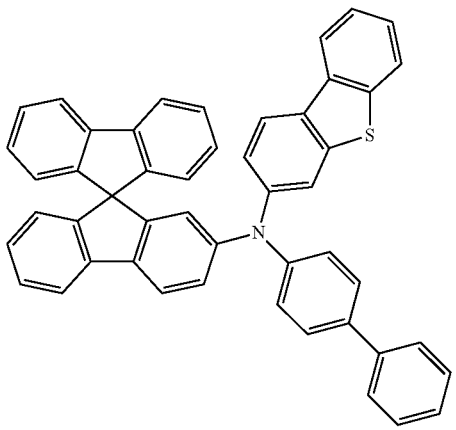
2-45
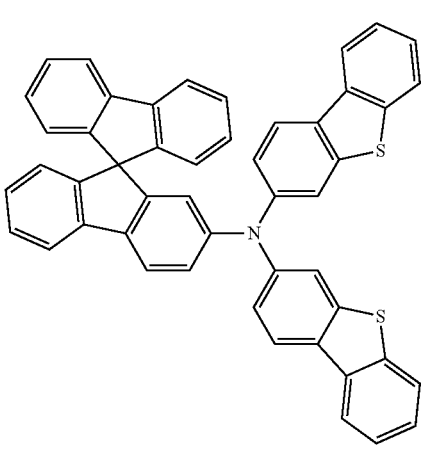
2-46
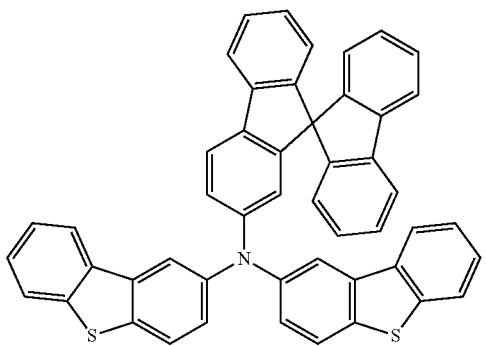
2-47
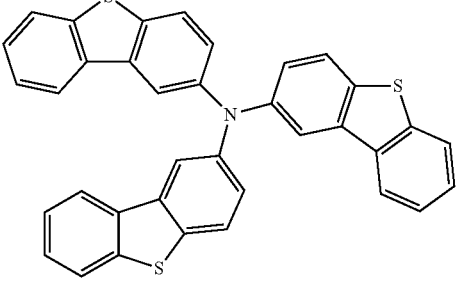

2-48
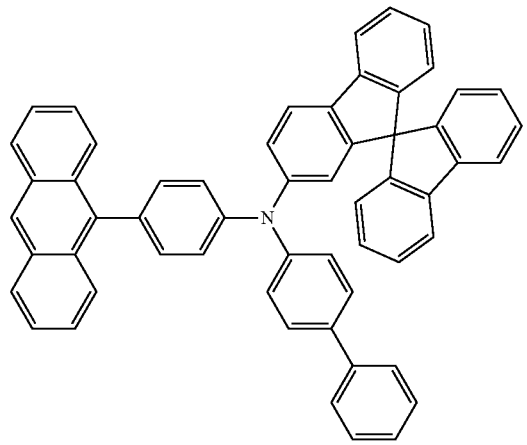
2-49
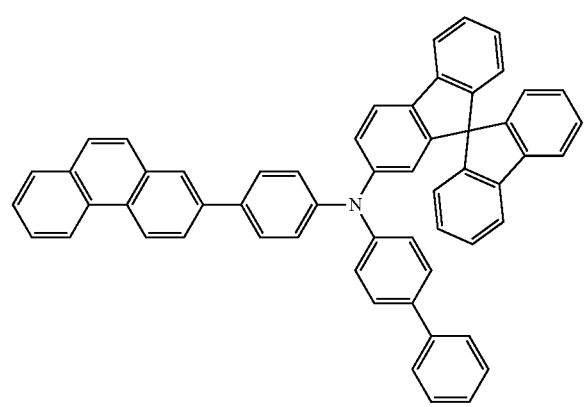
2-50
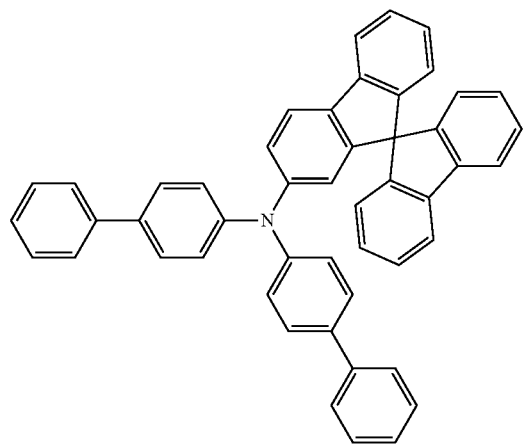
2-51
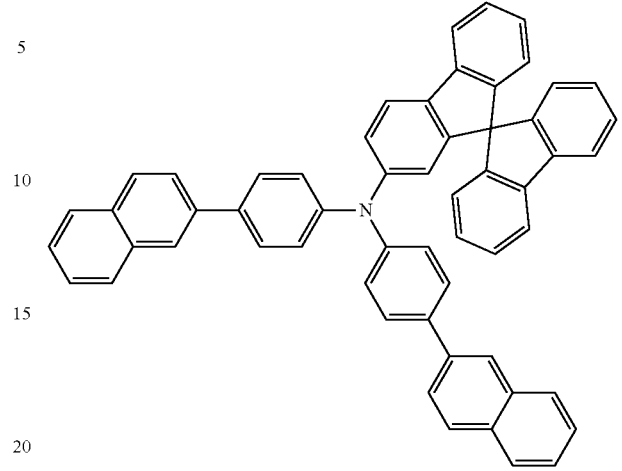
2-52
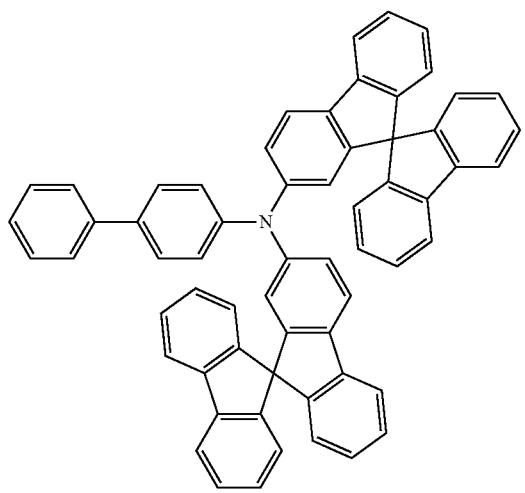
2-53
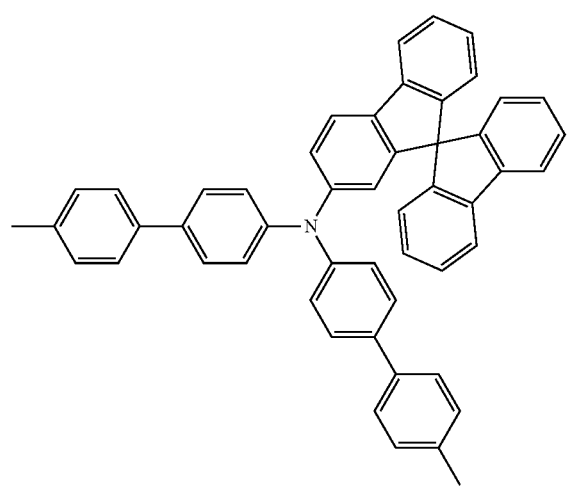

2-54
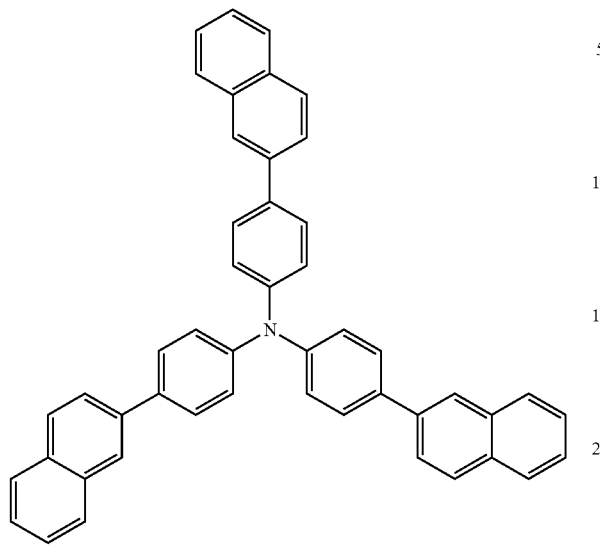
2-57
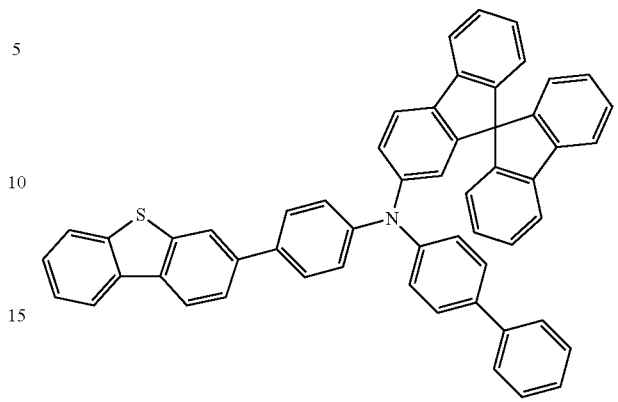
2-55
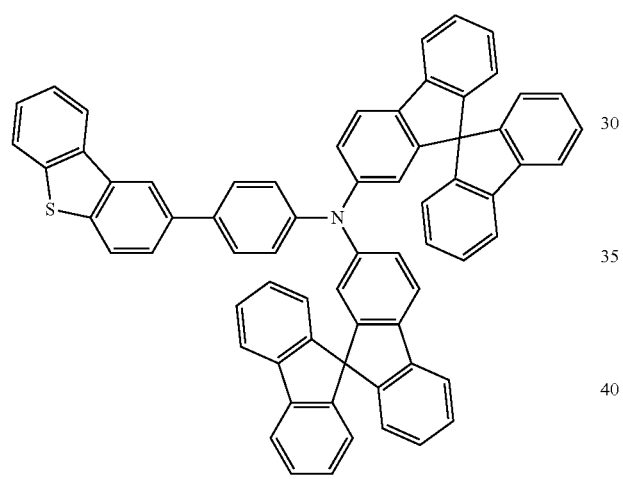
2-58
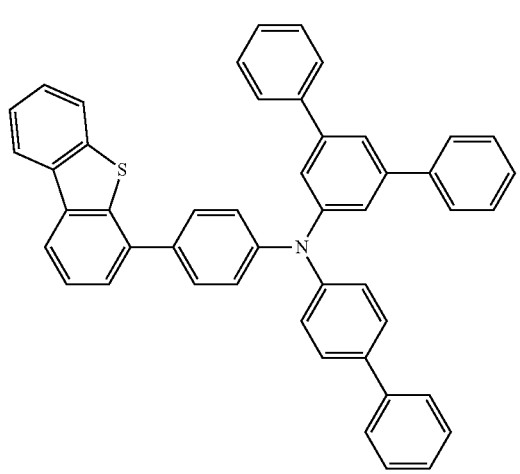
2-56
2-59
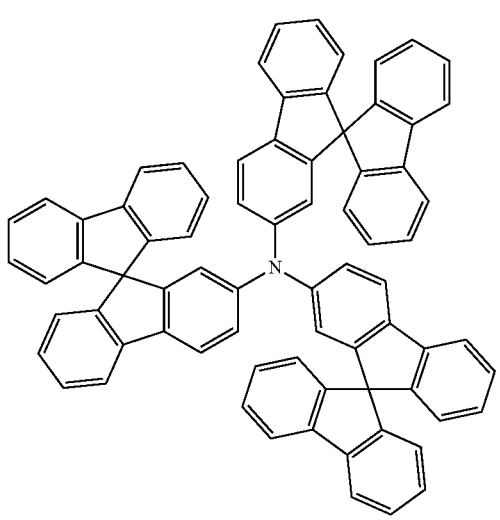

2-60
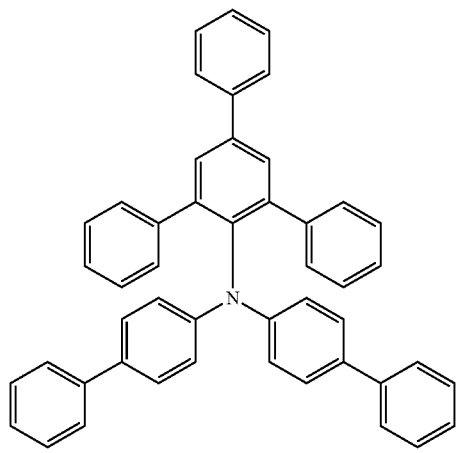
2-63
2-61
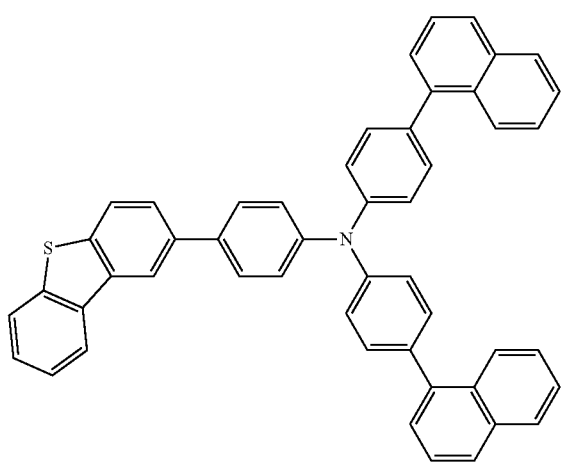
2-64
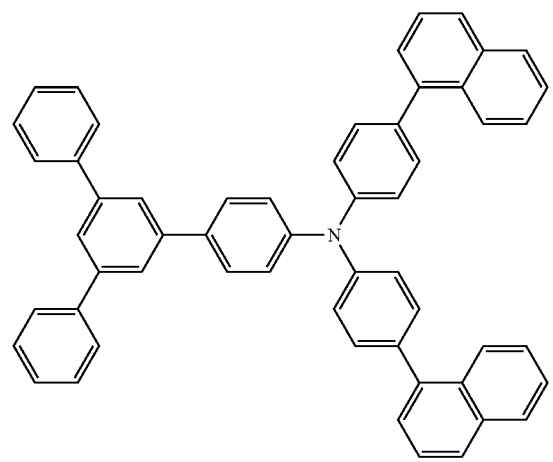
2-62
2-65
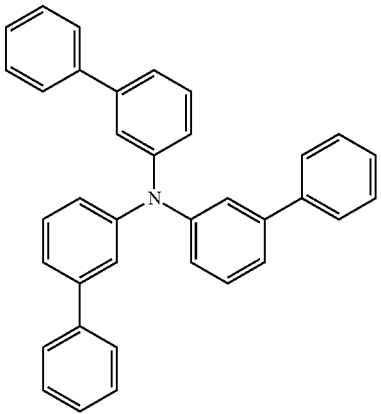

2-66

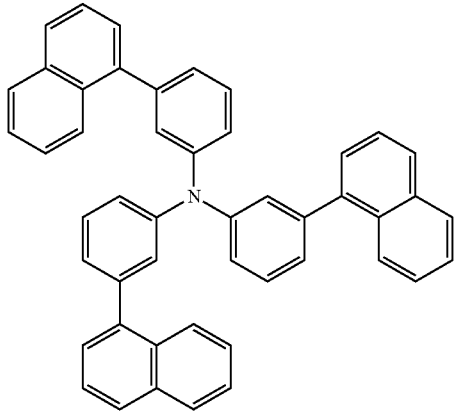

2-67

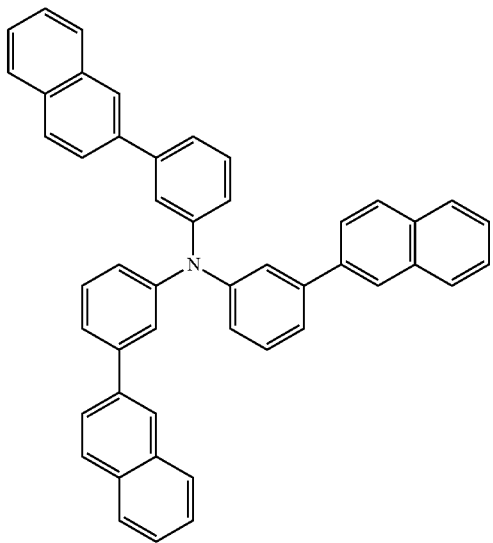

2-68

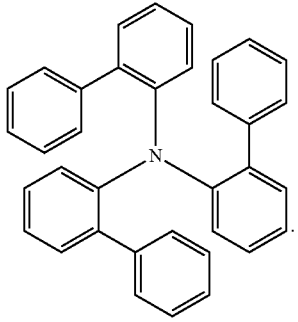

8. The organic electronic element according to claim 1, wherein all of $Ar^4$ to $Ar^6$ in the formula (2) are aryl groups of $C_6$ to $C_{60}$.

9. The organic electronic element according to claim 1, wherein at least one of $Ar^4$ to $Ar^6$ of the Formula (2) is an $C_6$-$C_{60}$ heteroaryl group.

10. The organic electronic element according to claim 2, wherein the hole transport layer comprises a compound represented by Formula (3) and the emitting auxiliary layer comprises a compound represented by Formula (2).

11. The organic electronic element according to claim 2, wherein the hole transport layer comprises a compound represented by Formula (4) and the emitting auxiliary layer comprises a compound represented by Formula (2).

12. The organic electronic element according to claim 1, wherein the emitting auxiliary layer comprises a mixture of two or more compounds represented by the formula (2).

13. A display device comprising the organic electronic element of claim 2; and a control part driving the display apparatus.

14. The display device according to claim 13, wherein the organic electronic element is at least one of an OLED, an organic solar cell, an organic photo conductor (OPC), Organic transistor (organic TFT) and an element for monochromic or white illumination.

* * * * *

UNITED STATES PATENT AND TRADEMARK OFFICE
CERTIFICATE OF CORRECTION

PATENT NO. : 10,991,888 B2
APPLICATION NO. : 15/999002
DATED : April 27, 2021
INVENTOR(S) : Lee et al.

Page 1 of 1

It is certified that error appears in the above-identified patent and that said Letters Patent is hereby corrected as shown below:

In the Claims

Claim 1, Column 101, Lines 45-50:
Please delete:

" 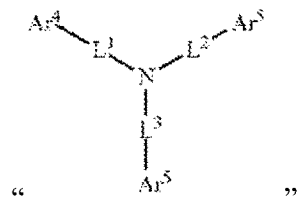 "

And replace with:

-- 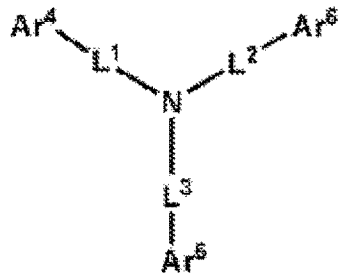 --

Claim 1, Column 101, Line 58:
Please delete:
"aklenyl"

And replace with:
-- alkenyl --

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*